United States Patent
Pinto et al.

(10) Patent No.: US 10,906,886 B2
(45) Date of Patent: Feb. 2, 2021

(54) SUBSTITUTED 5,6,7,8-TETRAHYDROIMIDAZO[1,5-A]PYRAZINES AS FACTOR XIA INHIBITORS

(71) Applicant: BRISTOL-MYERS SQUIBB COMPANY, Princeton, NJ (US)

(72) Inventors: Donald J. P. Pinto, Churchville, PA (US); Indawati De Lucca, Pennington, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 15/982,038

(22) Filed: May 17, 2018

(65) Prior Publication Data

US 2018/0265494 A1    Sep. 20, 2018

Related U.S. Application Data

(62) Division of application No. 15/643,891, filed on Jul. 7, 2017, now Pat. No. 10,000,466, which is a division of application No. 15/183,051, filed on Jun. 15, 2016, now Pat. No. 9,725,435, which is a division of application No. 14/799,681, filed on Jul. 15, 2015, now Pat. No. 9,394,276, which is a division of application No. 14/350,417, filed as application No. PCT/US2012/059859 on Oct. 12, 2012, now Pat. No. 9,108,951.

(60) Provisional application No. 61/547,305, filed on Oct. 14, 2011.

(51) Int. Cl.
| | |
|---|---|
| A61K 31/4985 | (2006.01) |
| C07D 487/04 | (2006.01) |
| C07D 401/10 | (2006.01) |
| C07D 401/14 | (2006.01) |
| C07D 413/14 | (2006.01) |
| C07D 217/26 | (2006.01) |
| C07D 471/04 | (2006.01) |
| C07D 401/12 | (2006.01) |

(52) U.S. Cl.
CPC ......... *C07D 401/10* (2013.01); *C07D 217/26* (2013.01); *C07D 401/12* (2013.01); *C07D 401/14* (2013.01); *C07D 413/14* (2013.01); *C07D 471/04* (2013.01); *C07D 487/04* (2013.01)

(58) Field of Classification Search
CPC .......................... A61K 31/4986; C07D 487/04
USPC ......................................... 514/249; 544/350
See application file for complete search history.

(56) References Cited

U.S. PATENT DOCUMENTS

| | | | |
|---|---|---|---|
| 5,624,936 | A | 4/1997 | deSolms |
| 5,869,682 | A | 2/1999 | deSolms |
| 9,108,951 | B2 | 8/2015 | Orwat et al. |
| 10,000,466 | B2 | 6/2018 | Orwat et al. |

FOREIGN PATENT DOCUMENTS

| | | |
|---|---|---|
| CN | 1441785 A | 9/2003 |
| DE | 40 34 829 A1 | 5/1992 |
| EP | 0 525 420 B1 | 5/1999 |
| EP | 1 016 663 A1 | 7/2000 |
| EP | 1 125 925 A1 | 8/2001 |
| FR | 1525186 | 5/1968 |
| FR | 7155 M | 2/1970 |
| JP | 2007-501844 A | 2/2007 |
| JP | 2010-529991 A | 9/2010 |
| JP | 2010532162 A | 10/2017 |
| WO | WO 93/20099 A2 | 10/1993 |
| WO | WO 96/34010 A2 | 10/1996 |
| WO | WO 97/36891 A1 | 10/1997 |
| WO | WO 99/47545 A2 | 9/1999 |
| WO | WO 99/61444 A2 | 12/1999 |
| WO | WO 00/18733 A1 | 4/2000 |
| WO | WO 00/40571 A1 | 7/2000 |
| WO | WO 00/61608 A2 | 10/2000 |
| WO | WO 01/85695 A1 | 11/2001 |
| WO | WO 02/18369 A2 | 3/2002 |
| WO | 03016248 A2 | 2/2003 |

(Continued)

OTHER PUBLICATIONS

Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).

(Continued)

*Primary Examiner* — Douglas M Willis
(74) *Attorney, Agent, or Firm* — Mintz, Levin, Cohn, Ferris, Glovsky and Popeo, P.C.

(57) ABSTRACT

The present invention provides compounds of Formula (I):

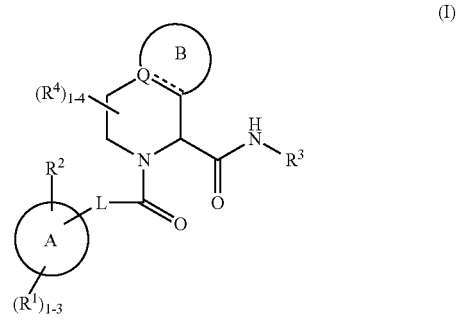

or stereoisomers, pharmaceutically acceptable salts thereof, wherein all of the variables are as defined herein. These (Continued)

compounds are inhibitors of factor XIa andor plasma kallikrein which may be used as medicaments.

4 Claims, No Drawings

(56) References Cited

FOREIGN PATENT DOCUMENTS

| WO | WO 03/041641 A2 | 5/2003 |
|---|---|---|
| WO | WO 2004/080971 A1 | 9/2004 |
| WO | WO 2004/094372 A2 | 11/2004 |
| WO | WO 2005/014533 A2 | 2/2005 |
| WO | WO 2005/099709 A2 | 10/2005 |
| WO | WO 2005/123050 A2 | 12/2005 |
| WO | WO 2005/123680 A1 | 12/2005 |
| WO | WO 2006/017295 A2 | 2/2006 |
| WO | WO 2006/076575 A2 | 7/2006 |
| WO | WO 2006/089005 A2 | 8/2006 |
| WO | WO 2007/054453 A2 | 5/2007 |
| WO | WO 2007/070816 A2 | 6/2007 |
| WO | WO 2007/070818 A1 | 6/2007 |
| WO | WO 2007/070826 A1 | 6/2007 |
| WO | WO 2008/076805 A2 | 6/2008 |
| WO | WO 2008/157162 A1 | 12/2008 |
| WO | WO 2009/114677 A1 | 9/2009 |
| WO | WO 2010/151317 A1 | 12/2010 |
| WO | WO 2011/002520 A2 | 1/2011 |
| WO | WO 2011/017296 A1 | 2/2011 |
| WO | WO 2011/100401 A1 | 8/2011 |
| WO | WO 2011/100402 A1 | 8/2011 |
| WO | WO 2013/009527 A2 | 1/2013 |
| WO | WO 2013/022814 A1 | 2/2013 |
| WO | WO 2013/022818 A1 | 2/2013 |
| WO | WO 2013/055984 A1 | 4/2013 |
| WO | WO 2013/056034 A1 | 4/2013 |
| WO | WO 2013/056060 A1 | 4/2013 |
| WO | WO 2013/093484 A1 | 6/2013 |
| WO | WO 2013/111107 A1 | 8/2013 |
| WO | WO 2013/111108 A1 | 8/2013 |
| WO | WO 2013/118805 A1 | 8/2013 |
| WO | WO 2013/167669 A1 | 11/2013 |
| WO | WO 2014/014050 A1 | 1/2014 |
| WO | WO 2014/022766 A1 | 2/2014 |
| WO | WO 2014/022767 A1 | 2/2014 |

OTHER PUBLICATIONS

Cho, J.E. et al., "Characterization of Binding Mode for Human Coagulation Factor XI (FXI) Inhibitors", Bull. Korean Chem. Soc., vol. 34, No. 4, pp. 1212-1220 (2013).

Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).

Jiang, G. et al., "Highly Efficient Oxidation of Amines to Imines by Singlet Oxygen and Its Application in Ugi-Type Reactions", Organic Letters, vol. 11, No. 20, pp. 4568-4571 (2009).

Li, J.J. et al., "Tetrahydroisoquinoline 1-carboxamides as growth hormone secretagogues", Bioorganic & Medicinal Chemistry Letters, vol. 15, pp. 1799-1802 (2005).

Matafonov, A. et al., "Evidence for factor IX-independent roles for factor XIa in blood coagulation", Journal of Thrombosis and Haemostasis, vol. 11, pp. 2118-2127 (2013).

Ngouansavanh, T. et al., "IBX-Mediated Oxidative Ugi-Type Multicomponent Reactions: Application to the N and C1 Functionalization of Tetrahydroisoquinoline", Angew. Chem. Int. Ed., vol. 46, pp. 5775-5778 (2007).

Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).

Schuster, I. et al., "Synthesis of 1,2,3,4-Tetrahydroisoquinoline-1-Carboxylic Acid Derivatives via Ugi Reactions", Letters in Organic Chemistry, vol. 4, No. 2, pp. 102-108 (2007).

Schuster, I. et al., "Synthesis of 1,2,3,4-Tetrahydroisoquinoline-1-carboxylic Acid Derivatives via Ugi Reactions", Magyar Kémiai Folyóirat (Hungarian Journal of Chemistry), vol. 116, No. 3, pp. 126-130 (2010).

Wu, Y.-J. et al., "Discovery of (S,E)-3-(2-fluorophenyl)-N-(1-(3-(pyridin-3-yloxy)phenyl)ethyl)-acrylamide as a potent and efficacious KCNQ2 (Kv7.2) opener for the treatment of neuropathic pain", Bioorganic & Medicinal Chemistry Letters, vol. 23, pp. 6188-6191 (2013).

Boehme et al. (1972) "Alkylation, acylahon, and reduction studies on 1-cyano-1,2-dihydro- and H.2,3,4-tetrahydroisoquinoline derivatives," Chemische Berichte. 105(5):1578-1585.

International Preliminary Report on Patentability for PCT International Applicaion No. PCT/US2012/059859, dated Apr. 24, 2014, 7 pages.

International Search Report and Written Opinion for PCT International Application No. PCT/US2012/059859, dated Nov. 28, 2012, 10 pages.

Ngouansavanh, T. and Zhu, J. "IBX-Mediated Oxidative Ugi-Type Multicomponent Reactions: Application to the N and C1 Functionalization of Tetrahydroisoquinoline", Angew. Chem. Int. Ed. 2007, 46, 5775-5778.

Caballero, J.; Zampini, F. M.; Collina, S.; Fernandez, M. "Quantitative Structure-Activity Relationship Modeling of Growth Hormone Secretagogues Agonist Activity of some Tetrahydroisoquinoline 1-Carboxamides" Chem. Biol. Drug, Des. 2007, 69(1), 48-55.

Jiang, G.; Chen, J.; Huang, J.-S.; Che, C-M."Highly Efficient Oxidation of Amines to Imines by Singlet Oxygen and Its Application in Ugi-Type Reactions", Org. Lett. 2009, 11(20), 4568-4571.

Li, J. J.; Wang, H.; Qu, F.; Musial, C.; Tino, J.A.; Robl, J.A.; Slusarchyk, D.; Golla, R.; Seethala, R.; Dickinson, K.; Giupponi, L.; Grover, G.; Sleph, P.; Flyn, N.; Murphy, B.J.; Gordon, D.; Kung, M.; Stoffel, R. "Tetrahydroisoquinoline carboxamides as Growth Hormone Secretagogues", Bioorg. & Med. Chem. Lett. 2005, 15(7), 1799-1802.

SUBSTITUTED 5,6,7,8-TETRAHYDROIMIDAZO[1,5-A]PYRAZINES AS FACTOR XIA INHIBITORS

CROSS-REFERENCE TO RELATED APPLICATIONS

This application is a Divisional of U.S. application Ser. No. 15/643,891, filed Jul. 7, 2017, now allowed, which is a Divisional of U.S. application Ser. No. 15/183,051, filed Jun. 15, 2016, now U.S. Pat. No. 9,725,435, which is a Divisional of U.S. application Ser. No. 14/799,681, filed Jul. 15, 2015, now U.S. Pat. No. 9,394,276, which is a Divisional of U.S. application Ser. No. 14/350,417, filed Apr. 8, 2014, now U.S. Pat. No. 9,108,951, which is the 371 National Stage of International Application No. PCT/2012/059859, filed on Oct. 12, 2012, which claims the priority benefit of U.S. Provisional Application No. 61/547,305, filed Oct. 14, 2011, the contents of which are herein incorporated by reference in their entirety.

FIELD OF THE INVENTION

The present invention provides novel substituted tetrahydroisoquinoline (THQ) compounds, and their analogues thereof, which are inhibitors of factor XIa or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

SUMMARY OF THE INVENTION

The present invention provides novel substituted tetrahydroisoquinoline compounds, and their analogues thereof, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two, other agent(s).

These and other features of the invention will be set forth in expanded form as the disclosure continues.

DETAILED DESCRIPTION OF THE INVENTION

I. Compounds of the Invention

In a first aspect, the present invention provides compounds of Formula (I):

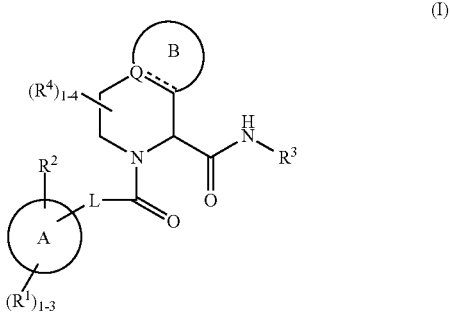

or stereoisomers, tautomers, pharmaceutically acceptable salts, or solvates thereof, wherein:

ring A is $C_{3-10}$ carbocycle;

L is selected from the group consisting of: —$CHR^{10}CHR^{10}$—, —$CR^{10}$=$CR^{10}$—, —C≡C—, —$CHR^{10}NH$—, —$NHCHR^{10}$—, —$SCH_2$—, —$CH_2S$—, —$SO_2CH_2$—, —$CH_2SO_2$—, —$NHCH_2$—, and —$CH_2NH$—;

Q is selected from the group consisting of: C, CH, and N;

---- is an optional bond; provided when Q is N, the optional bond is absent;

ring B is 5- to 6-membered heterocycle containing carbon atoms and 1-3 heteroatoms selected from the group consisting of N, $NR^6$, O, and $S(O)_p$, wherein said heterocycle is substituted with 0-3 $R^5$;

optionally, ring B is further fused with a phenyl ring substituted with 0-2 $R^5$ or 5-to 6-membered heteroaryl containing carbon atoms and 1-2 heteroatoms selected from the group consisting of N, $NR^6$, O, and $S(O)_p$; wherein said heteroaryl is substituted with 0-2 $R^5$;

$R^1$, at each occurrence, is selected from the group consisting of: H, halo, $C_{1-6}$ alkyl, $C_{1-4}$ alkoxy, $C_{1-4}$ alkylthio, OH, SH, $CHF_2$, $CF_3$, $OCF_3$, CN, $NH_2$, $COC_{1-4}$ alkyl, $CO_2$($C_{1-4}$ alkyl), —$CH_2CO_2H$, —$CH_2CO_2$($C_{1-4}$ alkyl), —$CH_2NH_2$, —$CONH_2$, —$CONH(C_{1-4}$ alkyl), —NHCO ($C_{1-4}$ alkyl), —$NHCO_2(C_{1-4}$ alkyl), —$NHSO_2(C_{1-4}$ alkyl), —$SO_2NH_2$, and —$C(=NH)NH_2$;

$R^2$ is selected from the group consisting of: H, halo, CN, OH, $C_{1-6}$ alkyl, $C_{1-4}$ alkoxy, $C_{1-6}$haloalkyl, $C_{1-6}$haloalkoxy, $CO(C_{1-4}$ alkyl), $CONH_2$, $CO_2H$, $CH_2NH_2$, and a 5- to 7-membered heterocycle comprising carbon atoms and 1-4 heteroatoms selected from N, $NR^c$, O, and $S(O)_p$, wherein said heterocycle is substituted with 0-2 $R^{2a}$;

$R^{2a}$, at each occurrence, is selected from the group consisting of: H, halo, $C_{1-4}$ alkyl, —$CH_2OH$, $C_{1-4}$ alkoxy, OH, $CF_3$, $OCF_3$, CN, $NH_2$, $CO_2H$, $CO_2(C_{1-4}$ alkyl), $CO(C_{1-4}$ alkyl), —$CONH_2$, —$CH_2OH$, —$CH_2OC_{1-4}$alkyl, —$CH_2NH_2$—, $CONH(C_{1-4}$ alkyl), —$CON(C_{1-4}$ alkyl)$_2$, —$SO_2(C_{1-4}$ alkyl), —$SO_2NH_2$, —$SO_2NH(C_{1-4}$ alkyl), and —$SO_2N(C_{1-4}$ alkyl)$_2$;

$R^3$ is selected from the group consisting of: $C_{1-6}$ alkyl substituted with 1-3 $R^{3a}$, —$(CH_2)_n$—$C_{3-10}$ carbocycle substituted with 0-3 $R^{3a}$ or —$(CH_2)_n$-5-10 membered heterocycle containing carbon atoms and 1-4 heteroatoms selected from the group consisting of N, $NR^7$, O, and $S(O)_p$; wherein said heterocycle is substituted with 0-3 $R^{3a}$;

$R^{3a}$, at each occurrence, is selected from the group consisting of: H, halo, $C_{1-4}$ alkyl, —OH, $C_{1-4}$ alkoxy, —CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO_2$—$C_{1-4}$ alkylene-O ($C_{1-4}$ alkyl), —$CO_2$—$C_{1-4}$ alkylene-$N(C_{1-4}$ alkyl)$_2$, —$CO_2$—$C_{1-4}$ alkylene-O—$C_{1-4}$ alkylene-$N(C_{1-4}$ alkyl)$_2$, —$CO_2$—$C_{1-4}$ alkylene-O—$C_{1-4}$ alkylene-O($C_{1-4}$ alkyl), —$CONH_2$, —$CONH(C_{1-6}$ alkyl), —$CON(C_{1-4}$ alkyl)$_2$, —CONH—$C_{1-4}$ alkylene-$CO_2(C_{1-4}$ alkyl), —$CONHCO_2C_{1-4}$ alkyl, —CONH—$C_{1-4}$ alkylene-NHCO ($C_{1-4}$ alkyl), —CONH—$C_{1-4}$ alkylene-$CONH_2$, —$NHCOC_{1-4}$ alkyl, —$NHCO_2(C_{1-4}$ alkyl), $R^c$, —$CONHR^c$, and —$CO_2R^c$;

$R^4$, at each occurrence, is selected from the group consisting of: H, halo and $C_{1-4}$ alkyl;

$R^5$ is selected from the group consisting of: H, halo, $C_{1-4}$ alkyl substituted with 0-2 $R^b$, $C_{2-4}$ alkenyl substituted with 0-2 $R^b$, $C_{2-4}$ alkynyl substituted with 0-2 $R^b$, —OH, —CN, $NO_2$, —$NH_2$, —$N(C_{1-4}$ alkyl)$_2$, —$O(C_{1-4}$ alkyl), —OCO ($C_{1-4}$ alkyl), —O—$C_{1-4}$ alkylene-O($C_{1-4}$ alkyl), —O—$C_{1-4}$ alkylene-$N(C_{1-4}$ alkyl)$_2$, —$CO_2H$, —$CO_2(C_{1-4}$ alkyl), —$CONH_2$, —$(CH_2)_2CONH_2$, —$CONR^9(C_{1-4}$ alkyl), —$CON(C_{1-4}$ alkyl)$_2$, —$CONR^9$—$C_{1-4}$ alkylene-O($C_{1-4}$ alkyl), —$CONR^9$—$C_{1-4}$ alkylene-$N(C_{1-4}$ alkyl)$_2$, —$CONR^9$—$C_{1-4}$ alkylene-$CO_2(C_{1-4}$ alkyl), —$NR^9COC_{1-4}$ alkyl, —$NR^9CO_2C_{1-4}$ alkyl, —$NR^9CONH(C_{1-4}$ alkyl), —$NR^9CONR^9$—$C_{1-4}$ alkylene-$CO_2C_{1-4}$ alkyl, —$NR^9$—$C_{1-4}$ alkylene-$N(C_{1-4}$ alkyl)$_2$, —$NR^9SO_2(C_{1-4}$ alkyl), —$SO_2NH_2$, $R^8$, —$OR^8$, —$COR^8$, —$CO_2R^8$, —$CONR^9R^8$, —$NR^9COR^8$, —$NR^9CO_2R^8$, and —$NR^9CONR^9R^8$;

$R^6$ is, independently at each occurrence, selected from the group consisting of: H, $C_{1-4}$ alkyl, $COC_{1-4}$ alkyl, $CO_2C_{1-4}$ alkyl, $CO_2Bn$, —CONH—$C_{1-4}$ alkylene-$CO_2C_{1-4}$ alkyl, phenyl, and benzyl;

$R^7$, at each occurrence, is selected from the group consisting of: H, $C_{1-4}$ alkyl, $COC_{1-4}$ alkyl, $CO_2(C_{1-4}$ alkyl), $CO_2Bn$, —CONH—$C_{1-4}$ alkylene-$CO_2C_{1-4}$ alkyl, phenyl, benzyl, and —$CO_2$—$C_{1-4}$ alkylene-aryl;

$R^8$, at each occurrence, is selected from the group consisting of: —$(CH_2)_n$—$C_{3-10}$ carbocycle and —$(CH_2)_n$-5- to 10-membered heterocycle containing carbon atoms and 1-4 heteroatoms selected from the group consisting of: N, $NR^a$, O, and $S(O)_p$; wherein said carbocycle or heterocycle is substituted with 0-3 $R^b$;

$R^9$, at each occurrence, is selected from the group consisting of: H and $C_{1-4}$alkyl;

$R^{10}$, at each occurrence, is selected from the group consisting of: H, halo, OH, and $C_{1-4}$ alkyl;

$R^a$ is selected from the group consisting of: H, $C_{1-4}$ alkyl, —$(CH_2)_n$OH, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$;

$R^b$ is selected from the group consisting of: =O, halo, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —CONH—$C_{1-4}$ alkylene-O($C_{1-4}$ alkyl), —CONH—$C_{1-4}$ alkylene-$N(C_{1-4}$ alkyl)$_2$, —CONH—$C_{1-4}$ alkylene-$N^+(C_{1-4}$ alkyl)$_2$-$C_{1-4}$ alkylene-O—P(O)(OH)$_2$, —$NHCO_2(C_{1-4}$ alkyl), —$R^c$, $COR^c$, $CO_2R^c$, and $CONHR^c$;

$R^c$ is, independently at each occurrence, selected from the group consisting of: —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), $N(CO_2C_{1-4}$ alkyl), O, and $S(O)_p$; wherein each ring moiety is substituted with 0-2 $R^d$;

$R^d$ is selected from the group consisting of: =O, halo, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is selected from 0, 1, 2, 3, and 4; and p, at each occurrence, is selected from 0, 1, and 2.

In a second aspect, the present invention provides compounds of Formula (II)

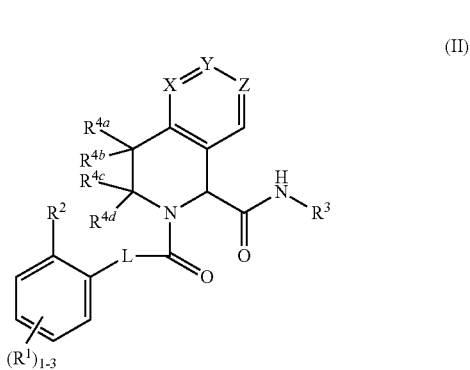

or stereoisomers, tautomers, pharmaceutically acceptable salts thereof, within the scope of the first aspect, wherein:

L is selected from the group consisting of: a bond, —CHR$^{10}$CHR$^{10}$—, —CR$^{10}$=CR$^{10}$—, and —C≡C—;

X, Y, and Z are independently selected from the group consisting of: N and CR$^5$; provided one of X, Y, and Z is N;

R$^1$, at each occurrence, is selected from the group consisting of: H, halo, C$_{1-2}$ alkyl, —O(C$_{1-4}$ alkyl), and —C(=NH)NH$_2$;

R$^{4a}$, R$^{4b}$, R$^{4c}$, and R$^{4d}$ are independently selected from the group consisting of: H, F, and C$_{1-4}$ alkyl;

R$^5$ is selected from the group consisting of: H, halo, NO$_2$, —NH$_2$, —NR$^9$COC$_{1-4}$ alkyl, —NR$^9$CO$_2$C$_{1-4}$ alkyl, —NR$^9$CONH(C$_{1-4}$ alkyl), —NR$^9$—C$_{1-4}$ alkylene-N(C$_{1-4}$ alkyl)$_2$, R$^8$, —NR$^9$COR$^8$, —NR$^9$CO$_2$R$^8$, and —NR$^9$CONR$^9$R$^8$;

R$^8$ is, independently at each occurrence, selected from the group consisting of: —(CH$_2$)$_n$—C$_{3-6}$ cycloalkyl, —(CH$_2$)$_n$-phenyl and —(CH$_2$)$_n$-5-to 10-membered heterocycle containing carbon atoms and 1-4 heteroatoms selected from the group consisting of N, NH, N(C$_{1-4}$ alkyl), O, and S; wherein said cycloalkyl, phenyl, or heterocycle is substituted with 0-3 R$^b$;

R$^b$ is selected from the group consisting of: =O, halo, C$_{1-4}$ alkoxy, and CONH$_2$; and n, at each occurrence, is selected from 0, 1, 2, and 3.

In a third aspect, the present invention includes compounds of Formula (III):

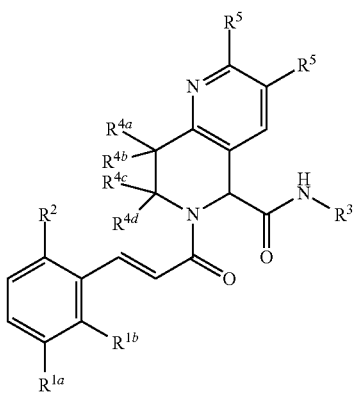

(III)

or stereoisomers, tautomers, pharmaceutically acceptable salts, or solvates thereof, within the scope of the second aspect, wherein:

R$^{1a}$ is selected from the group consisting of: H, halo, C$_{1-2}$ alkyl, and methoxy;

R$^{1b}$ is selected from the group consisting of: H and halo;

R$^2$ is selected from the group consisting of: H, F, CN, OH, C$_{1-4}$ alkoxy, —CHF$_2$, —CF$_3$, —CH$_2$NH$_2$, —OCHF$_2$, —CO(C$_{1-4}$ alkyl), —CONH$_2$, —COOH, triazole substituted with R$^{2a}$, and tetrazole substituted with R$^{2a}$;

R$^3$ is selected from the group consisting of: phenyl substituted with 0-3 R$^{3a}$, and 5- to 10-membered heterocycle containing carbon atoms and 1-4 heteroatoms selected from the group consisting of N, NR$^7$, O, and S(O)$_p$; wherein said heterocycle is substituted with 0-3 R$^{3a}$;

R$^{3a}$ is, independently at each occurrence, selected from the group consisting of: =O, F, Cl, C$_{1-4}$ alkyl, —OH, —O(C$_{1-4}$ alkyl), —CN, —NH$_2$, —CO$_2$H, —CO$_2$(C$_{1-4}$ alkyl), —CONHCO$_2$(C$_{1-4}$ alkyl), —NHCOC$_{1-4}$ alkyl, —(CH$_2$)$_n$NHCO$_2$(C$_{1-4}$ alkyl), and R$^c$;

R$^5$ is selected from the group consisting of: H, F, Cl, Br, NO$_2$, —NH$_2$, —NR$^9$COC$_{1-4}$ alkyl, —NR$^9$CO$_2$C$_{1-4}$ alkyl, —NR$^9$CONH(C$_{1-4}$ alkyl), —NR$^9$—C$_{1-4}$ alkylene-N(C$_{1-4}$ alkyl)$_2$, R$^8$, —NR$^9$COR$^8$, —NR$^9$CO$_2$R$^8$, and —NR$^9$CONR$^9$R$^8$;

R$^8$ is, independently at each occurrence, selected from the group consisting of: —(CH$_2$)$_n$—C$_{3-6}$ cycloalkyl, and —(CH$_2$)$_n$-phenyl, wherein said cycloalkyl or phenyl is substituted with 0-3 R$^b$;

R$^9$ is, independently at each occurrence, selected from the group consisting of: H and C$_{1-4}$alkyl;

R$^b$ is selected from the group consisting of: halo and C$_{1-4}$ alkoxy; and n, at each occurrence, is selected from 0, 1, and 2.

In a fourth aspect, the present invention includes compounds of Formula (IV),

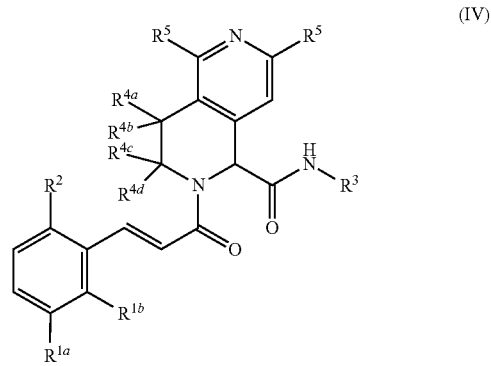

(IV)

or stereoisomers, tautomers, pharmaceutically acceptable salts, or solvates thereof, within the scope of the second aspect, wherein:

R$^{1a}$ is selected from the group consisting of: H, halo, C$_{1-2}$ alkyl, and methoxy;

R$^{1b}$ is selected from the group consisting of: H and halo;

R$^2$ is selected from the group consisting of: H, F, CN, OH, C$_{1-4}$ alkoxy, —CHF$_2$, —CF$_3$, —CH$_2$NH$_2$, —OCHF$_2$, —CO(C$_{1-4}$ alkyl), —CONH$_2$, —COOH, triazole substituted with R$^{2a}$, and tetrazole substituted with R$^{2a}$;

R$^3$ is selected from the group consisting of: phenyl substituted with 1-2 R$^{3a}$, cyclohexyl substituted with 1-3 R$^{3a}$,

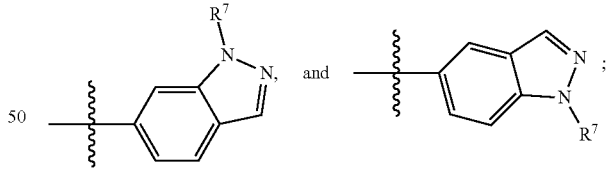

R$^{3a}$ is, independently at each occurrence, selected from the group consisting of: =O, F, Cl, C$_{1-4}$ alkyl, —OH, —O(C$_{1-4}$ alkyl), —CN, —NH$_2$, —CO$_2$H, —CO$_2$(C$_{1-4}$ alkyl), —CONHCO$_2$(C$_{1-4}$ alkyl), —NHCOC$_{1-4}$ alkyl, —(CH$_2$)$_n$NHCO$_2$(C$_{1-4}$ alkyl), and R$^c$;

R$^5$ is selected from the group consisting of: H, halo, NO$_2$, —NH$_2$, —NHCOC$_{1-4}$ alkyl, —NHCO$_2$C$_{1-4}$ alkyl, —NHCONH(C$_{1-4}$ alkyl), —NR$^9$—(CH$_2$)$_2$—N(C$_{1-4}$ alkyl)$_2$, and R$^8$;

R$^8$ is selected from the group consisting of: phenyl and 5- to 10-membered heterocycle containing carbon atoms and 1-4 heteroatoms selected from the group consisting of N, NR$^a$, O, and S; wherein said phenyl or heterocycle is substituted with 0-3 R$^b$;

R$^a$ is H or C$_{1-4}$ alkyl;
R$^b$ is selected from the group consisting of: =O, halo, C$_{1-4}$ alkoxy, and CONH$_2$.

In a fifth aspect, the present invention includes compounds of Formula (V):

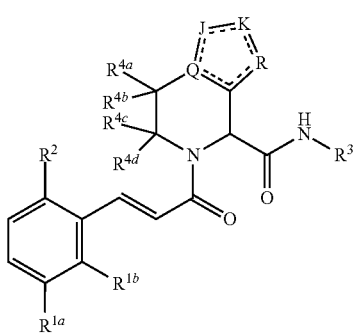

(V)

or stereoisomers, tautomers, pharmaceutically acceptable salts, or solvates thereof, within the scope of the first aspect, wherein:

---- is an optional bond;

Q is selected from the group consisting of: C and N; provided when Q is N, one of the optional bonds attached to Q is absent;

J, K, and R are independently selected from the group consisting of: N, NR$^6$ CHR$^5$, and CR$^5$;

R$^{1a}$ is selected from the group consisting of: H, halo, C$_{1-2}$ alkyl, and methoxy;

R$^{1b}$ is selected from the group consisting of: H and halo;

R$^2$ is selected from the group consisting of: H, F, CN, OH, C$_{1-4}$ alkoxy, —CHF$_2$, —CF$_3$, —CH$_2$NH$_2$, —OCHF$_2$, —CO(C$_{1-4}$ alkyl), —CONH$_2$, —COOH, triazole substituted with R$^{2a}$, and tetrazole substituted with R$^{2a}$;

R$^3$ is selected from the group consisting of: C$_{1-6}$ alkyl substituted with 1-3 R$^{3a}$, C$_{3-10}$ carbocycle substituted with 1-3 R$^{3a}$, and 5-10 membered heterocycle containing carbon atoms and 1-4 heteroatoms selected from the group consisting of N, NR$^7$, O, and S(O)$_p$; wherein said heterocycle is substituted with 1-3 R$^{3a}$;

R$^{3a}$, at each occurrence, is selected from the group consisting of: =O, halo, C$_{1-4}$ alkyl, —OH, —O(C$_{1-4}$ alkyl), —CN, —NH$_2$, —CO$_2$H, —CO$_2$(C$_{1-4}$ alkyl), —CONHCO$_2$(C$_{1-4}$ alkyl), —NHCOC$_{1-4}$ alkyl, —(CH$_2$)$_n$NHCO$_2$(C$_{1-4}$ alkyl), and R$^c$;

R$^5$ is selected from the group consisting of: H, C$_{1-4}$ alkyl, halo, NO$_2$, —NH$_2$, —NR$^9$COC$_{1-4}$ alkyl, —NR$^9$CO$_2$C$_{1-4}$ alkyl, —NR$^9$CONH(C$_{1-4}$ alkyl), —NR$^9$—C$_{1-4}$ alkylene-N(C$_{1-4}$ alkyl)$_2$, R$^8$, —NR$^9$COR$^8$, —NR$^9$CO$_2$R$^8$, and —NR$^9$CONR$^9$R$^8$;

R$^6$ is, independently at each occurrence, selected from the group consisting of: H, C$_{1-4}$ alkyl, COC$_{1-4}$ alkyl, CO$_2$C$_{1-4}$ alkyl, CO$_2$Bn, phenyl, and benzyl;

R$^7$, at each occurrence, is selected from the group consisting of: H and C$_{1-4}$ alkyl;

R$^8$ is, independently at each occurrence, selected from the group consisting of: —(CH$_2$)$_n$—C$_{3-6}$ cycloalkyl, —(CH$_2$)$_n$-phenyl and —(CH$_2$)$_n$-5- to 10-membered heterocycle containing carbon atoms and 1-4 heteroatoms selected from the group consisting of N, NR$^a$, O, and S(O)$_p$; wherein said carbocycle or heterocycle is substituted with 0-3 R$^b$ R$^a$ is selected from the group consisting of: H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$;

R$^b$ is selected from the group consisting of: =O, halo, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N$^+$(C$_{1-4}$ alkyl)$_2$-C$_{1-4}$ alkylene-O—P(O)(OH)$_2$, —NHCO$_2$(C$_{1-4}$ alkyl), —(CH$_2$)$_n$—R$^c$, COR$^c$, CO$_2$R$^c$, and CONHR$^c$;

R$^c$ is, independently at each occurrence, selected from the group consisting of: —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of N, NH, N(C$_{1-4}$ alkyl), N(CO$_2$C$_{1-4}$ alkyl), O, and S(O)$_p$; wherein each ring moiety is substituted with 0-2 R$^d$;

R$^d$ is selected from the group consisting of: =O, halo, —OH, C$_{1-4}$ alkyl, N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of N, NH, N(C$_{1-4}$ alkyl), O, and S(O)$_p$;

n, at each occurrence, is selected from 0, 1, 2, 3, and 4; and p, at each occurrence, is selected from 0, 1, and 2.

In a sixth aspect, the present invention includes compounds of Formulae (VIa) and (VIb):

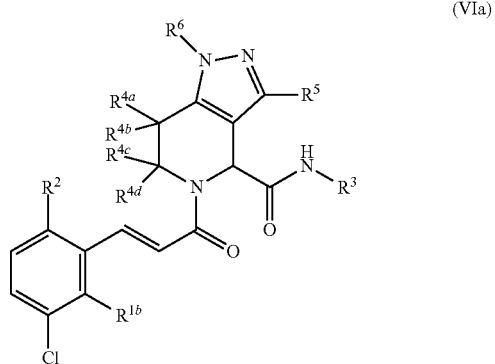

(VIa)

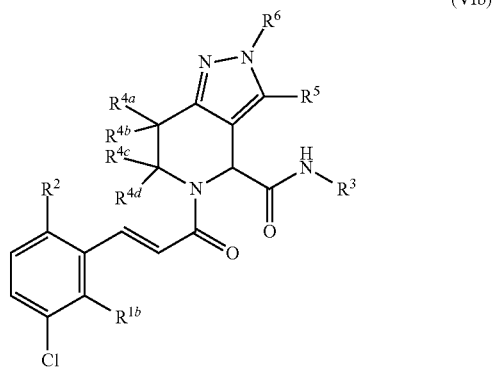

(VIb)

or stereoisomers, tautomers, pharmaceutically acceptable salts, or solvates thereof, within the scope of the fifth aspect, wherein:

R$^{1b}$ is H and F;

R$^2$ is independently selected from the group consisting of: H, F, CF$_3$, C(O)Me, and tetrazole;

R$^3$ is independently selected from the group consisting of: phenyl substituted with 1-2 R$^{3a}$,

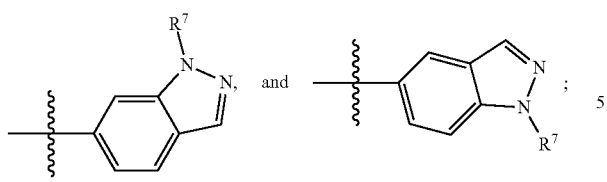

R³ᵃ is, independently at each occurrence, selected from the group consisting of: =O, F, Cl, $C_{1-4}$ alkyl, —OH, —O($C_{1-4}$ alkyl), —CN, —NH₂, —CO₂H, —CO₂($C_{1-4}$ alkyl), and —NHCOC$_{1-4}$ alkyl;

R⁵ is selected from the group consisting of: H, halo, NO₂, $C_{1-4}$ alkyl, —NH₂, phenyl, and benzyl;

R⁶ is, independently at each occurrence, selected from the group consisting of: H, $C_{1-4}$ alkyl, phenyl, and benzyl.

In a seventh aspect, the present invention includes compounds of Formulae (VIIa) and (VIIb):

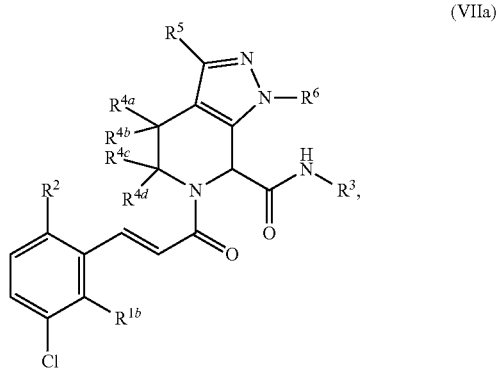

(VIIa)

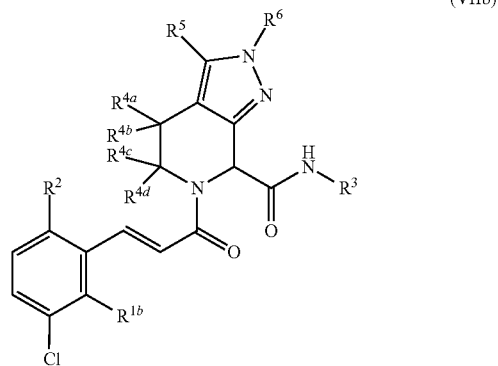

(VIIb)

or stereoisomers, tautomers, pharmaceutically acceptable salts thereof, within the scope of the fifth aspect, wherein:

R$^{1b}$ is H and F;

R² is selected from the group consisting of: H, F, CF₃, C(O)Me, and tetrazole;

R³ is selected from the group consisting of: phenyl substituted with 1-2 R³ᵃ, indazole substituted with 1-2 R³ᵃ, and tetrahydroquinoline substituted with 1-2 R³ᵃ;

R³ᵃ is, independently at each occurrence, selected from the group consisting of: =O, F, Cl, $C_{1-4}$ alkyl, —OH, —O($C_{1-4}$ alkyl), —CN, —NH₂, —CO₂H, —CO₂($C_{1-4}$ alkyl), and —NHCOC$_{1-4}$ alkyl;

R⁵ is selected from the group consisting of: H, halo, NO₂, $C_{1-4}$ alkyl, and —NH₂; and R⁶ is, independently at each occurrence, selected from the group consisting of: H, $C_{1-4}$ alkyl, phenyl, and benzyl.

In an eighth aspect, the present invention includes compounds of Formula (VIII),

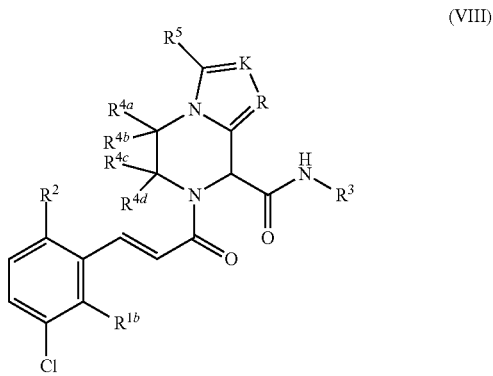

(VIII)

or stereoisomers, tautomers, pharmaceutically acceptable salts, or solvates thereof, within the scope of the sixth aspect, wherein:

K and R are independently selected from the group consisting of: N and CR⁵;

R$^{1b}$ is H or F;

R² is independently selected from the group consisting of: H, F, CF₃, C(O)Me, and tetrazole;

R³ is selected from the group consisting of: phenyl and indazole;

R⁵ is selected from the group consisting of: H and R⁸;

R⁸ is selected from the group consisting of: phenyl and 5- to 10-membered heterocycle containing carbon atoms and 1-4 heteroatoms selected from the group consisting of N, NR$^a$, O, and S; wherein said carbocycle or heterocycle is substituted with 0-3 R$^b$;

R$^a$ is H, or $C_{1-4}$ alkyl; and

R$^b$ is selected from the group consisting of: $C_{1-4}$ alkyl, $C_{1-4}$ alkoxy, and CONH₂.

In a ninth aspect, the present invention provides compounds of Formula (IX):

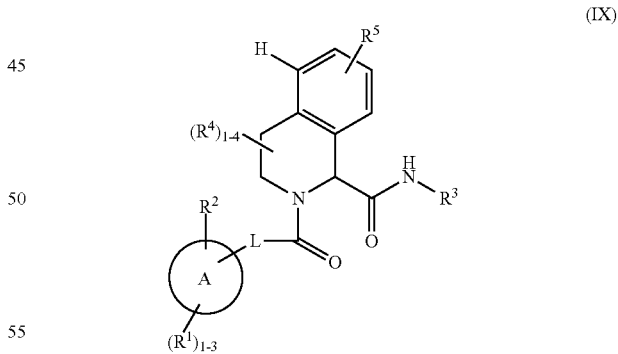

(IX)

or stereoisomers, tautomers, pharmaceutically acceptable salts, or solvates thereof, wherein:

ring A is $C_{3-10}$ carbocycle;

L is selected from the group consisting of: a bond, —CHR¹⁰CHR¹⁰—, —CR¹⁰=CR¹⁰—, and —C≡C—;

R¹, at each occurrence, is selected from the group consisting of: H, halo, $C_{1-2}$ alkyl, —O($C_{1-4}$ alkyl), CN, —CH₂NH₂, and —C(=NH)NH₂;

R² is independently selected from the group consisting of: H, halo, CN, OH $C_{1-6}$ alkyl, $C_{1-4}$ alkoxy, $C_{1-6}$haloalkyl, $C_{1-6}$haloalkoxy, $CO(C_{1-4}$ alkyl), $CONH_2$, $CO_2H$ and a 5- to 7-membered heterocycle comprising carbon atoms and 1-4 heteroatoms selected from N, NH, $N(C_{1-4}$ alkyl), O, and $S(O)_p$, wherein said heterocycle is substituted with 1-2 $R^{2a}$;

$R^{2a}$, at each occurrence, is selected from the group consisting of: H, halo, $C_{1-4}$ alkyl, $CO_2H$, —$CO_2(C_{1-4}$ alkyl), —$CONH_2$, —$CH_2OH$, —$CH_2OC_{1-4}$alkyl, and —$CH_2NH_2$;

$R^3$ is selected from the group consisting of: $C_{1-6}$ alkyl substituted with 1-3 $R^{3a}$, $C_{3-10}$ carbocycle substituted with 1-3 $R^{3a}$, and 5-10 membered heterocycle containing carbon atoms and 1-4 heteroatoms selected from the group consisting of N, $NR^7$, O, and $S(O)_p$; wherein said heterocycle is substituted with 1-3 $R^{3a}$;

$R^{3a}$, at each occurrence, is selected from the group consisting of: H, halo, $C_{1-4}$ alkyl, —OH, $C_{1-4}$ alkoxy, —CN, —$NH_2$, —$NH(C_{1-4}$ alkyl), —$N(C_{1-4}$ alkyl$)_2$, —$CO_2H$, —$CH_2CO_2H$, —$CO_2(C_{1-4}$ alkyl), —$CO_2$—$C_{1-4}$ alkylene-O $(C_{1-4}$ alkyl), —$CO_2$—$C_{1-4}$ alkylene-N$(C_{1-4}$ alkyl$)_2$, —$CO_2$—$C_{1-4}$ alkylene-O—$C_{1-4}$ alkylene-N$(C_{1-4}$ alkyl$)_2$, —$CO_2$—$C_{1-4}$ alkylene-O—$C_{1-4}$ alkylene-O$(C_{1-4}$ alkyl), —$CONH_2$, —$CONH(C_{1-6}$ alkyl), —$CON(C_{1-4}$ alkyl$)_2$, —CONH—$C_{1-4}$ alkylene-$CO_2(C_{1-4}$ alkyl), —$CONHCO_2C_{1-4}$ alkyl, —CONH—$C_{1-4}$ alkylene-NHCO $(C_{1-4}$ alkyl), —CONH—$C_{1-4}$ alkylene-$CONH_2$, —$NHCOC_{1-4}$ alkyl, —$NHCO_2(C_{1-4}$ alkyl), $R^c$, —$CONHR^c$, and —$CO_2R^c$;

$R^4$, at each occurrence, is selected from the group consisting of: H, halo, and $C_{1-4}$ alkyl;

$R^5$ is selected from the group consisting of: H, halo, $C_{1-4}$ alkyl substituted with 0-2 $R^b$, $C_{2-4}$ alkenyl substituted with 0-2 $R^b$, —OH, —CN, —$NH_2$, —$N(C_{1-4}$ alkyl$)_2$, —OCO $(C_{1-4}$ alkyl), —O—$C_{1-4}$ alkylene-O$(C_{1-4}$ alkyl), —O—$C_{1-4}$ alkylene-N$(C_{1-4}$ alkyl$)_2$, —$CO_2H$, —$CO_2(C_{1-4}$ alkyl), —$CONH_2$, —$(CH_2)_2CONH_2$, —$CONR^9(C_{1-4}$ alkyl), —$CON(C_{1-4}$ alkyl$)_2$, —$CONR^9$—$C_{1-4}$ alkylene-O$(C_{1-4}$ alkyl), —$CONR^9$—$C_{1-4}$ alkylene-N$(C_{1-4}$ alkyl$)_2$, —$CONR^9$—$C_{1-4}$ alkylene-$CO_2(C_{1-4}$ alkyl), —$NR^9COC_{1-4}$ alkyl, —$NR^9CO_2C_{1-4}$ alkyl, —$NR^9CONH(C_{1-4}$ alkyl), —$NR^9CONR^9$—$C_{1-4}$ alkylene-$CO_2C_{1-4}$ alkyl, —$NR^9$—$C_{1-4}$ alkylene-N$(C_{1-4}$ alkyl$)_2$, —$NR^9SO_2(C_{1-4}$ alkyl), —$S(C_{1-4}$ alkyl), —$SO_2(C_{1-4}$ alkyl), —$SO_2NH_2$, $R^8$, $C_{2-4}$ alkenylene-$R^8$, —$OR^8$, —$COR^8$, $C_{2-4}$ alkenylene-$COR^8$, —$CONR^9R^8$, —$NR^9COR^8$, —$NR^9CO_2R^8$, and —$NR^9CONR^9R^8$;

$R^7$, at each occurrence, is selected from the group consisting of: H, $C_{1-4}$ alkyl, $COC_{1-4}$ alkyl, $CO_2(C_{1-4}$ alkyl), $CO_2Bn$, —CONH—$C_{1-4}$ alkylene-$CO_2C_{1-4}$ alkyl, phenyl, benzyl, and —$CO_2$—$C_{1-4}$ alkylene-aryl;

$R^8$, at each occurrence, is selected from the group consisting of: —$(CH_2)_n$—$C_{3-10}$ carbocycle and —$(CH_2)_n$-5- to 10-membered heterocycle containing carbon atoms and 1-4 heteroatoms selected from the group consisting of: N, $NR^a$, O, and $S(O)_p$; wherein said carbocycle or heterocycle is substituted with 0-3 $R^b$;

$R^9$, at each occurrence, is selected from the group consisting of: H and $C_{1-4}$alkyl;

$R^{10}$, at each occurrence, is selected from the group consisting of: H, halo, OH, and $C_{1-4}$ alkyl;

$R^a$ is selected from the group consisting of: H, $C_{1-4}$ alkyl, —$(CH_2)_nOH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$;

$R^b$ is selected from the group consisting of: =O, halo, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl$)_2$, —CONH—$C_{1-4}$ alkylene-O$(C_{1-4}$ alkyl), —CONH—$C_{1-4}$ alkylene-N$(C_{1-4}$ alkyl$)_2$, —CONH—$C_{1-4}$ alkylene-$N^+(C_{1-4}$ alkyl$)_2$-$C_{1-4}$ alkylene-O—P(O)(OH$)_2$, —$NHCO_2(C_{1-4}$ alkyl), —$R^c$, $COR^c$, $CO_2R^c$, and $CONHR^c$;

$R^c$ is, independently at each occurrence, selected from the group consisting of: —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$ is selected from the group consisting of: =O, halo, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is selected from 0, 1, 2, 3, and 4;

p, at each occurrence, is selected from 0, 1, and 2;

In a tenth aspect, the present invention provides compounds of Formula (X):

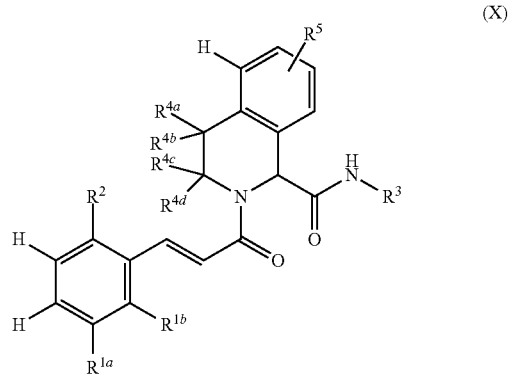

(X)

or stereoisomers, tautomers, pharmaceutically acceptable salts, or solvates thereof, within the scope of the ninth aspect, wherein:

L is selected from the group consisting of: —CH=CH— and —C≡C—;

$R^{1a}$ is selected from the group consisting of: H, halo, $C_{1-2}$ alkyl, and methoxy;

$R^{1b}$ is selected from the group consisting of: H and halo;

$R^2$ is selected from the group consisting of: H, F, CN, OH, $C_{1-4}$ alkoxy, —$CHF_2$, —$CF_3$, —$CH_2NH_2$, —$OCHF_2$, —$CO(C_{1-4}$ alkyl), —$CONH_2$, —COOH, triazole substituted with $R^{2a}$, and tetrazole substituted with $R^{2a}$;

$R^3$ is selected from the group consisting of: phenyl substituted with 1-2 $R^{3a}$, $C_{3-6}$ cycloalkyl substituted with 1-2 $R^{3a}$, pyridyl substituted with 1-2 $R^{3a}$,

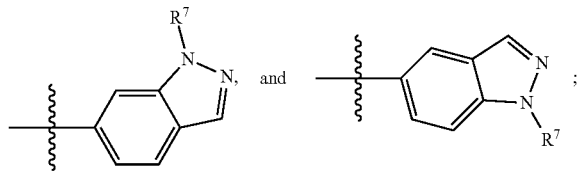

$R^{3a}$, at each occurrence, is selected from the group consisting of: =O, F, Cl, $C_{1-4}$ alkyl, —OH, —O$(C_{1-4}$ alkyl), —CN, —$NH_2$, —$CO_2H$, —$CO_2(C_{1-4}$ alkyl), —$CONHCO_2$ $(C_{1-4}$ alkyl), —$NHCOC_{1-4}$ alkyl, —$(CH_2)_nNHCO_2(C_{1-4}$ alkyl), and $R^c$;

$R^{4a}$, $R^{4b}$, $R^{4c}$, and $R^{4d}$ are independently selected from the group consisting of: H, F, and $C_{1-4}$ alkyl;

$R^5$ is selected from the group consisting of: H, halo, $C_{1-4}$ alkyl —CN, —O($C_{1-4}$ alkyl), —O—$C_{1-4}$ alkylene-O($C_{1-4}$ alkyl), —CO$_2$($C_{1-4}$ alkyl), —OR$^8$, —CONR$^9$R$^8$, and —NR$^9$CO$_2$R$^8$;

$R^8$ is —(CH$_2$)$_n$-phenyl;

$R^c$ is —(CH$_2$)$_n$-5- to 6-membered heterocycle containing carbon atoms and 1-4 heteroatoms selected from the group consisting of N, NH, N(CO$_2$Me), O, and S; and n, at each occurrence, is selected from 0, 1, 2, and 3;

In another embodiment, ring A is phenyl.

In another aspect, ring A is

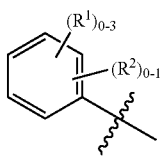

wherein $R^1$ is, independently at each occurrence, selected from the group consisting of: halogen, $C_{1-4}$ alkyl, OH, $C_{1-4}$ alkoxy, CO($C_{1-4}$ alkyl), CN, CH$_2$F, CHF$_2$, OCHF$_2$, and —CH$_2$NHCO$_2$($C_{1-4}$ alkyl), a 5- to 7-membered heterocycle comprising carbon atoms and 1-4 heteroatoms selected from N, NR$^c$, O, and S(O)$_p$, wherein said heterocycle is substituted with 0-2 $R^{2a}$.

In another aspect, ring A is

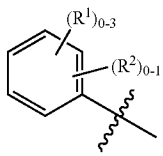

is independently selected from the group consisting of:

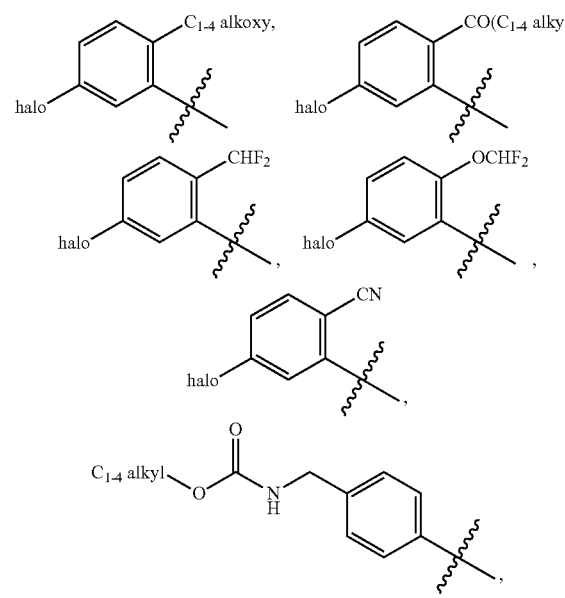

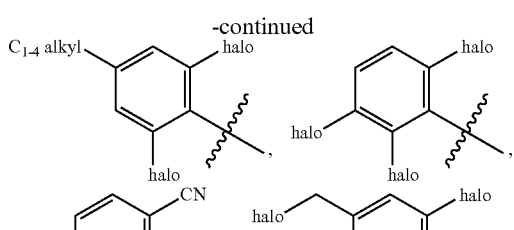

and

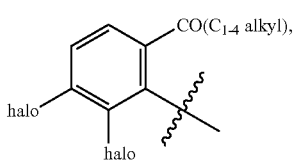

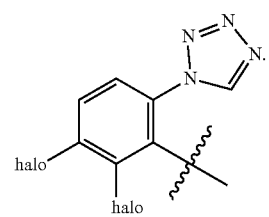

In another embodiment, L is independently selected from the group consisting of: a bond, —CH$_2$CH$_2$—, —CH=CH—, —C(Me)=CH—, —C≡C—, and —CH$_2$NH—.

In another embodiment, L is independently selected from the group consisting of: a bond, —CH$_2$CH$_2$—, —CH=CH—, and —C(Me)=CH.

In another embodiment, L is independently selected from the group consisting of: a bond, —CH$_2$CH$_2$— and —CH=CH—.

In another embodiment, L is —CH=CH—.

In another embodiment, $R^3$ is $C_{1-4}$ alkyl substituted with $R^{3a}$.

In another embodiment, $R^3$ is phenyl substituted with $R^{3a}$.

In another embodiment, $R^3$ is cyclohexyl substituted with $R^{3a}$.

In another embodiment, $R^3$ is a heterocycle substituted with $R^{3a}$ and selected from:

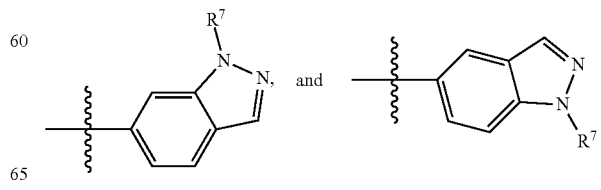

In another embodiment, $R^3$ is

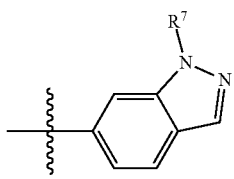

substituted with $R^{3a}$.

In another embodiment, $R^3$ is $C_{1-4}$ alkyl substituted with $R^{3a}$.

In another embodiment, $R^3$ is phenyl substituted with $R^{3a}$.

In another embodiment, $R^3$ is cyclohexyl substituted with $R^{3a}$.

In another embodiment, $R^3$ is a heterocycle substituted with $R^{3a}$ and selected from:

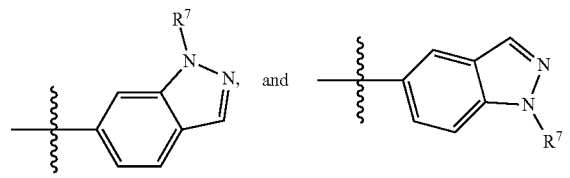

In another embodiment, $R^3$ is

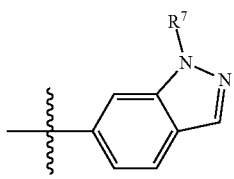

substituted with $R^{3a}$.

In another aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the exemplified examples or a stereoisomer, a tautomer, a pharmaceutically acceptable salt, or a solvate thereof.

In another embodiment, the compounds of the present invention have Factor XIa Ki values ≤10 µM.

In another embodiment, the compounds of the present invention have Factor XIa Ki values ≤1 µM.

In another embodiment, the compounds of the present invention have Factor XIa Ki values ≤0.5 µM.

In another embodiment, the compounds of the present invention have Factor XIa Ki values ≤0.1 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a second factor XIa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R," and "S" are used as described herein for indicating atom configuration(s) relative to a core molecule and are intended to be used as defined in the literature (IUPAC Recommendations 1996, Pure and Applied Chemistry, 68, 2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13th Ed.), Lewis, R. J., ed., J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and Methods in Enzymology, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice*, King, F. D., ed. The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); *The Practice of Medicinal Chemistry*, Wermuth, C. G., ed., Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOC or Boc tert-butoxycarbonyl
BOP reagent benzotriazol-1-yloxytris(dimethylamino)phosphonium hexafluorophosphate
Burgess reagent 1-methoxy-N-triethylammoniosulfonylmethanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m- meta-chloroperbenzoic acid
CPBA
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM Dichloromethane
DEA Diethylamine
Dess-Martin 1,1,1-tris(acetyloxy)-1,1-dihydro-1,2-beniziodoxol-3-(1H)-one
DIC or DIPCDI Diisopropylcarbodiimide
DIEA, DIPEA diisopropylethylamine (Hunig's base)
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-(+)-1,2-bis((2S,5S)-2,5-diethylphospholano)benzene (1,5-EtDuPhosRh(I) cyclooctadiene)rhodium(I) trifluoromethanesulfonate
$Et_3N$ or TEA Triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro(phenylmethylene) (triycyclohexylphosphine)ruthenium
HCl hydrochloric acid
HATU O-(7-azabenzotriazol-1-yl)-N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene
SEM-Cl 2-(trimethysilyl)ethoxymethyl chloride
$SiO_2$ silica oxide
$SnCl_2$ tin(II) chloride TBAI tetra-n-butylammonium iodide
TEA triethylamine
TFA trifluoroacetic acid
THF tetrahydrofuran
TMSCHN$_2$ trimethylsilyldiazomethane
T3P propane phosphonic acid anhydride
TRIS tris (hydroxymethyl) aminomethane The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 3rd Ed., Wiley-Interscience (1999)).

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders which include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis, for example, alterations of the vessel wall, changes in the flow of blood, and alterations in the composition of the vascular compartment. These risk factors are collectively known as Virchow's triad. (*Hemostasis and Thrombosis, Basic Principles and Clinical Practice*, 5th Ed., p. 853, Colman, R. W. et al., eds., Lippincott Williams & Wilkins (2006))

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy) are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood,* 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood,* 108:192-199 (2006)). Contact activation is a surface mediated process responsible in part for the regulation of thrombosis and inflammation, and is mediated, at least in part, by fibrinolytic, complement, kininogen/kinin, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J Exp. Med.*, 202:271-281 (2005); Kleinschmitz et al., *J Exp. Med.*, 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.*, 10:198-204 (2000))

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001)). Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, factor XI deficiency rescues the perinatal lethal phenotype of complete protein C deficiency (Chan et al., *Amer. J. Pathology*, 158:469-479 (2001)). Furthermore, baboon cross-reactive, function blocking antibodies to human factor XI protect against baboon arterial—venous shunt thrombosis (Gruber et al., *Blood*, 102:953-955 (2003)). Evidence for an antithrombotic effect of small molecule inhibitors of factor XIa is also disclosed in published U.S. Patent Application No. 2004/0180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or post-traumatic, but rarely spontaneous hemorrhage. Postoperative bleeding occurs mostly in tissue with high concentrations of endogenous fibrinolytic activity (e.g, oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal 1389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", *Hemostasis and Thrombosis*, pp. 103-122, Lippincott Williams & Wilkins (2001); Schmaier A. H., "Contact Activation", *Thrombosis and Hemorrhage*, pp. 105-128 (1998)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, 2nd Ed., pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility, (i) factors that are ideal for use as a parenteral agent such as solubility profile and pharmacokinetics.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis andHaemostasis*, Vol. 3 (Suppl. 1):P1228 (2005); Schumacher, W. A. et al., *European Journal of Pharmacology*, pp. 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid intema, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J Med.*, 334(11):677-681 (1996); Blom, J. W. et al., *JAMJA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 μM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 μM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (pyroGlu-Pro-Arg-pNA; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 μM and the synthetic substrate S-2302 (H-(D)-Pro-Phe-Arg-pNA; CHROMOGENIX®) at a concentration of 0.00008-0.0004 M. The $K_m$ value used for calculation of $K_i$ was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 μM and the synthetic substrate S-2366 (pyroGlu-Pro-Arg-pNA; CHROMOGENIX®) at a concentration of 0.0002-0.00026 M.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_1$ values:

$$(v_o-v_s)/v_s = I/(K_i(1+S/K_m)) \text{ for a competitive inhibitor with one binding site; or}$$

$$v_s/v_o = A+((B-A)/1+((IC_{50}/(I)_n)));\text{ and}$$

$$K_i = IC_{50}/(1+S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Illinois) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of ≤10 μM (10000 nM) was observed. Table A below lists Factor XIa Ki values measured for the following examples.

TABLE A

| Example No. | Factor XIa Ki (nM) |
| --- | --- |
| 1 | 1737.00 |
| 3 | 10.32 |
| 10 | <5.00 |
| 17 | 2795.00 |
| 23 | <5.00 |
| 28 | <5.00 |
| 32 | 5117.00 |
| 40 | 6732.00 |
| 42 | 886.40 |
| 48 | 7.08 |

TABLE A-continued

| Example No. | Factor XIa Ki (nM) |
|---|---|
| 55 | 171.60 |
| 65 | 23.30 |
| 76 | 565.5 |
| 77 | 5.02 |
| 86 | 51.20 |
| 100 | 258.00 |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-venous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, IL).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Ed. (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an antiarrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil, protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXR beta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles,* 16(1):35-7 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1 illustrates a few approaches to the synthesis of compounds of Formula (I). Amide 1c can be prepared by amide coupling of commercially available or readily accessible acid 1a and readily accessible aniline 1b using methods commonly used in the literature, such as T3P/base, HOAt/EDC/base and/or $POCl_3$, pyridine. Deprotection of the protecting group $PG_1$ using appropriate conditions known to those in the art of organic synthesis, followed by coupling with acid 1e can yield compounds of formula 1g. Alternatively, coupling of amine 1d with acid 1e followed by deprotection can give acid 1f. The coupling of acid 1f with amine 1b under standard peptide coupling procedures can yield compounds of formula 1g. Appropriate functionalization of intermediates used in this invention to prepare compounds of formula 1g can be achieved through the Suzuki, Buchwald, Ullman or Mitsunobu reactions or simple reactions known to those in the art.

Scheme 2 describes an alternative method to access compounds of this invention. Reaction of acid 1e, isocyanide 2a, and imine 2b can give Ugi product 2d (Schuster, I. et al., Letters in Organic Chemistry, 4(2):102-108 (2007)). Selective oxidation of tetrahydroisoquinoline 2c using known methods such as $MnO_2$ (Aoyama, T. et al., Synlett, 1:35-36 (1998)) can yield imine 2b, which can then be used via the three component Ugi coupling procedures described above. The Ugi coupling procedures can be used extensively with other imino derived intermediates contained in this invention. Further manipulations of the Ugi derived products can afford compounds of this invention.

Scheme 2:

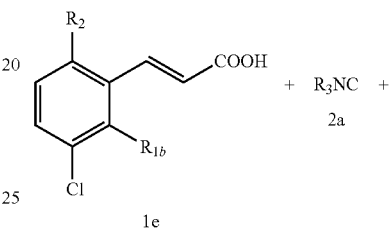

Scheme 1:

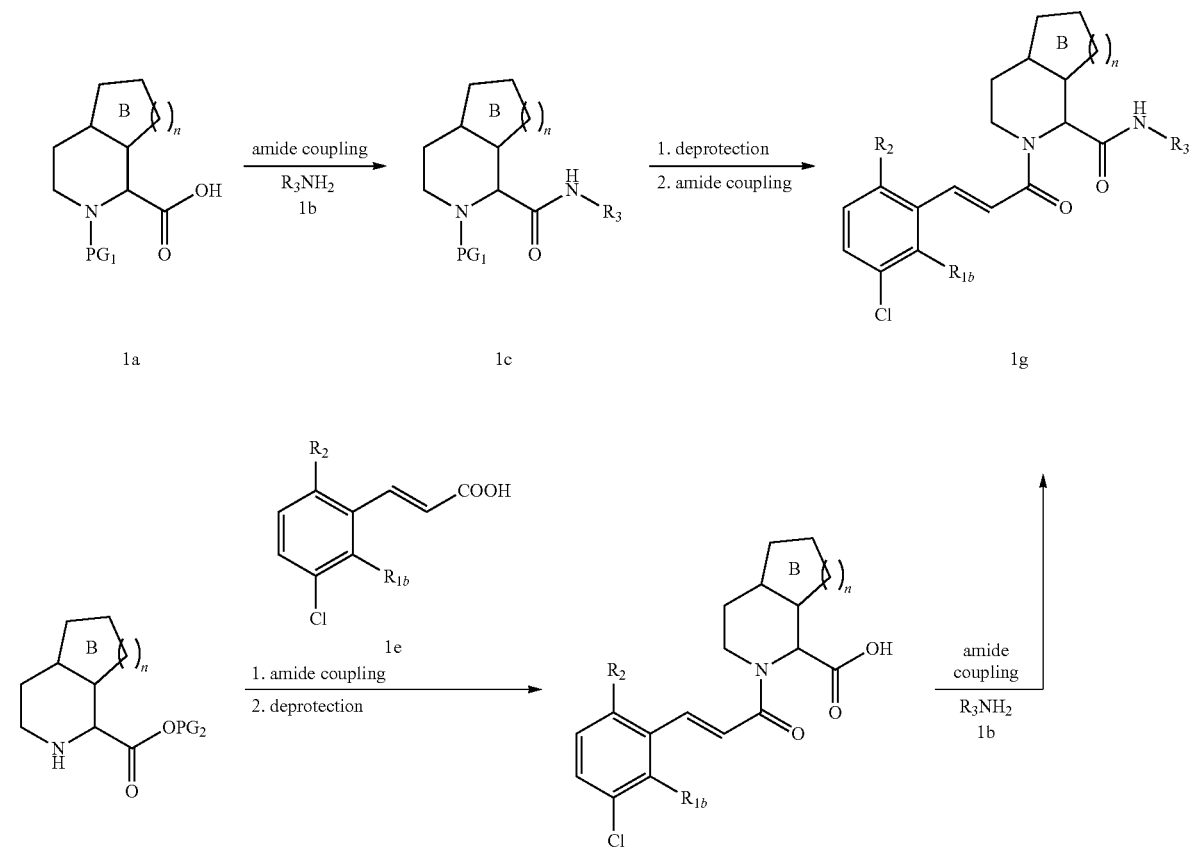

$PG_1$ = H/protecting group

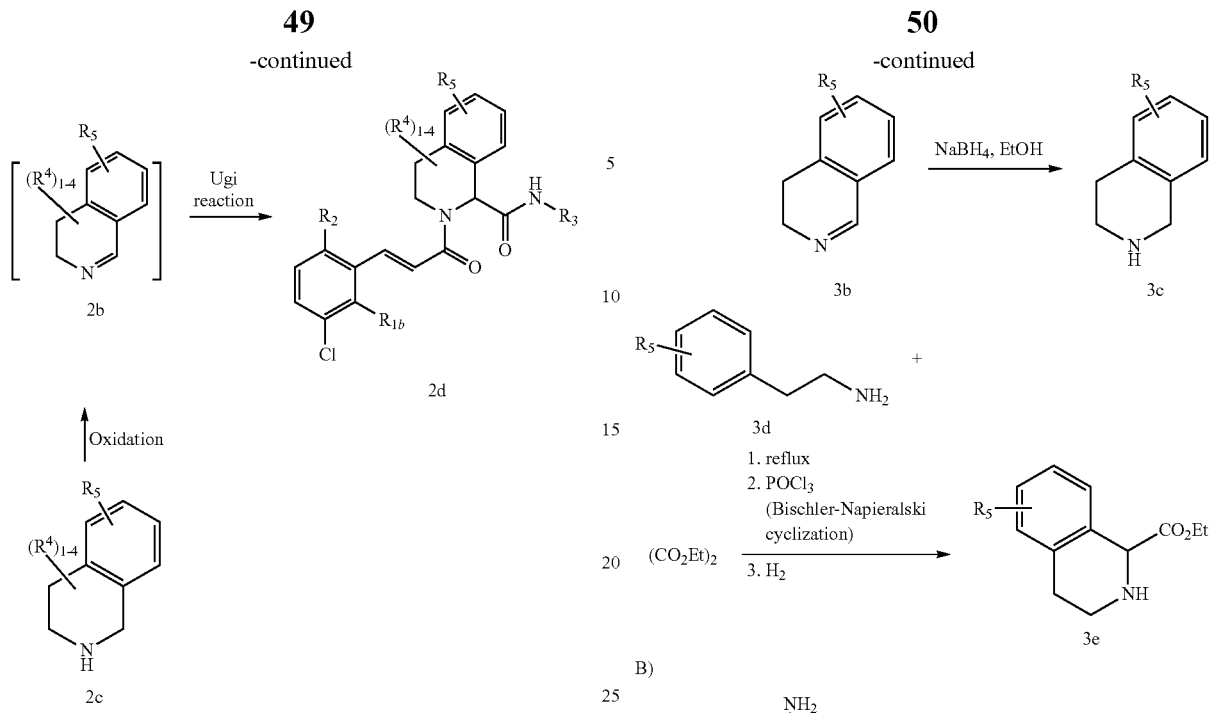

Scheme 3 describes methods for preparing the tetrahydroisoquinoline intermediate 3c and 3e. Method A uses Bischler-Napieralski cyclization to access compounds such as intermediate 3c (Al-Hiari, Y. M. et al., Journal of Heterocyclic Chemistry, 42(4): 647-659 (2005)) or 3e (Zalan, Z. et al., Tetrahedron, 62(12): 2883-2891 (2006)). Method B uses the Friedel-Crafts alkylation reaction to access compounds such as intermediate 3c (Topsom, R. D. et al., Journal of the Chemical Society [Section]D: Chemical Communications, 15:799 (1971)). Alternatively, as described in Method C, cyclization of intermediate 3h and 3-aminopropanol (3i) can afford 3j. Reduction with NaBH$_4$, followed by PCC oxidation gave β-amino aldehyde, which can be converted to 3c under basic conditions (Umetsu, K.; Asao, N., Tetrahedron Letters, 49(17): 2722-2725 (2008)). In Method D, lactam 3l can be synthesized from ketone 3k by the Beckmann rearrangement. Reduction of 3l can afford intermediates such as 3c (Vernier, J. et al., WO 2008024398 (2008)). In Method E, the dihydroisoquinoline carbaldehyde (3m) was converted to 3c under basic conditions (Martin, S. et al., WO 2006134143 (2006)). In Method F, dihydroisoquinolinethione was converted to 3c treating the thione 3o with bromopropene followed by treatment with perchloric acid and sodium borohydride (Mohinder, B, et al., Indian Journal of Chemistry, Section B: Organic Chemistry Including Medicinal Chemistry, 18B (4); 312-15 (1979)).

Scheme 3:

A)

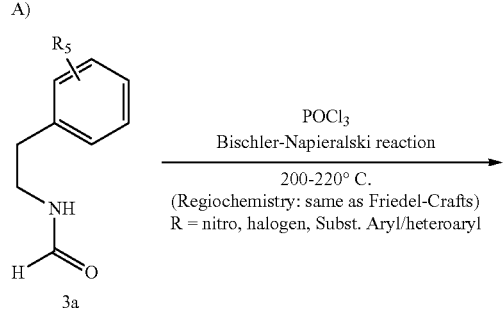

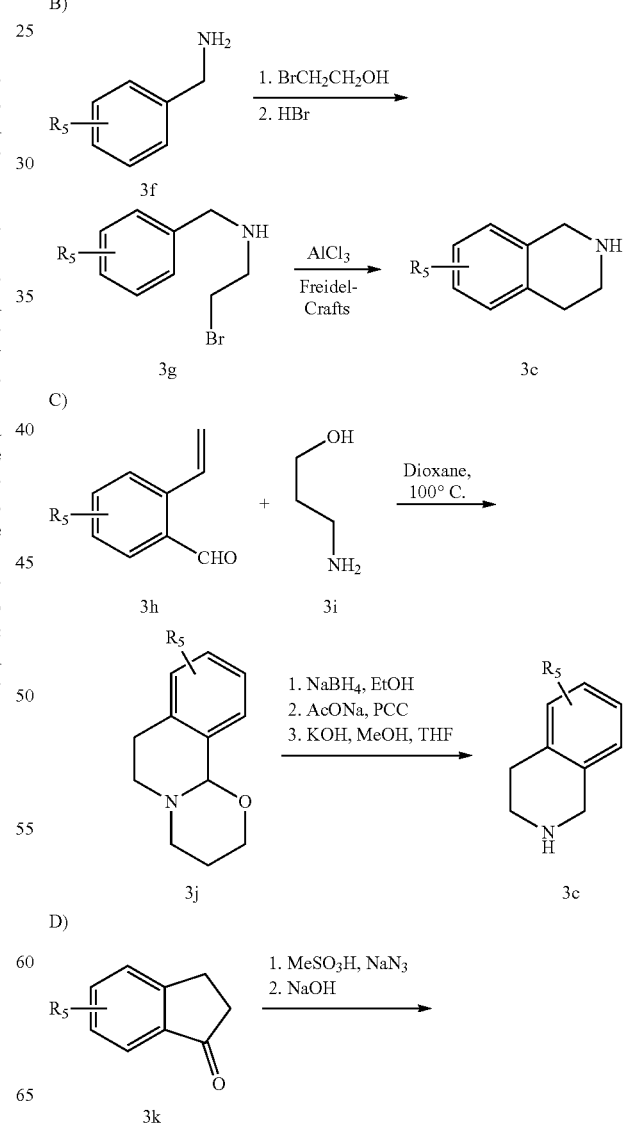

-continued

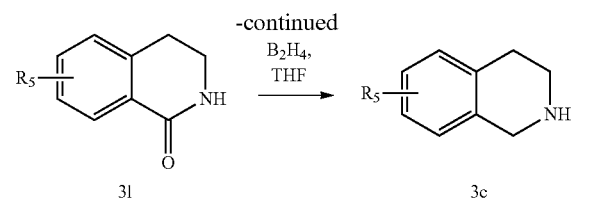

E)

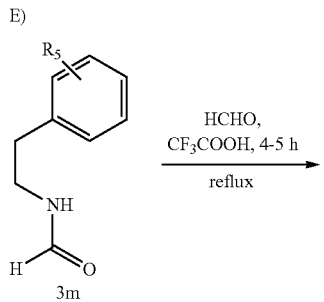

F)

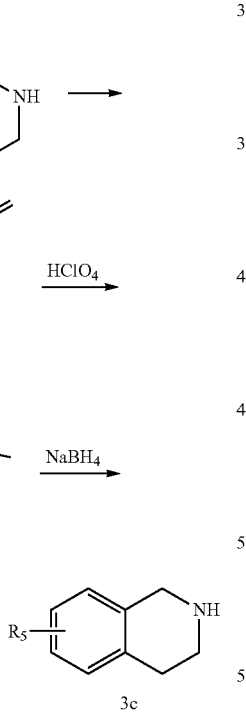

Preparation of substituted THQ analogs is shown in Scheme 4. Bromide 4a can be converted to nitrile 4b under lithiation conditions. Hydrolysis under basic conditions should lead to acid 4c, which can be converted to carbamate 4e via Curtius rearrangement. Formation of the THQ intermediate 4f can then be accomplished by treatment with paraformaldehyde in a mixture of acetic and sulfuric acid (Bigge, C. F. et al, Bioorganic & Medicinal Chemistry Letters, 3(1): 39-42 (1993)). Deprotection of carbamate 4f followed by protection with Boc$_2$O should afford intermediate 4h, which can be subjected to the Suzuki cross coupling reaction with an appropriate boronate or boronic acid or the Stille coupling procedures known to those in the art.

Scheme 4:

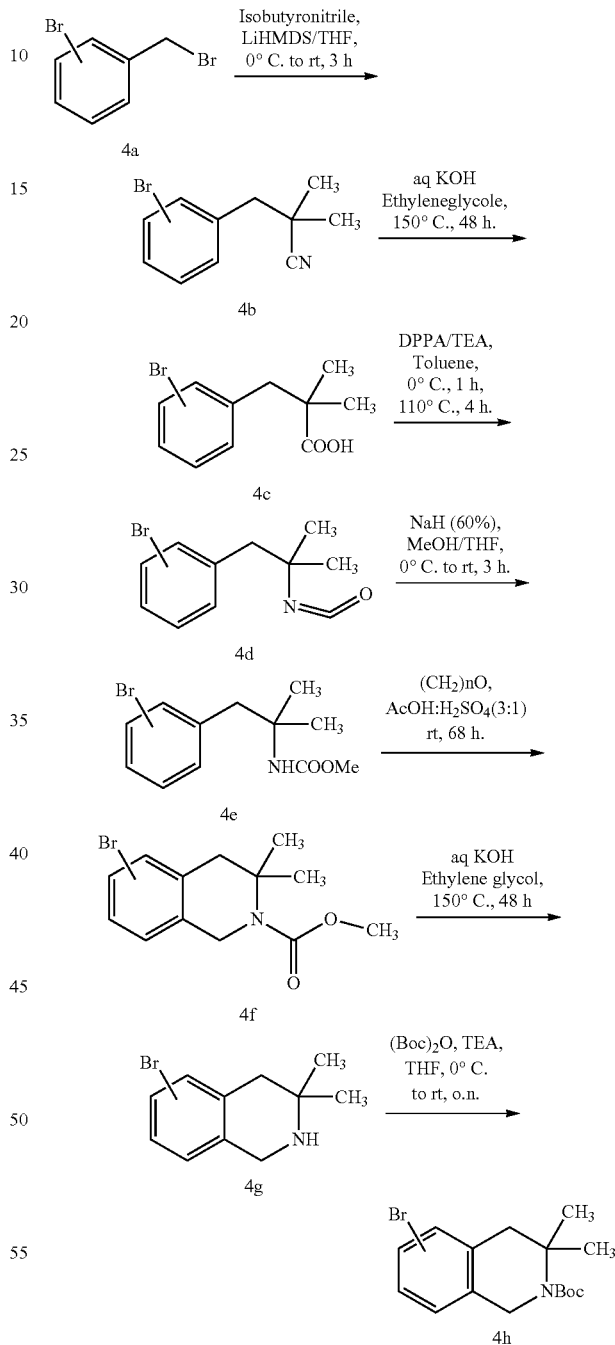

Scheme 5 describes functionalization on intermediates 3c through coupling reactions, such as Suzuki, Buchwald, Ullman or Mitsunobu reactions or substitution reactions when halogen and hydroxyl groups are present on the aromatic ring. Esters or amides 5h can be synthesized from commercially available esters 5f or can be obtained via standard reactions involving organometallic reactions of the halogen with CO₂. Reduction of isoquinoline 5d or 5i using literature conditions, such as H₂/PtO₂ (Schlittler, E.; Muller, J. Helv. Chim. Acta., 31:914-924 (1948)), Na/NH₃ (The Birch reduction of aromatic compounds. Rabideau, P. W. et al., Organic Reactions, 42 (1992)) can yield tetrahydroisoquinolines. Sulfonamide 5l can be accessed through readily available sulfonyl chloride 5i. Sulfones 5k can be prepared through coupling with alkyl halides using conditions such as Zn mediated coupling reactions (Sun, X. et al., Synthetic Communications, 28(10): 1785-1791 (1998)). Alternatively the sulfones can be readily accessed via the oxidation of the thioalkyl derivatives with MCPBA. It should be noted that the same sequence of reactions can easily be adopted for other THQ like compounds where the phenyl is replaced with either a 5 and or 6-membered heterocyclic ring. In these cases appropriate steps known to those in the art of organic synthesis can be taken to prepare intermediate compounds of this invention Scheme 5:

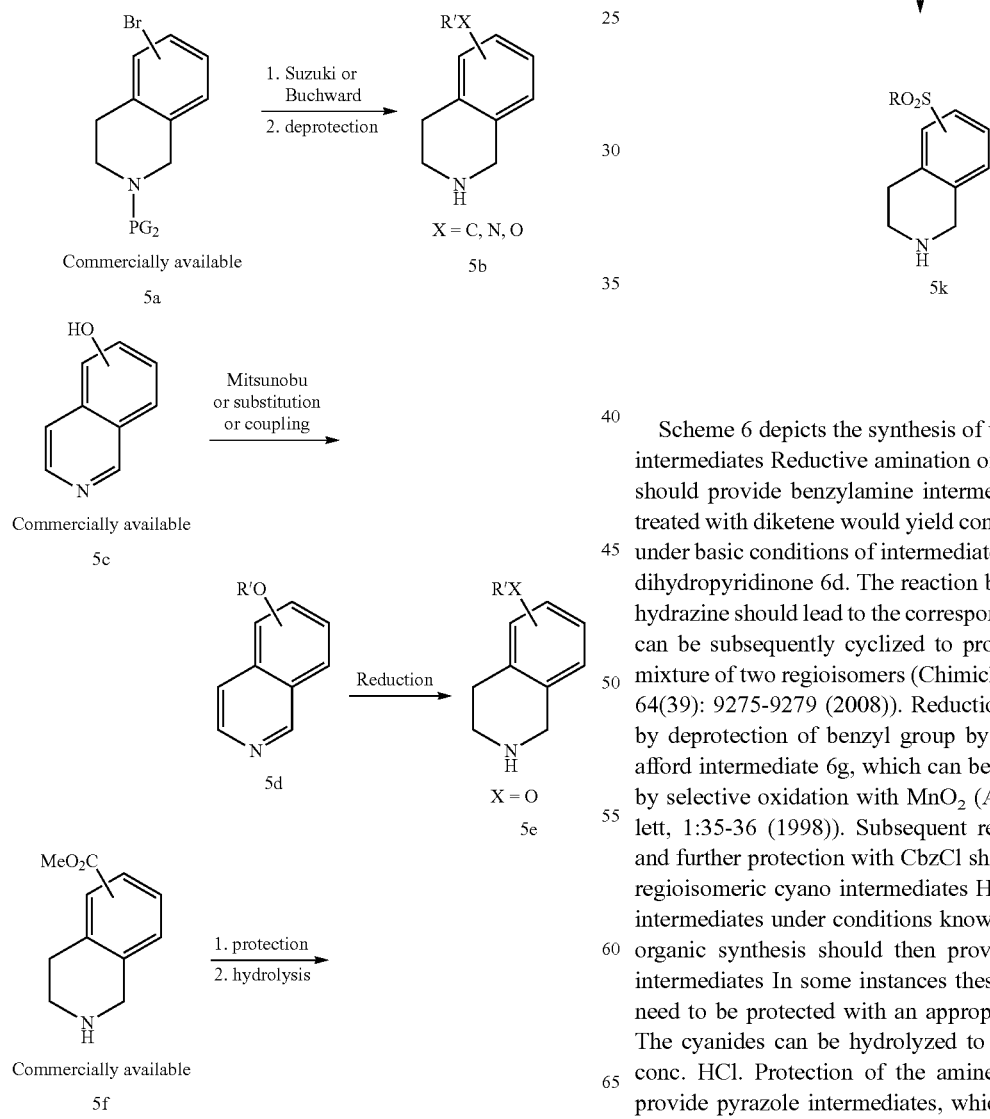

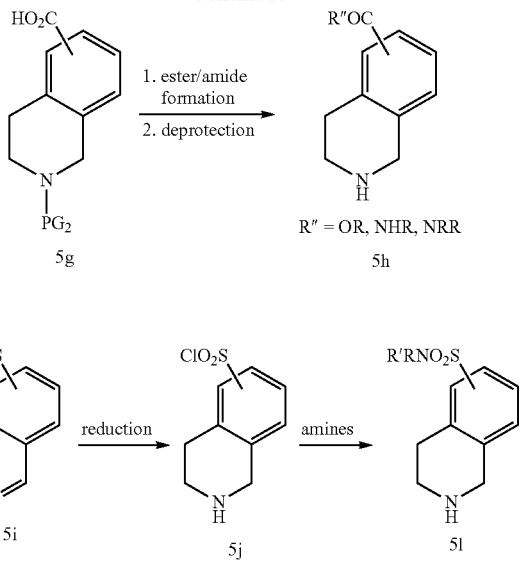

Scheme 6 depicts the synthesis of various pyrazole-based intermediates Reductive amination of the primary amine 6a should provide benzylamine intermediate 6b, which when treated with diketene would yield compound 6c. Cyclization under basic conditions of intermediate 6c should provide the dihydropyridinone 6d. The reaction between 6d and methyl hydrazine should lead to the corresponding hydrazone which can be subsequently cyclized to provide pyrazole 6e as a mixture of two regioisomers (Chimichi, S et al, Tetrahedron, 64(39): 9275-9279 (2008)). Reduction with LAH followed by deprotection of benzyl group by hydrogenation should afford intermediate 6g, which can be converted to imine 6h by selective oxidation with MnO₂ (Aoyama, T. et al., Synlett, 1:35-36 (1998)). Subsequent reactions with TMSCN and further protection with CbzCl should easily provide the regioisomeric cyano intermediates Hydrolysis of the cyano intermediates under conditions known to those in the art of organic synthesis should then provide requisite pyrazole intermediates In some instances these intermediates would need to be protected with an appropriate protecting group. The cyanides can be hydrolyzed to acids 6k and 6l using conc. HCl. Protection of the amines with Boc₂O should provide pyrazole intermediates, which can be used to prepare compounds of this invention as described above.

Scheme 6:

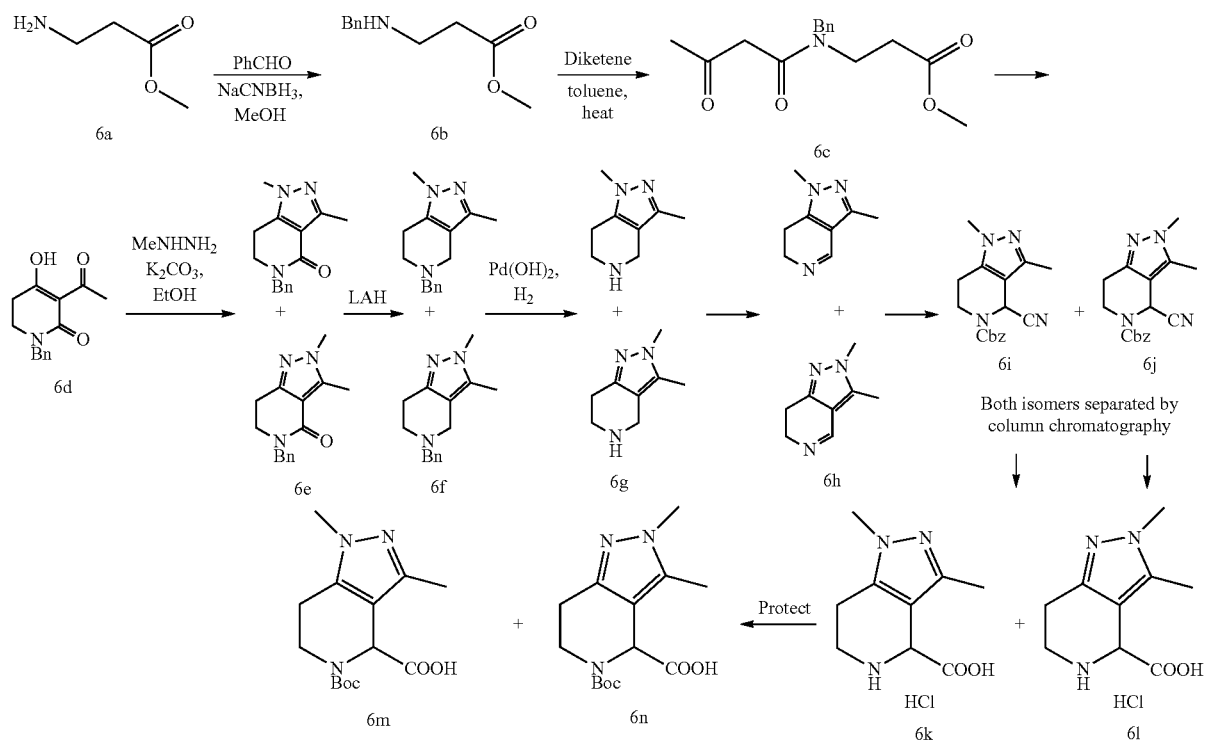

Alternatively, other pyrazole intermediates of this invention can be prepared by the reaction of p-methoxy benzylamine with a readily accessible lactone 7a to afford amide 7b, which then can be reduced to amine 7c by treating with borane-dimethyl sulfide complex, as shown in Scheme 7. Acylation of amine 7c should lead to amide 7d. Oxidation with Dess-Martin reagent should lead to ketone 7e, which can be cyclized under basic conditions to provide dihydropyridinone 7f. The reaction between 7f and methyl hydrazine affords the corresponding hydrazone that can be subsequently cyclized to give a mixture of pyrazoles 7g and 7h (Chimichi, S et al, Tetrahedron, 64(39): 9275-9279 (2008)). Reduction followed by deprotection affords the mixture of tetrahydropyridine 7k and 7l. Selective oxidation of 7k and 7l with $MnO_2$ (Aoyama, T. et al., Synlett, 1:35-36 (1998)) can give the imine mixture of 7m and 7n, which can be converted to compounds of this invention. Additional examples of pyrazole intermediates are also described by Zerovnik Dara et. al. (Synthesis 19, 3363-3373, 2010).

Scheme 7:

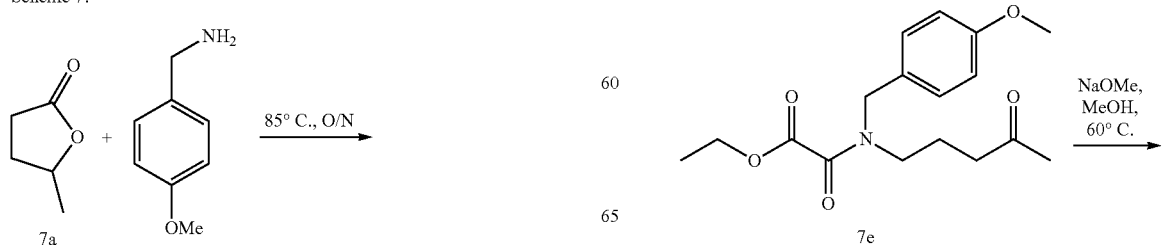

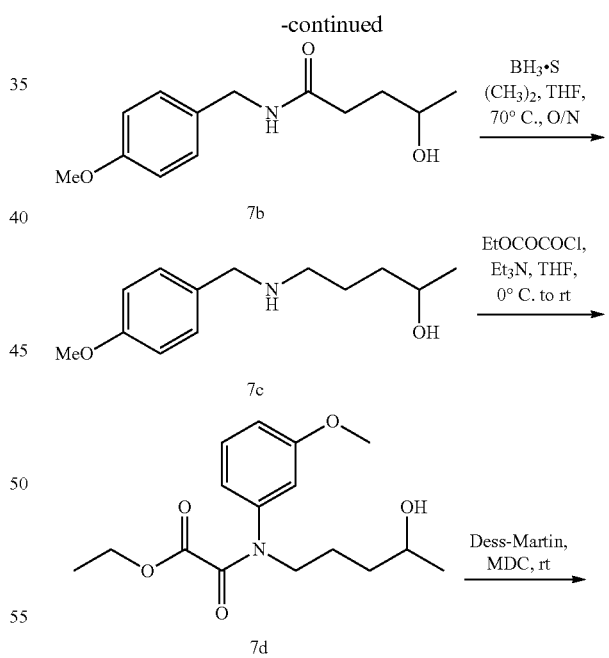

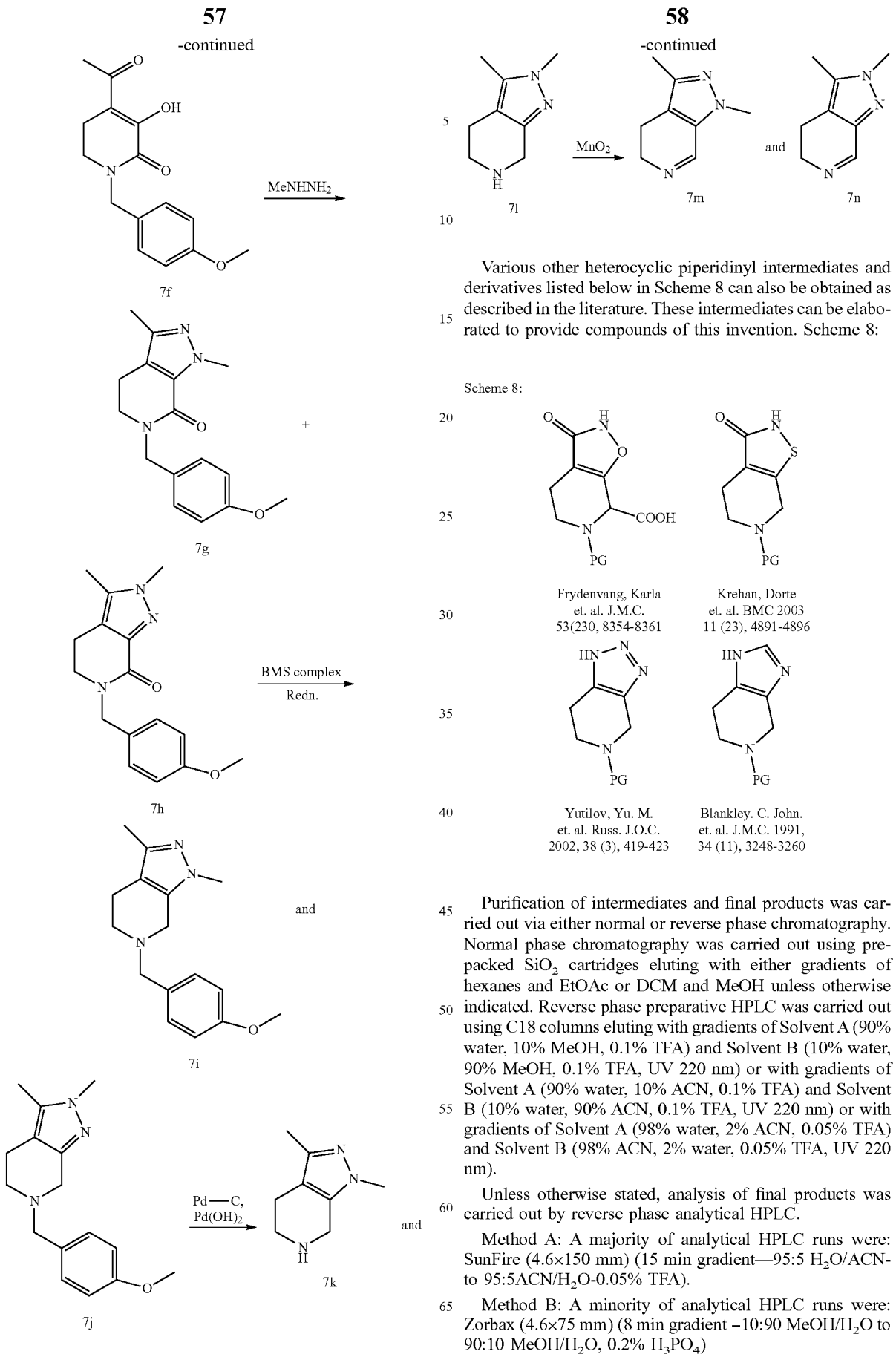

Various other heterocyclic piperidinyl intermediates and derivatives listed below in Scheme 8 can also be obtained as described in the literature. These intermediates can be elaborated to provide compounds of this invention. Scheme 8:

Scheme 8:

Frydenvang, Karla et. al. J.M.C. 53(230, 8354-8361

Krehan, Dorte et. al. BMC 2003 11 (23), 4891-4896

Yutilov, Yu. M. et. al. Russ. J.O.C. 2002, 38 (3), 419-423

Blankley. C. John. et. al. J.M.C. 1991, 34 (11), 3248-3260

Purification of intermediates and final products was carried out via either normal or reverse phase chromatography. Normal phase chromatography was carried out using pre-packed $SiO_2$ cartridges eluting with either gradients of hexanes and EtOAc or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm).

Unless otherwise stated, analysis of final products was carried out by reverse phase analytical HPLC.

Method A: A majority of analytical HPLC runs were: SunFire (4.6×150 mm) (15 min gradient—95:5 $H_2O$/ACN-to 95:5ACN/$H_2O$-0.05% TFA).

Method B: A minority of analytical HPLC runs were: Zorbax (4.6×75 mm) (8 min gradient –10:90 MeOH/$H_2O$ to 90:10 MeOH/$H_2O$, 0.2% $H_3PO_4$)

A majority of mass spectra runs were run using Phenomenex Luna C18 (2×30 mm) (2 min gradient 90% H₂O/10% MeOH/0.1% TFA to 90% MeOH/10% H₂O/0.1% TFA)

Intermediate 1

(E)-2,5-Dioxopyrrolidin-1-yl 3-(5-chloro-2-(1H-tetrazol-1-yl)phenyl)acrylate

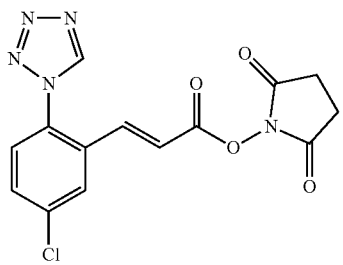 [SMILES: O=C(/C=C/c1cc(Cl)ccc1-n1cnnn1)ON1C(=O)CCC1=O]

The synthesis was described as Intermediate 1 in PCT International Application, WO 2009/114677 published Sep. 17, 2009.

Intermediate 2

(E)-3-(5-chloro-2-tetrazol-1-yl-phenyl)-acrylic acid

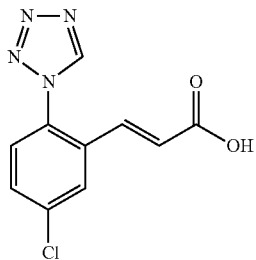 [SMILES: O=C(O)/C=C/c1cc(Cl)ccc1-n1cnnn1]

The synthesis was described as Intermediate 1B in PCT International Application, WO 2009/114677 published Sep. 17, 2009.

Intermediate 3

(E)-3-(3-Chloro-2-fluoro-6-tetrazol-1-yl-phenyl)-acrylic acid 2,5-dioxopyrrolidin-1-yl ester

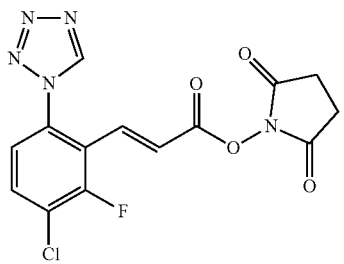 [SMILES: O=C(/C=C/c1c(-n2cnnn2)ccc(Cl)c1F)ON1C(=O)CCC1=O]

Intermediate 3A: (E)-3-(3-chloro-2-fluoro-6-(1H-tetrazol-1-yl)phenyl)acrylic acid: The synthesis of Intermediate 3A was described as Intermediate 7 in PCT International Application, WO 2009/114677 published Sep. 17, 2009.

Intermediate 3: To a slightly turbid mixture of Intermediate 3A (1.0 g, 3.72 mmol) in THF (18.70 mL) and DMF (1.870 mL) was added 1-hydroxypyrrolidine-2,5-dione (0.471 g, 4.09 mmol) and DIC (0.638 mL, 4.09 mmol). The reaction was stirred at rt and a white precipitate formed overtime. The solid was collected by suction filtration and washed with MeOH and H₂O. The solid was then, dried under vacuum to give Intermediate 3 (0.98 g, 72%), as a white solid. ¹H NMR (500 MHz, DMSO-d₆) δ 9.92 (s, 1H), 8.06 (t, J=8.12 Hz, 1H), 7.72 (d, J=8.80 Hz, 1H), 7.36 (d, J=16.23 Hz, 1H), 6.81 (d, J=16.51 Hz, 1H), 2.84 (s, 4 H) ppm. MS (ESI) m/z: 366.2 (M+H)⁺.

Intermediate 4

(E)-3-(2-acetyl-5-chlorophenyl)acrylic acid

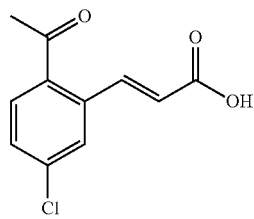

Intermediate 4A: (E)-tert-butyl 3-(2-acetyl-5-chlorophenyl)acrylate: To a degassed solution of 1-(2-bromo-4-chlorophenyl)ethanone (1.0 g, 4.28 mmol), tributylamine (2.041 mL, 8.57 mmol), and tert-butyl acrylate (1.255 mL, 8.57 mmol) in DMF (10 mL) was added palladium on carbon (0.456 g, 0.428 mmol) and Pd(OAc)₂ (0.096 g, 0.428 mmol). The reaction mixture was warmed to 100° C. After 16 h, the reaction was cooled to rt. The reaction was filtered and the solid was rinsed with DMF. The filtrate was diluted with EtOAc, washed with H₂O (2×), brine, dried over Na₂SO₄, filtered and concentrated. Purification by normal phase chromatography afforded Intermediate 4A (0.760 g, 63%), as a brown oil. MS (ESI) m/z: 225.0 (M−C4H8+H)⁺.

Intermediate 4: A solution of Intermediate 4A (0.048 g, 0.171 mmol) in 50% TFA/DCM (2 mL) was stirred at rt. After 1 h, the reaction was concentrated to give Intermediate 4 (0.038 g, 100% yield) as a yellow solid. The material was carried onto the next step without further purification. MS (ESI) m/z: 225.1 (M+H)⁺.

Intermediate 5

(E)-3-(5-chloro-4-fluoro-2-(1H-tetrazol-1-yl)phenyl) acrylic acid

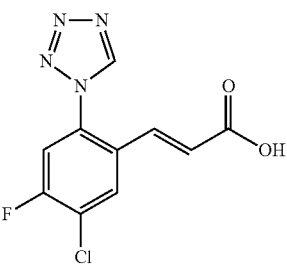 [SMILES: O=C(O)/C=C/c1cc(Cl)c(F)cc1-n1cnnn1]

Intermediate 5A: 4-chloro-5-fluoro-2-iodoaniline: To 4-chloro-3-fluoroaniline (25 g, 0.17 mmol) in 250 mL of H₂O was added NaHCO₃ (21.6 g, 0.25 mmol). After cooling to 0° C., iodine (43.5 g, 0.17 mmol) was added. After 18 h at rt, an additional 10.8 g of iodine was added and the reaction was stirred overnight. The reaction was extracted with DCM (4×250 mL), the combined organics were washed with sodium thiosulfate solution (2×250 mL) and brine (2×250 mL) and dried (Na₂SO₄). Purification by silica gel chromatography gave 47 g of Intermediate 5A. MS (ESI) m/z: 145.2 (M+H)⁺.

Intermediate 5B: 1-(4-chloro-5-fluoro-2-iodophenyl)-1H-tetrazole: To Intermediate 5A (47 g, 17.3 mmol) in AcOH (470 mL) was added NaN₃ (33.76 g, 51.9 mmol) and trimethyl orthoformate (56.8 mL, 51.9 mmol). After 30 h, the reaction was poured into ice water, then solid was filtered-off and washed with petroleum ether to afford 49 g of Intermediate 5B. MS (ESI) m/z: 324.8 (M+H)⁺.

Intermediate 5C: (E)-methyl 3-(5-chloro-4-fluoro-2-(1H-tetrazol-1-yl)phenyl)acrylate: A solution of Intermediate 5B (100 g, 324.4 mmol) in ACN (1000 mL) was degassed with N₂. TEA (64 mL) and methyl acrylate (60 mL) were added and the reaction was further degassed. Pd(OAc)₂ (8 g, 11.8 mmol) was added and the reaction was heated to 85° C. for 18 h. The reaction was concentrated and the residue was diluted with H₂O. The aqueous layer was extracted with EtOAc and the combined organics were washed with brine. Purification by silica gel chromatography gave 25 g of Intermediate 5C. MS (ESI) m/z: 283.0 (M+H)⁺.

Intermediate 5: (E)-3-(5-chloro-4-fluoro-2-(1H-tetrazol-1-yl)phenyl)acrylic acid: To Intermediate 5C (5 g, 17.7 mmol) in MeOH (50 mL) and THF (25 mL) was added 10% NaOH solution (25 mL). After 2 h, the reaction was concentrated and the residue was diluted with H₂O. The pH was adjusted to 2 to 3 with 1.5 N HCl and the resultant solid was filtered and washed with petroleum ether to afford 2 g of Intermediate 5. MS (ESI) m/z: 269.0 (M+H)⁺.

Intermediate 6 tert-Butyl 4-isocyanobenzoate

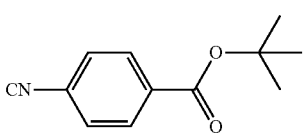

Intermediate 6A: tert-Butyl 4-formamidobenzoate: Combined tert-butyl 4-aminobenzoate (15.3 g, 79 mmol), DMAP (1.935 g, 15.84 mmol), N-methylmorpholine (15.67 mL, 143 mmol) in DCM (120 mL) and, after cooling to 0° C., slowly added formic acid (9.11 mL, 238 mmol). After stirring 18 h, the reaction was concentrated and then partitioned with 1N HCl (100 mL) and EtOAc (200 mL). The aqueous layer was extracted with EtOAc (100 mL). The combined organic layers were washed with brine (50 mL) and dried (MgSO₄). A thick yellow syrup (16 g) was collected and was carried onto the next step.

Intermediate 6: To Intermediate 6A in THF (300 mL) was added TEA (33 mL, 238 mmol) and then after cooling to 0° C., POCl₃ (7.3 mL, 79 mmol) was slowly added and the reaction was stirred at rt. After 24 h, the reaction was partitioned with EtOAc (200 mL) and dilute aqueous NaHCO₃ (100 mL). The aqueous layer was extracted with EtOAc (100 mL). The combined organic layers were washed with brine (50 mL) and dried (MgSO₄). Purification by normal phase chromatography afforded 10.4 g (65%) of intermediate 6 as a green solid. ¹H NMR (400 MHz, CDCl₃) δ 8.02 (d, J=8.59 Hz, 2 H), 7.41 (d, J=8.34 Hz, 2 H), 1.60 (s, 9 H) ppm.

Intermediate 7

4-Isocyanobenzonitrile

Intermediate 7 was prepared in a similar manner as Intermediate 6 from 4-isocyanoaniline. ¹H NMR (400 MHz, CDCl₃) δ 7.68-7.84 (m, 2 H) 7.51 (d, J=8.34 Hz, 2 H) ppm.

Intermediate 8 tert-Butyl 6-isocyano-1H-indazole-1-carboxylate

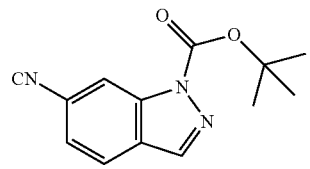

Intermediate 8 was prepared in a similar manner as Intermediate 6 from tert-butyl 6-amino-1H-indazole-1-carboxylate. 1H NMR (400 MHz, CDCl₃) δ 8.28 (1 H, s), 8.20 (1 H, s), 7.76 (1 H, d, J=8.34 Hz), 7.28-7.40 (1 H, m), 1.74 (9 H, s) ppm.MS (ESI) m/z: 144 (M+H-tboc)+.

Intermediate 9

Ethyl 4-isocyanobenzoate

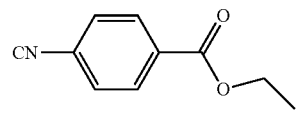

Intermediate 9 was prepared in a similar manner as Intermediate 6. ¹H NMR (400 MHz, CDCl₃) δ 1.40 (t, J=7.20 Hz, 3 H) 4.40 (q, J=7.24 Hz, 2 H) 7.44 (d, J=8.59 Hz, 2 H) 8.00-8.17 (m, 2 H) ppm. MS (ESI) m/z: 176 (M+H)⁺.

Intermediate 10

Methyl 4-isocyanophenylcarbamate

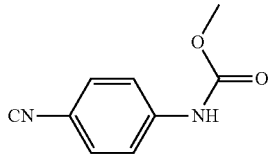

Intermediate 10A: 1-Boc-methyl 4-aminophenylcarbamate: To tert-butyl 4-aminophenylcarbamate (2.1 g, 10.08 mmol) in a separatory funnel with DCM (75 mL) and saturated aqueous NaHCO$_3$ (25 mL) was added methyl chloroformate (0.937 mL, 12.10 mmol). After shaking for 10 min a thick pink gel formed. The solid was filtered off and dried. The aqueous layer was extracted with DCM (50 mL) and dried (MgSO$_4$). All solids collected were combined to afford 2.6 g of Intermediate 10A. $^1$H NMR (400 MHz, MeOD) δ 7.32 (4 H, s), 3.73 (3 H, s), 1.53 (9 H, s) ppm.

Intermediate 10B: methyl 4-aminophenylcarbamate: Intermediate 10A (2.6 g, 9.77 mmol) was deprotected with 30% TFA in DCM (40 mL). After 2 h, the reaction was concentrated and the residue was partitioned with EtOAc (75 mL) and saturated NaHCO$_3$ (50 mL). The organic layer was washed with brine (20 mL) and dried (MgSO$_4$). Crude Intermediate 10B was carried onto the next step. $^1$H NMR (400 MHz, DMSO-d$_6$) δ 9.86 (1 H, s), 7.56 (2 H, d, J=8.84 Hz), 7.28 (2 H, d, J=8.84 Hz), 6.90 (2 H, s), 3.68 (3 H, s) ppm.

Intermediate 10C: Methyl 4-formamidophenylcarbamate: Crude Intermediate 10B was heated to reflux in ethyl formate for several days. The solvent was removed and the residue was purified by silica gel chromatography to afford 2.9 g of Intermediate 10C as a brown oil. MS (ESI) m/z: 195.0 (M+H)$^+$.

Intermediate 10 was made in a similar manner as Intermediate 6 to afford 0.31 g (17.8%) of a tan solid. $^1$H NMR (400 MHz, CDCl$_3$) δ 7.45 (2 H, d, J=8.8 Hz), 7.33-7.41 (2 H, m), 6.73 (1 H, br.s.), 3.82 (3 H, s) ppm.

Intermediate 11

Benzyl 6-isocyano-1H-indazole-1-carboxylate

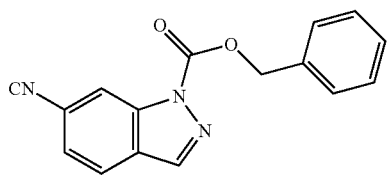

Intermediate 11 was made in a similar manner as Intermediate 6 and Intermediate 8 starting from benzyl 6-amino-1H-indazole-1-carboxylate. $^1$H NMR (400 MHz, CDCl$_3$) δ 8.31 (1 H, s), 8.21 (1 H, s), 7.76 (1 H, d, J=8.34 Hz), 7.54 (2 H, d, J=6.82 Hz), 7.30-7.47 (4 H, m), 5.56 (2 H, s) ppm. MS (ESI) m/z: 234 (M+H—CO$_2$)+.

Intermediate 12

(E)-3-(6-acetyl-3-chloro-2-fluorophenyl)acrylic acid

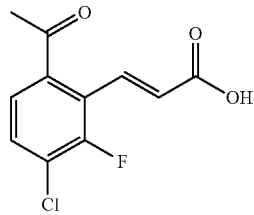 [SMILES: CC(=O)c1ccc(Cl)c(F)c1/C=C/C(=O)O]

Intermediate 12A: 2-bromo-4-chloro-3-fluorobenzoic acid: To a cooled (−78° C.) solution of DIEA (4.9 mL, 48 mmol) in THF was added drop wise n-BuLi (132 mL, 2.3 eq, 2.5 M solution). The mixture was stirred at −30° C. for 30 min. Again the reaction mixture was cooled to −78° C., and a solution of 4-chloro-3-fluorobenzoic acid (25 g, 143 mmol) in THF was added over 1 h. The reaction was stirred at −78° C. overnight. The next day a solution of 1,2-dibromo-1,1,2,2-tetrachloroethane (87 g, 267 mmol) in THF was added and the reaction was stirred at −78° C. for further 2 h and then rt for 4 h. The reaction mixture was quenched with H$_2$O, organic layer was separated and aqueous layer washed with Et$_2$O. Aqueous layer acidified with 1.5N HCl and extracted in EtOAc (2×200 mL), dried over anhydrous Na$_2$SO$_4$, filtered and concentrated to afford Intermediate 12A (30 g, 83.3% yield). MS (ESI) m/z: 252.6 (M−H)+.

Intermediate 12B: Diethyl 2-((2-bromo-4-chloro-3-fluorophenyl)(hydroxy)methylene) malonate: To a suspension of Intermediate 12A (14.6 g, 57 mmol) in DCM (200 mL) was added thionyl chloride (6.6 mL, 88 mmol). The mixture was stirred at reflux for 3 h. Solvent was removed and the residue was dried in vacuum to give the acid chloride as a light brown solid. To a cooled (0° C.) suspension of sodium hydride (3.66 g (60%), 91.5 mmol) in THF was added a solution of diethyl malonate (0.612 g, 3.82 mmol) in THF (5 mL). After 10 min, a solution of the acid chloride (16.4 g, 60 mmol) in THF (160 mL) was added slowly. Following the addition, the reaction was warmed to rt. After 30 min, the solvent was removed and the residue was treated with cold (0° C.) 1.2 M HCl (150 mL). The mixture was extracted with EtOAc (3×250 mL). The combined organic layers were washed with brine, dried over Na$_2$SO$_4$, filtered and concentrated to give Intermediate 12B (20 g, 87% yield) as a solid. MS (ESI) m/z: 395/397 (M+H)$^+$.

Intermediate 12C: 1-(2-Bromo-4-chloro-3-fluorophenyl)ethanone: A solution of Intermediate 12B (18.6 g, 47 mmol) in acetic acid (200 mL), H$_2$O (150 mL) and H$_2$SO$_4$ (2.0 mL) was stirred at 110° C. for 4 h. Most of the solvent was removed and the residue was diluted with EtOAc (400 mL), washed with H$_2$O (5×20 mL), saturated NaHCO$_3$, 1N NaOH, and brine. The solvent was removed to give Intermediate 12C (10 g, 84%) as a low melting solid. $^1$H NMR (400 MHz, DMSO-d$_6$) δ: 7.42 (q, J=6.8, 6.4 Hz, 1 H), 7.24 (q, J=6.4, 5.2 Hz, 1 H), 2.5 (s, 3H) ppm.

Intermediate 12D: (E)-tert-Butyl 3-(6-acetyl-3-chloro-2-fluorophenyl)acrylate: To a mixture of Intermediate 12C (50 g, 198 mmol), tert-butyl acrylate (50.9 g, 397 mmol) and TEA (55 mL, 397 mmol) in DMF (500 mL) was added Pd(OAc)$_2$ (8.9 g, 39.7 mmol). The resulting mixture was stirred at 90° C. overnight. The reaction was cooled to rt, filtered, and the filtrate was concentrated. Purification by column chromatography gave Intermediate 12D (30 g, 50.8%) as a light yellow solid. MS (ESI) m/z: 242.7 (M+H)+.

Intermediate 12: A solution of Intermediate 12D (25 g, 84 mmol) in DCM (330 mL) and TFA (330 mL) was stirred at rt. After 1.5 h, the solvent was concentrated to give Intermediate 12 (19.5 g, 97.0% yield) as a white solid. $^1$H NMR (400 MHz, DMSO-d$_6$) δ: 12.69 (bs, 1 H), 7.80-7.76 (m, 2 H), 7.62 (d, J=12.1 Hz, 1 H), 6.30 (dd, J=2.4, 2.0 Hz, 1 H), 2.6 (s, 3H) ppm. MS (ESI) m/z: 241 (M−H)+.

Intermediate 13

(E)-3-(3-Chloro-6-cyano-2-fluorophenyl)acrylic acid

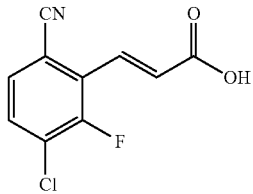 [SMILES: N#Cc1ccc(Cl)c(F)c1/C=C/C(=O)O]

Intermediate 13: 2-Bromo-4-chloro-3-fluorobenzamide: To a solution of 2-bromo-4-chloro-3-fluorobenzoic acid (20 g, 0.078 mol) in DCM (200 mL) was added thionyl chloride (14.7 g, 0.125 mol) followed by DMF (29.5 g, 0.5 moles) and the reaction was heated to reflux for 4 h. The reaction was cooled to 0° C. and NH$_3$ gas was bubbled in until the pH was basic. After 30 min., the reaction mixture was quenched with H$_2$O and extracted with DCM, the combined organics were washed with H$_2$O, brine, dried over Na$_2$SO$_4$, filtered and concentrated. Crude product was suspended in petroleum ether and filtered to afford 16.5 g of Intermediate 13A. MS (ESI) m/z: 250-254.0 (M+H)+.

Intermediate 13B: 2-Bromo-4-chloro-3-fluorobenzonitrile: To Intermediate 13A (10 g, 39 mmol) was added POCl$_3$ (100 mL) and NaOH (5 g, 87 mmol) and the reaction was heated to 110° C. for 2 h. The reaction mixture was concentrated and the residue was quenched with ice water. Extracted with EtOAc and the combined organics were washed with 10% NaHCO$_3$, brine, dried over Na$_2$SO$_4$, filtered and concentrated to afford 8.5 g of 13B. MS (ESI) m/z: 232.9-234.9 (M+H)+.

Intermediate 13C: (E)-Methyl 3-(3-chloro-6-cyano-2-fluorophenyl)acrylate: Combined Intermediate 13B (7 g, 29.9 mmol), tetrabutylammonium bromide (9.6 g, 29.9 mmol), NaHCO$_3$ (6.2 g, 74.8 mmol), methyl acrylate (5.2 g, 59.8 mmol) and Pd(OAc)$_2$ in DMF (50 mL). After 18 h, the reaction was heated to 90° C. for 4 h. The reaction was cooled to rt and filtered through Celite. Purification by normal phase chromatography afforded 3.5 g of Intermediate 13C. MS (ESI) m/z: 257 (M+H$_2$O)+.

Intermediate 13: To Intermediate 13C (0.5 g, 2.0 mmol) in THF (15 mL) and MeOH (5 mL) was added 1N LiOH (5 mL, 5 mmol). After 2 h, the volatile solvents were removed and the aqueous layer was extracted with EtOAc. The aqueous layer was acidified and extracted with EtOAc and the combined organics were washed with H$_2$O, brine, dried over Na$_2$SO$_4$, filtered and concentrated to afford 0.3 g of Intermediate 13. MS (ESI) m/z: 224-226.2 (M+H)+.

Intermediate 14

(E)-3-(5-Chloro-2-(difluoromethyl)phenyl)acrylic acid

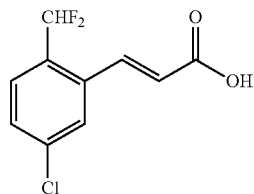 [SMILES: O=C(O)/C=C/c1cc(Cl)ccc1C(F)F]

Intermediate 14A: 2-Bromo-4-chloro-1-(difluoromethyl) benzene: To a solution of 2-bromo-4-chlorobenzaldehyde (1 g, 4.56 mmol) in DCM (15 mL) was added DAST (0.903 mL, 6.83 mmol) at 0° C. The reaction was allowed to warm to rt and stirred overnight. The reaction mixture was diluted with EtOAc, washed with saturated NaHCO$_3$ and brine. The organic phase was dried over MgSO$_4$, filtered and concentrated to give Intermediate 14A (0.88 g. 80% yield) as a clear oil. MS (ESI) m/z: 261.2 (M+Na)+.

Intermediate 14B: (E)-tert-Butyl 3-(5-chloro-2-(difluoromethyl)phenyl) acrylate: To a solution of Intermediate 14A (0.88 g, 3.64 mmol) in DMF (10 mL) was added tert-butyl acrylate (1.401 g, 10.93 mmol), TEA (1.270 mL, 9.11 mmol) and Pd(OAc)$_2$ (0.082 g, 0.364 mmol). The reaction was warmed to 90° C. After 5 h, the reaction was cooled to rt and then filtered to remove the solid. The filtrate was diluted with EtOAc, washed with 1M HCl, saturated NaHCO$_3$, and brine. The organic phase was dried over MgSO$_4$, filtered and concentrated. Purification by normal phase chromatography gave Intermediate 14B (232 mg, 22% yield) as a tan oil. MS (ESI) m/z: 233.1 (M-tBu)+.

Intermediate 14: To a solution of Intermediate 14B (232 mg, 0.804 mmol) in DCM (2.0 mL) was added TFA (2.0 mL, 26.0 mmol). The reaction was stirred under argon at rt. After 1 h, the solvent was removed and residue was dried to give Intermediate 14 (191 mg, 100%) as tan solid. $^1$H NMR (400 MHz, MeOD) δ 7.99 (dt, J=15.8, 1.5 Hz, 1H), 7.83 (s, 1H), 7.60 (d, J=8.3 Hz, 1H), 7.55-7.48 (m, 1H), 7.01 (t, J=54.6 Hz, 1H), 6.51 (d, J=15.8 Hz, 1H). 19F NMR (376 MHz, MEOD)☐ δ −111.67 (s, 2F) ppm. MS (ESI) m/z: 233.1 (M+H)+.

Intermediate 15

(E)-3-(5-Chloro-2-(difluoromethoxy)phenyl)acrylic acid

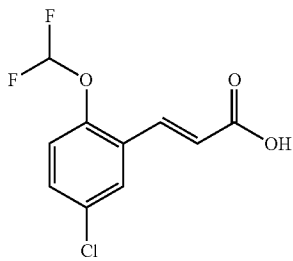 [SMILES: O=C(O)/C=C/c1cc(Cl)ccc1OC(F)F]

Intermediate 15A (E)-tert-Butyl 3-(5-chloro-2-(difluoromethoxy)phenyl) acrylate: To a solution of potassium tert-butoxide (0.407 g, 3.63 mmol) in THF (10 mL) were added tert-butyl 2-(dimethoxyphosphoryl)acetate (0.528 mL, 2.66 mmol) and 5-chloro-2-(difluoromethoxy)benzaldehyde (0.50 g, 2.420 mmol) at 0° C. After 4 hrs, NH$_4$Cl solution was added and the reaction mixture was diluted with EtOAc, washed with sat'd NH$_4$Cl solution, sat'd NaHCO$_3$, and brine. The organic phase was dried over Na$_2$SO$_4$, filtered and concentrated. The crude product was purified by normal phase chromatography. Intermediate 15A was obtained as a white solid 550 mg (74%). MS (ESI) m/z: 327.0 (M+Na)+0.19F NMR (376 MHz, CDCl$_3$) δ: −81.11 (1F, s) ppm.

Intermediate 15: To a solution of (E)-tert-butyl 3-(5-chloro-2-(difluoromethoxy) phenyl)acrylate (458 mg, 1.503 mmol) in DCM (4.0 mL) was added TFA (2.0 mL, 26.0 mmol). After 1 h, the solvent was removed to give Intermediate 15 as a white solid. MS (ESI) m/z: 249.0 (M+H)$^+$.

Intermediate 16

(E)-3-(3-chloro-2-fluoro-6-(trifluoromethyl)phenyl) acrylic acid

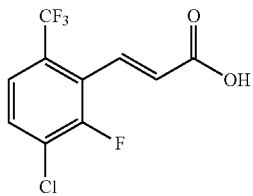 [SMILES: O=C(O)/C=C/c1c(C(F)(F)F)ccc(Cl)c1F]

Intermediate 16 was made in a similar manner as Intermediate 15 substituting 3-chloro-2-fluoro-6-(trifluoromethyl)benzaldehyde for 5-chloro-2-(difluoromethoxy) benzaldehyde followed by TFA deprotection. MS (ESI) m/z: 292 (M+Na)$^+$. $^1$H NMR (400 MHz, CDCl$_3$) δ 7.87 (1 H, dd, J=16.17, 2.02 Hz), 7.49-7.62 (2 H, m), 6.67 (1 H, dd, J=16.30, 1.39 Hz) ppm.

Intermediate 17

5-(pyridin-4-yl)-3,4-dihydroisoquinoline

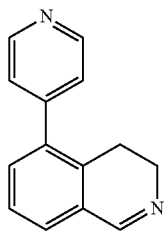 [SMILES: C1=NCCc2c1cccc2-c1ccncc1]

Intermediate 17A: tert-Butyl 5-(pyridin-4-yl)-3,4-dihydroisoquinoline-2(1H)-carboxylate: (Tet. Lett, 1995, 36, 5247) To tert-butyl 5-bromo-3,4-dihydroisoquinoline-2 (1H)-carboxylate (0.989 g, 3.17 mmol), 4-(tributylstannyl) pyridine (1.75 g, 4.75 mmol), LiCl (1.343 g, 31.7 mmol) in toluene (15 mL) was added dichlorobis(triphenylphosphine) palladium (II) (0.222 g, 0.317 mmol) and the reaction was heated to 110° C. After 72 h, the reaction was partitioned with 10% aq KF (20 mL) and EtOAc (50 mL). The aqueous layer was extracted with EtOAc (2×50 mL). The combined organic layers were washed with brine (15 mL) and dried (MgSO$_4$). Purification by silica gel chromatography afforded 0.63 g of Intermediate 17A as clear oil (64%). $^1$H NMR (400 MHz, CDCl$_3$) δ 8.66 (2 H, d, J=6.06 Hz), 7.23-7.33 (3 H, m), 7.17-7.21 (1 H, m), 7.13 (1H, d, J=7.58 Hz), 4.65 (2 H, s), 3.55 (2H, br. s), 2.72 (2 H, t, J=5.68 Hz), 1.50 (9 H, s) ppm.

Intermediate 17B: 5-(Pyridin-4-yl)-1,2,3,4-tetrahydroisoquinoline: To Intermediate 21A (0.14 g, 0.451 mmol) was added 10 mL H$_2$O and 4N HCl in dioxane (0.025 mL, 0.100 mmol). The reaction was heated to 150° C. in a microwave for 35 min, then freeze-dried to afford 90 mg Intermediate 17B as brown solid. MS (ESI) m/z: 211.1 (M+H)$^+$.

Intermediate 17: Intermediate 17B was oxidized using MnO$_2$. After 24 h, the reaction was filtered through Celite® and concentrated to afford 75 mg (80%) of Intermediate 17 as yellow oil. MS (ESI) m/z: 209.1 (M+H)$^+$.

Intermediate 18 tert-butyl 4-(3,4-dihydroisoquinolin-5-yl)-3-oxopiperazine-1-carboxylate

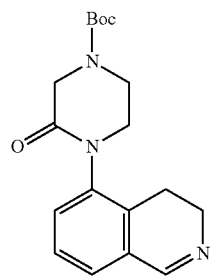 [SMILES: CC(C)(C)OC(=O)N1CCN(c2cccc3c2CCN=C3)C(=O)C1]

Intermediate 18A: tert-Butyl 4-(isoquinolin-5-yl)-3-oxopiperazine-1-carboxylate: To 5-bromoisoquinoline (0.3 g, 1.442 mmol) and tert-butyl 3-oxopiperazine-1-carboxylate (0.289 g, 1.442 mmol) was added DMSO (4 mL), 1,10-phenanthroline (0.026 g, 0.144 mmol), K$_2$CO$_3$ (0.498 g, 3.60 mmol). The mixture was degassed for 10 min. to the above mixture was then added CuI (0.055 g, 0.288 mmol). The reaction was heated in a sealed tube in oil bath at 130° C. After 24 h, the reaction was incomplete. Cooled and degassed with Ar, added more CuI and heating was repeated. After 24 h, the reaction was quenched with dilute NH$_4$OH (15 mL) and extracted with EtOAc (3×30 mL). The combined organic layers were washed with brine (15 mL) and dried (MgSO$_4$). The product was purified by normal phase chromatography followed by prep. HPLC. After partitioning with saturated NaHCO$_3$ (15 mL) and EtOAc (50 mL), the organic layer was washed with brine and dried (MgSO$_4$) to afford 0.157 g (54%) of Intermediate 18A as a white solid with recovered starting material. MS (ESI) m/z: 328 (M+H)$^+$.

Intermediate 18 was prepared from Intermediate 18A as described for Intermediate 17. MS (ESI) m/z: 330.1 (M+H)$^+$.

Example 1

(S,E)-4-(2-(3-(5-chloro-2-(1H-tetrazol-1-yl)phenyl)acryloyl)-1,2,3,4-tetrahydroisoquinoline-3-carboxamido)benzoic acid

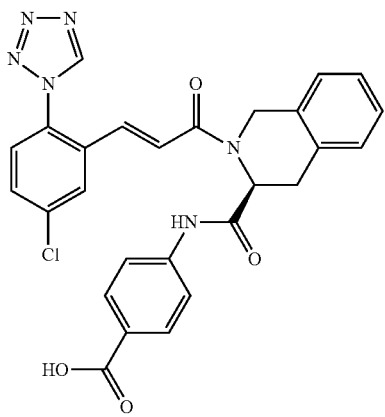 [SMILES: O=C(O)c1ccc(NC(=O)[C@@H]2Cc3ccccc3CN2C(=O)/C=C/c2cc(Cl)ccc2-n2cnnn2)cc1]

1A. (S)-Benzyl 3-(4-(tert-butoxycarbonyl)phenylcarbamoyl)-3,4-dihydroisoquinoline-2(1H)-carboxylate: To (S)-2-(benzyloxycarbonyl)-1,2,3,4-tetrahydroisoquinoline-3-carboxylic acid (0.161 g, 0.517 mmol) and tert-butyl 4-aminobenzoate (0.1 g, 0.517 mmol) in pyridine (2 ml), cooled to 0° C., was added POCl$_3$ (0.048 ml, 0.517 mmol). After 1 h, the reaction was partitioned with H$_2$O (15 mL) and EtOAc (40 mL). The organic layer was washed with 0.1 N HCl (10 mL), brine (10 mL) and dried (MgSO$_4$). Purified by normal phase chromatography to afford 0.247 g of desired product as brown film. MS (ESI) m/z: 487.4 (M+H)+.

1B. (S)-tert-Butyl 4-(1,2,3,4-tetrahydroisoquinoline-3-carboxamido)benzoate: 1A (0.247 g, 0.508 mmol) was hydrogenated at 50 psi for 1 h in EtOH (25 ml) with 10% Pd/C (35 mg). Filtered through Celite® and concentrated to give 0.134 g of desired product as pale grey solid. MS (ESI) m/z: 353.4 (M+H)$^+$.

1C. (S,E)-tert-Butyl 4-(2-(3-(5-chloro-2-(1H-tetrazol-1-yl)phenyl)acryloyl)-1,2,3,4-tetrahydroisoquinoline-3-carboxamido)benzoate: To 1B (0.1 g, 0.284 mmol) and Intermediate 1 (0.099 g, 0.284 mmol) in DMF (2 ml) was added DIEA (0.149 ml, 0.851 mmol). The reaction was quenched with H$_2$O (10 mL) and extracted with EtOAc (3×20 mE). The combined organic layers were washed with H$_2$O (10 mL), brine (10 mL) and dried (MgSO$_4$). Purified by normal phase chromatography to afford 0.15 g of desired product as yellow solid. MS (ESI) m/z: 585.2 (M+H)+.(M+H)$^+$.

Example 1: 1C (0.15 g, 0.256 mmol) was deprotected with DCM (5 mL)/TFA (2 mL). After 3 h, the reaction was concentrated, purified by reverse phase HPLC, and freeze-dried to afford 32 mg of desired product as pale yellow solid. $^1$H NMR (400 MHz, MeOD) δ 3.23-3.37 (m, 2 H) 4.88-4.91 (m, 1 H) 4.96-5.08 (m, 2 H) 7.20 (d, J=15.41 Hz, 1 H) 7.22-7.29 (m, 3 H) 7.36 (d, J=4.55 Hz, 1 H) 7.44 (d, J=15.41 Hz, 1 H) 7.55-7.63 (m, 3 H) 7.65-7.74 (m, 1 H) 7.94 (d, J=8.59 Hz, 2 H) 8.28 (d, J=2.02 Hz, 1 H) 9.55 (s, 1 H) ppm. MS (ESI) m/z: 529.0 (M+H)$^+$. Analytical HPLC: RT=8.5 min.

Example 2

(R,E)-4-(2-(3-(5-chloro-2-(1H-tetrazol-1-yl)phenyl)acryloyl)-1,2,3,4-tetrahydroisoquinoline-3-carboxamido)benzoic acid

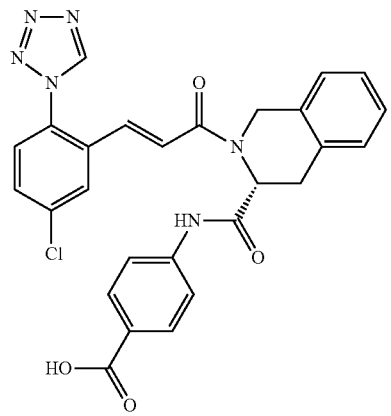 [SMILES: O=C(O)c1ccc(NC(=O)[C@H]2Cc3ccccc3CN2C(=O)/C=C/c2cc(Cl)ccc2-n2cnnn2)cc1]

Example 2 was made in a similar manner as Example 1 starting with (R)-2-(benzyloxycarbonyl)-1,2,3,4-tetrahydroisoquinoline-3-carboxylic acid. $^1$H NMR (400 MHz, MeOD) δ 9.55 (1 H, s), 8.29 (1 H, d, J=2.27 Hz), 7.95 (2 H, d, J=8.59 Hz), 7.70 (1 H, dd, J=8.59, 2.27 Hz), 7.54-7.66 (3 H, m), 7.44 (1 H, d, J=15.41 Hz), 7.34-7.39 (1 H, m), 7.27-7.31 (3 H, m), 7.21 (1 H, d, J=15.66 Hz), 5.01-5.10 (2 H, m), 4.88-4.95 (2 H, m), 3.24-3.32 (1 H, m) ppm. MS (ESI) m/z: 529.0 (M+H)+. Analytical HPLC: RT=7.5 min.

Example 3

(S,E)-4-(2-(3-(5-chloro-2-(1H-tetrazol-1-yl)phenyl)acryloyl)-1,2,3,4-tetrahydroisoquinoline-1-carboxamido)benzoic acid

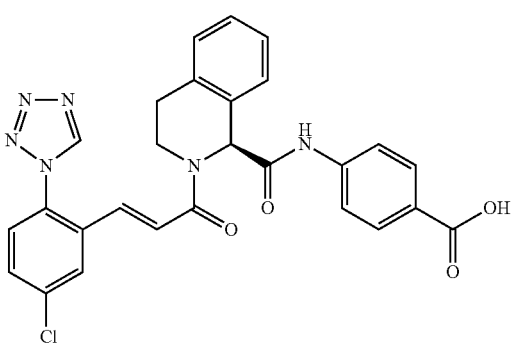 [SMILES: O=C(O)c1ccc(NC(=O)[C@@H]2c3ccccc3CCN2C(=O)/C=C/c2cc(Cl)ccc2-n2cnnn2)cc1]

3A: (S)-(9H-fluoren-9-yl)methyl 1-(4-(tert-butoxycarbonyl)phenyl carbamoyl)-3,4-dihydroisoquinoline-2(1H)-carboxylate: To (S)-2-(((9H-fluoren-9-yl)methoxy)carbonyl)-1,2,3,4-tetrahydroisoquinoline-1-carboxylic acid (0.358 g, 0.896 mmol) and tert-butyl 4-aminobenzoate (0.191 g, 0.986 mmol) in pyridine (2 mL)/DCM (5 mL), cooled to 0° C., was added POCl$_3$ (0.048 ml, 0.517 mmol). After 1 h, the reaction was partitioned with H$_2$O (15 mL) and EtOAc (40 mL). The organic layer was washed with 0.1 N HCl (10 mL), brine (10 mL) and dried (MgSO$_4$). Collected 0.64 g of desired product as white foam. MS (ESI) m/z: 575.4 (M+H)$^+$.

3B: (S)-tert-Butyl 4-(1,2,3,4-tetrahydroisoquinoline-1-carboxamido)benzoate: To 3A (0.64 g, 1.11 mmol) was added morpholine (0.3 mL) and DMF (4 mL). After 30 min, the reaction was partitioned with H$_2$O (10 mL) and EtOAc (20 mL). The organic layer was washed with H$_2$O (10 mL), brine (10 mL) and dried (MgSO$_4$) to afford 0.3 g of desired product as a foam. MS (ESI) m/z: 353.5 (M+H)$^+$.

3C: (S,E)-tert-Butyl 4-(2-(3-(5-chloro-2-(1H-tetrazol-1-yl)phenyl)acryloyl)-1,2,3,4-tetrahydroisoquinoline-1-carboxamido)benzoate: To Intermediate 2 (0.213 g, 0.851 mmol) and 3B (0.3 g, 0.851 mmol) in EtOAc (5 mL), cooled in ice bath, was added DIEA (0.446 mL, 2.55 mmol) and 50% T3P in EtOAc (0.481 mL, 1.702 mmol). After 1 h, the reaction was concentrated and the crude was taken on to next step. MS (ESI) m/z: 585.3 (M+H)$^+$.

Example 3: Crude 3C was dissolved in 30% TFA/DCM (15 mL) for 1 h. The reaction was concentrated, purified by reverse phase HPLC, and freeze-dried to afford 62 mg of desired product as light pink solid. $^1$H NMR (400 MHz, DMSO-d$_6$) δ 10.72 (1 H, s), 9.79-9.84 (1 H, m), 8.38 (1 H, d, J=2.02 Hz), 7.76-7.85 (2 H, m), 7.57-7.72 (5 H, m), 7.52-7.56 (1 H, m), 7.49 (1 H, d), 7.15-7.26 (3 H, m), 6.89 (1 H, d, J=15.16 Hz), 5.74 (1 H, s), 4.24-4.32 (1 H, m), 3.81 (1H, ddd, J=12.44, 8.40, 4.17 Hz), 3.04-3.19 (1 H, m), 2.85 (1 H, td) ppm. MS (ESI) m/z: 529.2 (M+H)$^+$. Analytical HPLC: RT=10.4 min.

Example 4

(R,E)-4-(2-(3-(5-chloro-2-(1H-tetrazol-1-yl)phenyl) acryloyl)-1,2,3,4-tetrahydroisoquinoline-1-carboxamido)benzoic acid

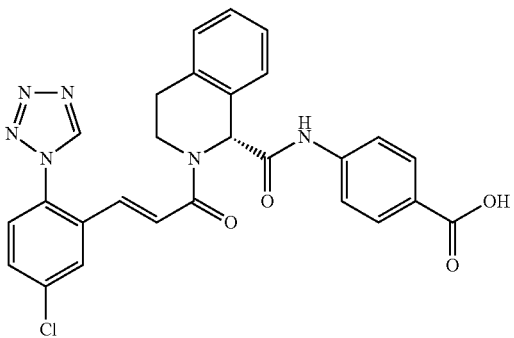 [SMILES: O=C(O)c1ccc(NC(=O)[C@H]2c3ccccc3CCN2C(=O)/C=C/c2cc(Cl)ccc2-n2cnnn2)cc1]

Example 4 was made in a similar manner as Example 3 starting with (R)-2-(((9H-fluoren-9-yl)methoxy)carbonyl)-1,2,3,4-tetrahydroisoquinoline-1-carboxylic acid. $^1$H NMR (400 MHz, MeOD) δ 9.54 (1 H, s), 8.20 (1 H, d, J=2.27 Hz), 7.96 (2 H, d, J=8.84 Hz), 7.62-7.70 (3 H, m), 7.51-7.60 (2 H, m), 7.35 (1 H, s), 7.25-7.31 (3 H, m), 7.14-7.27 (1 H, m), 5.84 (1 H, s), 4.33 (1 H, ddd, J=12.13, 5.31, 5.05 Hz), 3.85 (1 H, ddd, J=12.38, 8.84, 4.04 Hz), 3.28-3.33 (1 H, m), 2.92-3.05 (1 H, m) ppm. MS (ESI) m/z: 529.1 (M+H)$^+$. Analytical HPLC: RT=8.33 min.

Example 5

(S)-4-(2-(4-(N-hydroxycarbamimidoyl)benzoyl)-1,2,3,4-tetrahydroisoquinoline-1-carboxamido)benzoic acid, TFA salt

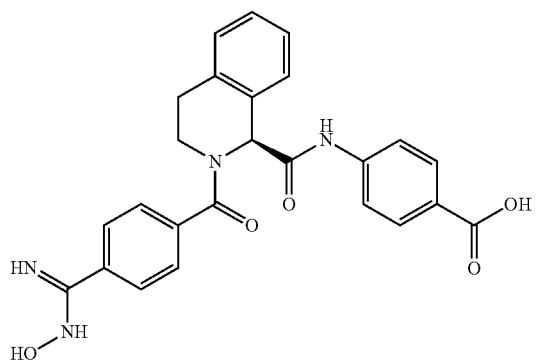 [SMILES: N=C(NO)c1ccc(C(=O)N2CCc3ccccc3[C@H]2C(=O)Nc2ccc(C(=O)O)cc2)cc1]

Example 5 was made in a similar manner as Example 3 starting with appropriate intermediates followed by dissolving in MeOH and treatment with hydroxylamine hydrochloride (0.020 g, 0.284 mmol) and DIEA (0.099 mL, 0.567 mmol) to yield the final desired product. $^1$H NMR (400 MHz, MeOD) δ 8.00 (2 H, d, J=8.6 Hz), 7.82-7.88 (2 H, m), 7.76-7.81 (2 H, m), 7.73 (2 H, d, J=8.6 Hz), 7.57-7.65 (1 H, m), 7.25-7.37 (3 H, m), 5.96 (1 H, s), 3.94-4.06 (1 H, m), 3.65 (1 H, ddd, J=12.3, 8.1, 3.9 Hz), 3.22 (1 H, ddd, J=15.3, 8.0, 4.2 Hz), 2.84-3.00 (1 H, m) ppm. MS (ESI) m/z: 459.0 (M+H)$^+$. Analytical HPLC: RT=4.42 min.

The following examples in Table 1 were made by the Ugi reaction as described in Example 3, using the corresponding imine intermediates, acid intermediates and appropriate nitrile intermediates

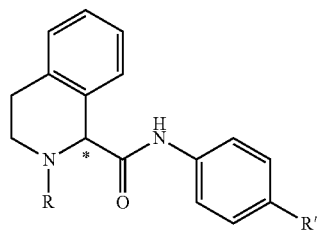

TABLE 1

| Example # | Stereochemistry | R | R' | M + H | RT |
|---|---|---|---|---|---|
| 6 | Racemic | | NHCOOMe | 465.0 | 4.67 |
| 7 | S-enantiomer | | COOH | 436.1 | 4.50 |

Example 8

(S,E)-4-(6-(benzyloxy)-2-(3-(5-chloro-2-(1H-tetrazol-1-yl)phenyl) acryloyl)-1,2,3,4-tetrahydroisoquinoline-1-carboxamido)benzoic acid

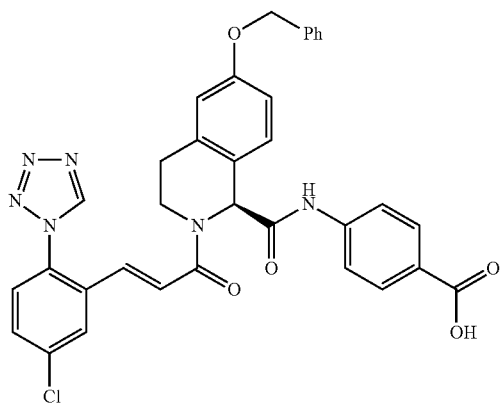 [SMILES: O=C(O)c1ccc(NC(=O)[C@@H]2c3ccc(OCc4ccccc4)cc3CCN2C(=O)/C=C/c2cc(Cl)ccc2-n2cnnn2)cc1]

8A: (S)-2-tert-Butyl 1-methyl 6-(benzyloxy)-3,4-dihydroisoquinoline-1,2(1H)-dicarboxylate: To (S)-2-tert-butyl 1-methyl 6-hydroxy-3,4-dihydroisoquinoline-1,2(1H)-dicarboxylate (0.233 g, 0.758 mmol) in acetone (50 mL), was added $K_2CO_3$ (2.09 g, 15.16 mmol), and (bromomethyl) benzene (0.194 g, 1.137 mmol). After 24 h, the reaction was quenched with $H_2O$ (100 mL) and extracted organics with EtOAc (2×100 mL), dried and evaporated to a pinkish oil. Re-dissolved in DCM and purified by normal phase chromatography and concentrated to yield 0.36 g of desired product as oil.

8B: (S)-6-(Benzyloxy)-2-(tert-butoxycarbonyl)-1,2,3,4-tetrahydroisoquinoline-1-carboxylic acid: To 8A (0.36 g, 0.911 mmol) in THF/$H_2O$ (20 mL) was added LiOH (0.131 g, 5.4 mmol). The reaction mixture was stirred for 5 h and quenched with $H_2O$ (100 mL) and extracted with ether (50 mL). The aqueous layer was acidified with 1 N HCl and extracted with EtOAc (2×100 mL), dried and evaporated to foam. MS (ESI) m/z: 382.2 $(M+H)^+$.

8C: (S)-tert-Butyl 6-(benzyloxy)-1-(4-(tert-butoxycarbonyl)phenylcarbamoyl)-3,4-dihydroisoquinoline-2(1R)-carboxylate: To 8B (0.08 g, 0.209 mmol) and tert-butyl 4-aminobenzoate (0.040 g, 0.209 mmol) in EtOAc (2 mL), cooled in ice bath, was added DIEA (0.091 mL, 0.522 mmol) and 50% T3P in EtOAc (0.118 mL, 0.417 mmol). After 24 h, the reaction was concentrated and purification by normal phase chromatography afforded 54 mg (46%) of desired product. MS (ESI) m/z: 559.4 (M+H)+

8D: (S)-4-(6-(Benzyloxy)-1,2,3,4-tetrahydroisoquinoline-1-carboxamido)benzoic acid: To 8C (54 mg, 0.097 mmol) was added 4N HCl/dioxane (2 mL) and after 24 h, the solvents were removed to afford a foam which was carried onto the next step. MS (ESI) m/z: 403.3 (M+H)+

Example 8 was made in a similar manner as Example 1 combining Intermediate 1 and 8D. $^1$H NMR (400 MHz, MeOD) δ 10.42 (1 H, s), 9.54 (1 H, s), 8.21 (1 H, d, J=2.27 Hz), 7.92-8.04 (2 H, m), 7.64-7.72 (3 H, m), 7.59 (1 H, d, J=8.59 Hz), 7.42-7.47 (2 H, m), 7.29-7.39 (3 H, m), 7.16-7.23 (1 H, m), 6.86-6.98 (2 H, m), 5.77 (1 H, s), 5.11 (2 H, s), 4.91-4.96 (1 H, m), 4.26-4.37 (1 H, m), 3.76-3.89 (1 H, m), 2.88-3.35 (2 H, m) ppm. MS (ESI) m/z: 635.2 $(M+H)^+$. Analytical HPLC: RT=8.47 min.

Example 9

(S,E)-3-(2-(3-(5-chloro-2-(1H-tetrazol-1-yl)phenyl) acryloyl)-1,2,3,4-tetrahydroisoquinoline-1-carboxamido)benzoic acid

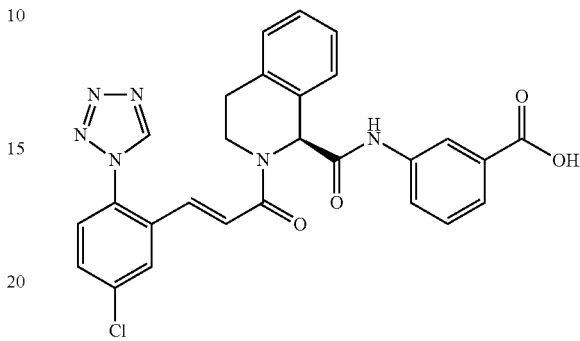

Example 9 was made in a similar manner as Example 3 starting with tert-butyl 3-aminobenzoate. $^1$H NMR (400 MHz, MeOD) δ 9.55 (1 H, s), 8.18-8.23 (2 H, m), 7.74-7.82 (2 H, m), 7.66-7.71 (1 H, m), 7.53-7.62 (2 H, m), 7.38-7.45 (2 H, m), 7.33-7.37 (1 H, m), 7.27-7.33 (4 H, m), 7.17-7.25 (1 H, m), 5.84 (1 H, s), 4.33 (1 H, dt, J=12.06, 5.34 Hz), 3.82-3.89 (1 H, m), 2.92-3.03 (1 H, m) ppm. MS (ESI) m/z: 529.3 $(M+H)^+$. Analytical HPLC: RT=10.44 min.

Example 10

(S,E)-4-(2-(3-(3-Chloro-2-fluoro-6-(1H-tetrazol-1-yl)phenyl)acryloyl)-1,2,3,4-tetrahydroisoquinoline-1-carboxamido)benzoic acid

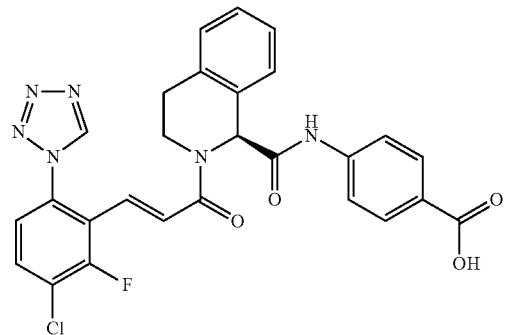 [SMILES: O=C(O)c1ccc(NC(=O)[C@@H]2c3ccccc3CCN2C(=O)/C=C/c2c(-n3cnnn3)ccc(Cl)c2F)cc1]

Example 10 was prepared in a similar manner as Example 3 using Intermediate 3A. $^1$H NMR (400 MHz, MeOD) δ 9.56 (1 H, s), 7.97 (2 H, d, J=8.84 Hz), 7.78-7.85 (1 H, m), 7.64-7.70 (2 H, m), 7.47-7.56 (2 H, m), 7.29 (4 H, d, J=2.53 Hz), 7.04-7.19 (2 H, m), 5.84 (1 H, s), 4.18 (1 H, ddd, J=12.00, 5.31, 5.18 Hz), 3.64-3.74 (1 H, m), 2.95 (1 H, dt, J=15.35, 4.83 Hz) ppm. MS (ESI) m/z: 547.3 $(M+H)^+$. Analytical (method B) HPLC: RT=6.73 min.

Example 11

(S,E)-Methyl 4-(2-(3-(3-chloro-2-fluoro-6-(1H-tetrazol-1-yl)phenyl)acryloyl)-1,2,3,4-tetrahydroisoquinoline-1-carboxamido)phenylcarbamate

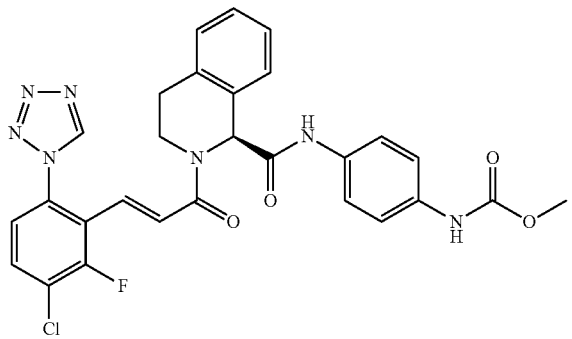 [SMILES: COC(=O)Nc1ccc(NC(=O)[C@@H]2c3ccccc3CCN2C(=O)/C=C/c2c(-n3cnnn3)ccc(Cl)c2F)cc1]

11A: (S)-(9H-fluoren-9-yl)methyl 1-(4-nitrophenylcarbamoyl)-3,4-dihydroisoquinoline-2(1H)-carboxylate: To (S)-2-(((9H-fluoren-9-yl)methoxy)carbonyl)-1,2,3,4-tetrahydroisoquinoline-1-carboxylic acid (0.249 g, 0.623 mmol) and 4-nitroaniline (95 mg, 0.686 mmol) in EtOAc (5 mL) was added 50% T3P in EtOAc (0.26 mL, 0.935 mmol) and DIEA (0.32 mL, 1.87 mmol). After 24 h, the reaction was concentrated and purified by normal phase chromatography to afford 55 mg of 11A as a bright yellow solid. MS (ESI) m/z: 520.4 (M+H)+.

11B: (S)-(9H-fluoren-9-yl)methyl 1-(4-aminophenylcarbamoyl)-3,4-dihydroisoquinoline-2(1H)-carboxylate: To 11A (55 mg, 0.105 mmol) in acetone (8 mL)/H2O (3 mL) was added zinc (0.2 g, 3.12 mmol) and slowly added ammonium chloride (0.33 g/6.23 mmol). After 24 h, the reaction was filtered and filtrate concentrated. Extraction with EtOAc (3×20 mL), washing with brine (20 mL) and drying (MgSO4) afforded 11B which was carried onto the next step. MS (ESI) m/z: 490.3 (M+H)+.

11C: (S)-(9H-fluoren-9-yl)methyl 1-(4-(methoxycarbonylamino) phenylcarbamoyl)-3,4-dihydroisoquinoline-2(1H)-carboxylate: 11B was dissolved in DCM (3 mL) and pyridine (1 mL) and treated with methyl chloroformate (0.048 mL, 0.623 mmol) for 30 min. The reaction was quenched with 1N HCl and extracted with DCM (3×20 mL). The combined organic layers were washed with brine (10 mL) and dried (MgSO4) to afford 11C (59 mg) as a tan solid. MS (ESI) m/z: 548.3 (M+H)+.

11D: (S)-Methyl 4-(1,2,3,4-tetrahydroisoquinoline-1-carboxamido) phenylcarbamate: To 11C (59 mgs, 0.11 mmol) in DMF (1 mL) was added morpholine (0.3 mL). After 2 h, the reaction was partitioned with H2O/brine (15 mL) and EtOAc (30 mL). The organic layer was washed with brine (10 mL) and dried (MgSO4). Collected 34 mgs of crude 11D, which was used in the next steps without purification. MS (ESI) m/z: 326.4 (M+H)+.

Example 11: To Intermediate 3A (12.38 mg, 0.046 mmol) and crude 11D (15 mg, 0.046 mmol) in EtOAc (2 mL) was added DIEA (24.16 μL, 0.138 mmol) and 50% solution of T3P in EtOAc (19.55 μL, 0.069 mmol). After 2 h, the reaction was concentrated and purified by reverse phase HPLC and freeze-dried to afford 11 mg (38.5%) of desired product as white solid. 1H NMR (400 MHz, DMSO-d6) δ 10.35-10.41 (1 H, m), 9.87 (1 H, s), 9.53-9.58 (1 H, m), 7.90-8.00 (1 H, m), 7.64-7.70 (1 H, m), 7.57-7.62 (1 H, m), 7.41-7.50 (2 H, m), 7.32-7.38 (2 H, m), 7.25 (4 H, d, J=3.03 Hz), 7.03-7.15 (1 H, m), 6.91-6.99 (1 H, m), 5.77-5.82 (1 H, m), 4.08-4.17 (1 H, m), 3.67-3.73 (1 H, m), 3.64 (3 H, s), 3.11-3.19 (1 H, m), 2.83-2.90 (1 H, m) ppm. MS (ESI) m/z: 576 (M+H)+. Analytical HPLC: RT=8.7 min.

Example 12

(S,E)-methyl 4-(2-(3-(5-chloro-2-(1H-tetrazol-1-yl)phenyl)acryloyl)-1,2,3,4-tetrahydroisoquinoline-1-carboxamido)phenylcarbamate

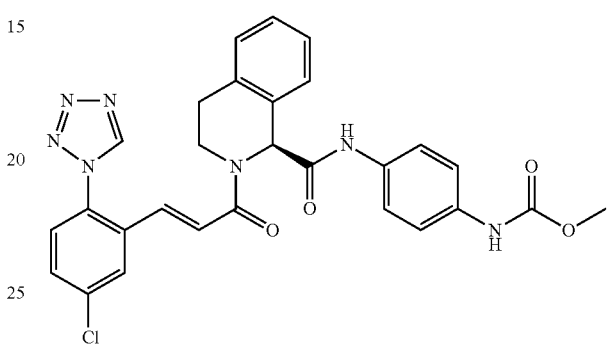

Example 12 was made in a similar manner as Example 11 using Intermediate 2 instead of intermediate 3A. 1H NMR (400 MHz, DMSO-d6) δ 10.38 (1 H, s), 9.87 (1 H, s), 9.54 (1 H, s), 8.44 (1 H, d, J=2.27 Hz), 7.69-7.83 (2 H, m), 7.55-7.63 (1 H, m), 7.42-7.52 (2 H, m), 7.32-7.38 (2 H, m), 7.18-7.31 (4 H, m), 6.95 (1 H, d, J=15.41 Hz), 5.79 (1 H, s), 4.25-4.35 (1 H, m), 3.93 (1 H, s), 3.63 (3 H, s), 3.12-3.22 (1 H, m), 2.85-2.97 (1 H, m) ppm. MS (ESI) m/z: 558 (M+H)+. Analytical HPLC: RT=8.08 min.

Example 13

(S,E)-2-(3-(5-Chloro-2-(1H-tetrazol-1-yl)phenyl)acryloyl)-N-(1-oxo-1,2-dihydroisoquinolin-6-yl)-1,2,3,4-tetrahydroisoquinoline-1-carboxamide

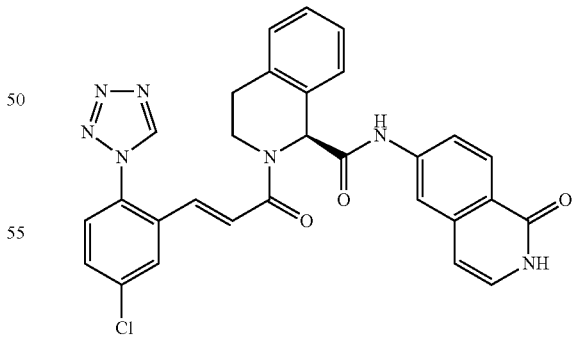

Example 13 was made in a similar manner as Example 3 using 6-aminoisoquinolin-1(2H)-one. 1H NMR (400 MHz, DMSO-d6) δ 11.07 (1 H, d, J=5.31 Hz), 10.81 (1 H, s), 9.87 (1 H, s), 8.45 (1 H, d, J=2.27 Hz), 8.09 (1 H, d, J=8.84 Hz), 7.91 (1 H, d, J=2.02 Hz), 7.69-7.78 (2 H, m), 7.52-7.65 (3 H, m), 7.21-7.35 (3 H, m), 7.09 (1 H, dd, J=7.07, 5.81 Hz), 6.97 (1 H, d, J=15.4 Hz), 6.42 (1 H, d, J=7.07 Hz), 5.83 (1

H, s), 4.30-4.42 (1 H, m), 3.89 (1 H, ddd, J=12.51, 8.46, 4.29 Hz), 3.21 (1 H, ddd, J=19.90, 4.42, 4.23 Hz), 2.92 (1 H, dd, J=9.98, 5.18 Hz) ppm. MS (ESI) m/z: 552.4 (M+H)+. Analytical HPLC: RT=7.5 min.

Example 14

(S,E)-2-(3-(5-Chloro-2-(1H-tetrazol-1-yl)phenyl)acryloyl)-N-(1H-indazol-6-yl)-1,2,3,4-tetrahydroisoquinoline-1-carboxamide

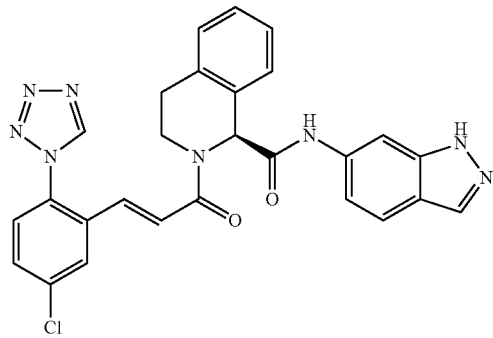 [SMILES: O=C(Nc1ccc2cn[nH]c2c1)[C@@H]1c2ccccc2CCN1C(=O)/C=C/c1cc(Cl)ccc1-n1cnnn1]

Example 14 was made in a similar manner as Example 3 using 1H-indazol-6-amine. $^1$H NMR (400 MHz, MeOD) δ 9.53 (1 H, s), 8.17 (1 H, d, J=2.27 Hz), 8.01 (1 H, d, J=2.27 Hz), 7.62-7.73 (2 H, m), 7.56 (2 H, d, J=8.59 Hz), 7.36 (1 H, d, J=15.4 Hz), 7.26-7.31 (4 H, m), 7.21 (1 H, d, J=15.4 Hz), 7.13 (1 H, dd, J=8.72, 1.64 Hz), 5.89 (1 H, s), 4.29-4.36 (1 H, m), 3.87 (1 H, ddd, J=12.44, 8.65, 4.17 Hz), 3.29-3.35 (1 H, m), 2.92-3.02 (1 H, m) ppm. MS (ESI) m/z: 525.4 (M+H)+. Analytical HPLC: RT=7.78 min.

Example 15

(E)-4-(2-(3-(5-Chloro-2-(1H-tetrazol-1-yl)phenyl)acryloyl)-6-(2-methoxyethoxy)-1,2,3,4-tetrahydroisoquinoline-1-carboxamido)benzoic acid.

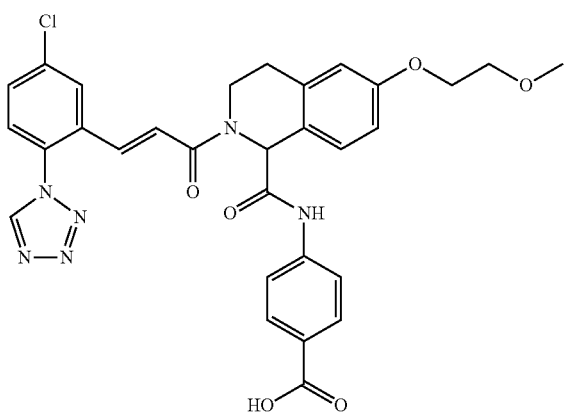 [SMILES: COCCOc1ccc2c(c1)CCN(C(=O)/C=C/c1cc(Cl)ccc1-n1cnnn1)C2C(=O)Nc1ccc(C(=O)O)cc1]

15A: 2-tert-Butyl 1-methyl 6-hydroxy-3,4-dihydroisoquinoline-1,2(1H)-dicarboxylate: 15A was prepared as described in the literature (Gill, I. S et al. *Tetrahedron: Asymmetry*, 2007, 18, pp. 2147-2154).

15B: 4-(6-(2-Methoxyethoxy)-1,2,3,4-tetrahydroisoquinoline-1-carboxamido)benzoic acid, TFA salt: A suspension of 15A (0.50 g, 1.63 mmol), p-toluenesulfonic acid 2-methoxyethyl ester (0.38 g, 1.63 mmol), and K$_2$CO$_3$ (0.68 g, 4.88 mmol) in DMF (5 mL) was heated at 80° C. overnight. The reaction was cooled to rt, filtered, and rinsed with EtOAc (3×25 mL). The combined filtrate was washed with H$_2$O, 1.0 M HCl solution, brine, and dried over Na$_2$SO$_4$, filtered, and dry-loaded onto silica gel. Purification by silica gel chromatography afforded a colorless oil (550 mg, 93%) as the desired intermediate. The ester was then dissolved in THF (10 mL) and treated with LiOH (0.205 g, 4.88 mmol) in H$_2$O (3 mL) followed by MeOH (1 mL). After 14 h, the mixture was diluted with H$_2$O and organics concentrated. The remaining aqueous layer was made acidic with 10% citric acid and extracted with EtOAc (3×30 mE). The combined organic extract was washed with H$_2$O, brine, dried over Na$_2$SO$_4$, filtered, and concentrated give the desired carboxylic acid. This material and tert-butyl 4-aminobenzoate (0.31 g, 1.63 mmol) in pyridine (10 mL) were treated with phosphorus oxychloride (0.15 mL, 1.63 mmol) at −10° C. After 2 h, the reaction was quenched with H$_2$O and extracted with EtOAc. The organic layer was washed with H$_2$O, 1.0M HCl solution, H$_2$O, brine, dried over Na$_2$SO$_4$, filtered, and concentrated. The residue was treated with 50% TFA/DCM. After stirring for 2 h, the reaction was concentrated to dryness The residue was purified reversed phase HPLC and concentrated in vacuo to give 15B (225 mg, 29%) as an oil. MS (ESI) m/z: 371.3 (M+H)+.

Example 15: DIEA (0.09 mL, 0.52 mmol) was added to a stirring solution of 15B and Intermediate 1 in DMF (3 mL). After 2 h, the crude material was purified by reverse phase HPLC and freeze-dried to afford 12 mg (18%) of desired product as white solid. $^1$H NMR (400 MHz, DMSO-d$_6$) δ 10.73 (1 H, s), 9.87 (1 H, s), 8.43-8.46 (1 H, m), 7.86 (2 H, d, J=8.79 Hz), 7.64-7.78 (4 H, m), 7.50-7.59 (2 H, m), 6.95 (1 H, d, J=15.39 Hz), 6.82-6.89 (1 H, m), 5.72 (1 H, s), 4.29-4.37 (1 H, m), 4.05-4.10 (2 H, m), 3.77-3.86 (1 H, m), 3.61-3.65 (2 H, m), 3.29 (3 H, s), 3.12-3.22 (1 H, m), 2.83-2.92 (1 H, m) ppm. MS (ESI) m/z: 603.5 (M+H)+. Analytical HPLC: RT=6.15 min.

Example 16

(E)-4-(2-(3-(5-Chloro-2-(1H-tetrazol-1-yl)phenyl)acryloyl)-6-methoxy-1,2,3,4-tetrahydroisoquinoline-1-carboxamido)benzoic acid

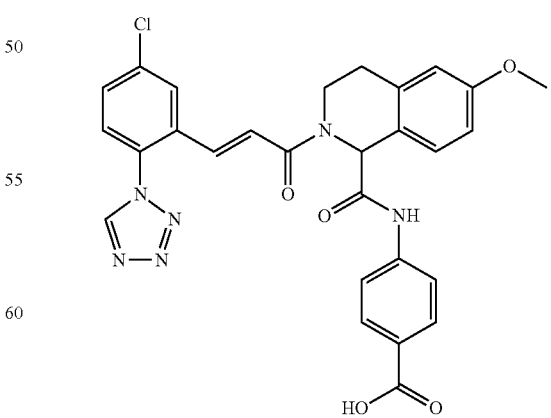

16A: 4-(6-Methoxy-1,2,3,4-tetrahydroisoquinoline-1-carboxamido)benzoic acid, TFA salt: Sodium hydride (0.098 g, 2.44 mmol) was added to 15A (0.500 g, 1.63 mmol) in DMF (5 mL) at 0° C. The reaction was allowed to come to rt and stirred for 1 h before again cooling the mixture back to 0° C. Iodomethane (0.10 mL, 1.63 mmol) was slowly added and the mixture allowed to raise to rt. After 16 h, the reaction mixture was diluted with EtOAc (50 mL) and treated with H₂O (50 mL). The H₂O layer was separated and extracted once again with EtOAc (50 mL). The combined organic extract was washed with brine, dried over Na₂SO₄, filtered, and concentrated. Purification by silica gel chromatography gave colorless oil. The ester was hydrolyzed by dissolution in THF (10 mL), treatment with lithium hydroxide monohydrate (0.14 g, 3.25 mmol) (3 mL), and the addition of MeOH (1 mL). After 12 h, the mixture was diluted with H₂O and organics concentrated. The remaining aqueous layer was made acidic with 10% citric acid and extracted with EtOAc (3×30 mL). The combined organic extract was washed with H₂O, brine, dried over Na₂SO₄, filtered, and concentrated. This material and tert-butyl 4-aminobenzoate (0.314 g, 1.63 mmol) in pyridine (10 mL) was treated with POCl₃ (0.15 mL, 1.63 mmol) at −10° C. After stirring for 2 h, the reaction was quenched with H₂O and extracted with EtOAc. The organic layer was washed with H₂O, 1.0 M HCl solution, H₂O, brine, dried over Na₂SO₄, filtered, and concentrated. The residue was treated with 50% TFA/DCM. After 2 h, the reaction was concentrated. Purification by reverse phase HPLC and concentrating in vacuo gave 16A as oil. MS (ESI) m/z: 327.3 (M+H)⁺.

Example 16: DIEA (0.099 mL, 0.568 mmol) was added to 16A (0.05 g, 0.114 mmol) and Intermediate 1 in DMF (3 mL). After 2 h, the crude material was purified by reverse phase HPLC and freeze-dried to afford 36 mg (52%) of a white solid. ¹H NMR (400 MHz, DMSO-d₆) δ 10.72 (1 H, s), 9.87 (1 H, s), 8.44 (1 H, d, J=2.20 Hz), 7.86 (2 H, d, J=8.79 Hz), 7.70-7.79 (2 H, m), 7.66 (2 H, d, J=8.79 Hz), 7.51-7.60 (2 H, m), 6.95 (1 H, d, J=15.39 Hz), 6.82-6.89 (2 H, m), 5.72 (1 H, s), 4.30-4.38 (1 H, m), 3.77-3.85 (1 H, m), 3.73 (3H, s), 3.14-3.23 (1H, m), 2.84-2.93 (1 H, m) ppm. MS (ESI) m/z: 559.4 (M+H)⁺. Analytical HPLC: RT=6.41 min.

Example 17

(S,E)-Methyl 3-(2-(3-(5-chloro-2-(1H-tetrazol-1-yl)phenyl)acryloyl)-1,2,3,4-tetrahydroisoquinoline-1-carboxamido)phenylcarbamate

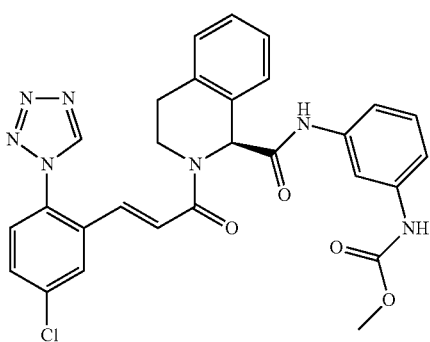 [SMILES: COC(=O)Nc1cccc(NC(=O)[C@@H]2c3ccccc3CCN2C(=O)/C=C/c2cc(Cl)ccc2-n2cnnn2)c1]

Example 17 was made in a similar manner as Example 3 using methyl 3-aminophenyl carbamate. ¹H NMR (400 MHz, MeOD) δ 8.68 (1 H, s), 8.03 (1 H, s), 6.70 (1 H, d, J=2.02 Hz), 6.13-6.21 (2 H, m), 6.08 (1 H, d, J=8.59 Hz), 6.03 (1 H, dd, J=6.95, 2.65 Hz), 5.83-5.91 (1 H, m), 5.73-5.81 (3 H, m), 5.64-5.73 (3 H, m), 4.34 (1 H, s), 2.74-2.84 (1 H, m), 2.37 (1 H, ddd, J=12.32, 8.53, 4.17 Hz), 2.22 (3 H, s), 1.75-1.81 (1 H, m), 1.47 (1 H, ddd, J=10.55, 5.56, 5.37 Hz) ppm. MS (ESI) m/z: 557 (M+H)⁺. Analytical HPLC: RT=8.32 min.

Example 18

(S,E)-Methyl 3-(2-(3-(5-chloro-2-(1H-tetrazol-1-yl)phenyl)acryloyl)-1,2,3,4-tetrahydroisoquinoline-1-carboxamido)benzo[d]isoxazol-7-ylcarbamate

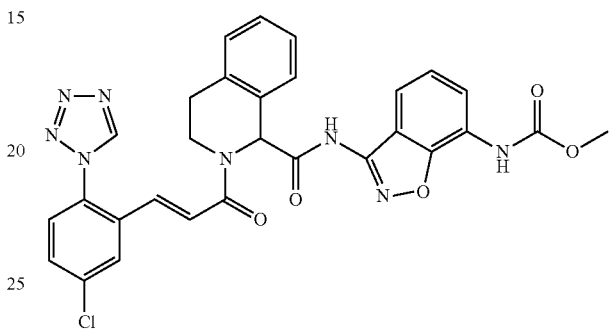

18A: Methyl 3-cyano-2-fluorophenylcarbamate: To 3-amino-2-fluorobenzonitrile (0.5 g, 3.67 mmol) in DCM (10 mL) cooled to 0° C., was added pyridine (1 mL) and methyl chloroformate (0.313 mL, 4.04 mmol). After 24 h, the reaction was quenched with H₂O (20 mL) and extracted with EtOAc (3×30 mL). The combined organic layers were washed with 1N HCl (20 mL), brine (20 mL) and dried (MgSO₄) to afford 0.7 g (98%) of 18A as brown solid. MS (ESI) m/z: 195.2 (M+H)⁺.

18B: Methyl 3-aminobenzo[d]isoxazol-7-ylcarbamate To 18A (0.12 g, 0.618 mmol), acetohydroxamic acid (0.102 g, 1.360 mmol) and K₂CO₃ (0.188 g, 1.360 mmol) was added DMF (3 mL)/H₂O (1 drop) and the reaction was heated to 40° C. for 24 h. The reaction was quenched with H₂O (10 mL) and extracted with EtOAc (3×20 mL). The combined organic layers were washed with H₂O (10 mL), brine (10 mL) and dried (MgSO₄). Tituration with DCM afforded a tan solid which was filtered off and dried to afford 70 mg (55%) of 18B. MS (ESI) m/z: 208.2 (M+H)⁺.

18C: (S)-(9H-fluoren-9-yl)methyl 1-(7-(methoxycarbonylamino) benzo[d]isoxazol-3-ylcarbamoyl)-3,4-dihydroisoquinoline-2(1H)-carboxylate: To (S)-2-(((9H-fluoren-9-yl)methoxy)carbonyl)-1,2,3,4-tetrahydroisoquinoline-1-carboxylic acid (135 mg, 0.338 mmol) and 18B (70 mg, 0.338 mmol) in DCM (4 mL)/pyridine (1 mL), cooled in ice/acetone bath, was added POCl₃ (31.5 μL, 0.338 mmol). After 1 h, the reaction was diluted with EtOAc (100 mL), washed with 1N HCl (20 mL), brine (20 mE) and dried (MgSO₄). Purified by normal phase chromatography to afford 0.11 g (55%) of 18C as white foam. MS (ESI) m/z: 589.2 (M+H)⁺.

18D: (S)-Methyl 3-(1,2,3,4-tetrahydroisoquinoline-1-carboxamido)benzo [d]isoxazol-7-ylcarbamate: Deprotected 18C in DMF (6 mL) with morpholine (2 mL). After 1.5 h, the reaction was quenched with EtOAc (30 mL) and 1:1 H₂O/brine (20 mL), organic layer washed with brine (10 mL) and dried (MgSO₄). Collected 0.14 g of crude 18D as a yellow solid. MS (ESI) m/z: 367 (M+H)⁺.

Example 18: To Intermediate 2 (46.5 mg, 0.186 mmol) and 18D (68 mg, 0.186 mmol) in EtOAc (3 mL)/CHCl$_3$ (1 mL) was added DIEA (97 µL, 0.557 mmol), cooled in ice bath, and added 50% T3P in EtOAc (79 µL, 0.278 mmol). After 1.5 h, the reaction was stripped and purified by reverse phase HPLC. To remove slight impurity the product was titurated with MeOH, filtered and 30 mg (26.7%) of desired product was collected as white solid. $^1$H NMR (400 MHz, DMSO-d$_6$) δ 11.59 (1 H, s), 9.80-9.97 (2 H, m), 8.46 (1 H, d, J=2.02 Hz), 7.69-7.84 (4 H, m), 7.60 (1 H, d, J=15.41 Hz), 7.48 (1 H, d, J=7.58 Hz), 7.23-7.41 (4 H, m), 7.00 (1 H, d, J=15.16 Hz), 5.95 (1 H, s), 4.37 (1 H, ddd, J=12.32, 5.37, 5.05 Hz), 3.83-3.91 (1 H, m), 3.70 (3 H, s), 3.18-3.24 (1 H, m), 2.91-3.03 (1 H, m) ppm. MS (ESI) m/z: 599 (M+H)$^+$. Analytical HPLC: RT=8.77 min.

Example 19

(S,Z)-4-(2-(3-(5-Chloro-2-(1H-tetrazol-1-yl)phenyl)-2-fluoroacryloyl)-1,2,3,4-tetrahydroisoquinoline-1-carboxamido)benzoic acid

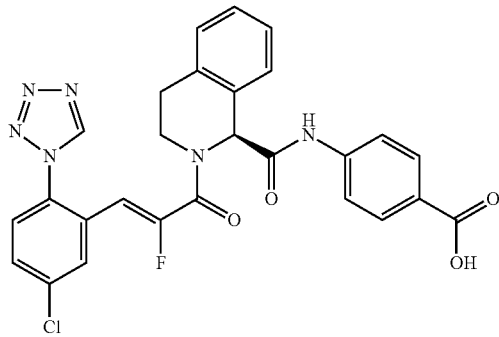 [SMILES: O=C(O)c1ccc(NC(=O)[C@@H]2c3ccccc3CCN2C(=O)/C(F)=C/c2cc(Cl)ccc2-n2cnnn2)cc1]

19A: (E) and (Z)-ethyl 3-(5-chloro-2-(1H-tetrazol-1-yl)phenyl)-2-fluoroacrylate: To a cold (−78° C.) THF solution of ethyl 2-(diethoxyphosphoryl)-2-fluoroacetate (0.28 g, 1.15 mmol) was added 1M isopropylmagnesium bromide (1.15 mL, 1.15 mmol) via syringe. The reaction mixture was stirred cold for 0.5 h followed by the addition of a THF solution of 5-chloro-2-(1H-tetrazol-1-yl)benzaldehyde (0.241 g, 1.15 mmol). Reaction mixture was stirred cold for 1.5 h, then ice bath was removed and stirred at rt for 1 h. The reaction was then heated to reflux for 1 h. The reaction was quenched with 1N HCl and extracted with EtOAc, dried and evaporated to give 0.26 g of desired product as yellow oil. NMR shows a 1:1 mixture of E/Z isomers which were separated after hydrolysis and coupling.

19B: (E) and (Z)-3-(5-chloro-2-(1H-tetrazol-1-yl)phenyl)-2-fluoroacrylic acid: 19A (0.26 g, 0.876 mmol) was dissolved in THF. To this was added LiOH (0.06 g, 2.63 mmol) followed by an equal volume of H$_2$O. The reaction mixture was stirred at rt for 1 h. Quenched the reaction mixture with dilute HCl and extracted organics with EtOAc (2×100 mL), dried and evaporated to a white solid.

Example 19: Example 19 was made in a similar manner as Example 3 using 19B and isolated during HPLC purification: $^1$H NMR (400 MHz, MeOD) δ 9.21 (1 H, br. s), 8.21-8.27 (1 H, m), 6.70 (1 H, s), 6.63 (2 H, d, J=8.59 Hz), 6.28-6.37 (4 H, m), 6.18 (1 H, br. s), 5.96 (3 H, br. s), 5.00 (1 H, d, J=35.3 Hz), 4.35 (1 H, s), 2.86 (1 H, br. s), 2.45 (1 H, br. s), 1.52-1.64 (2 H, m) ppm. MS (ESI) m/z: 547.0 (M+H)$^+$. Analytical HPLC: RT=8.70 min.

Example 20

(E)-4-(2-(3-(5-Chloro-2-(1H-tetrazol-1-yl)phenyl)acryloyl)-6-methyl-1,2,3,4-tetrahydroisoquinoline-1-carboxamido)benzoic acid

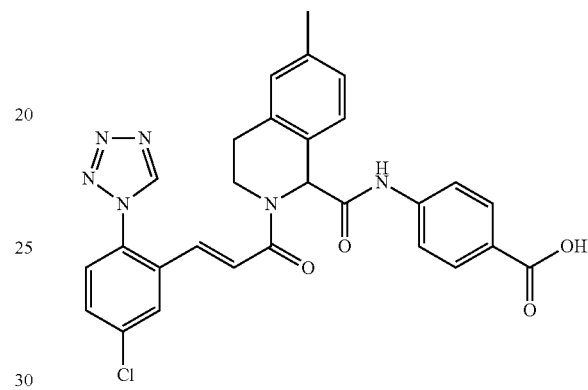

20A: 6-Methyl-1,2,3,4-tetrahydroisoquinoline: To 6-methylisoquinoline (0.562 g, 3.92 mmol) in EtOH (30 mL) was added 5% Pt/C (60 mg) and the mixture was hydrogenated at 55 psi for 24 h. The reaction was filtered through Celite® and concentrated to 0.55 g (95%) as clear oil. MS (ESI) m/z: 148.1 (M+H)$^+$.

20B: 6-Methyl-3,4-dihydroisoquinoline: To 20A (0.55 g, 3.74 mmol) in DCM (25 mL) was added MnO$_2$ (6.88 g, 67.2 mmol). After 4 h, the reaction was filtered through Celite® and concentrated to afford 0.51 g (94%) of yellow oil. MS (ESI) m/z: 146 (M+H)$^+$.

20C: (E)-Methyl 4-(2-(3-(5-chloro-2-(1H-tetrazol-1-yl)phenyl)acryloyl)-6-methyl-1,2,3,4-tetrahydroisoquinoline-1-carboxamido)benzoate: To 20B (0.15 g, 1.033 mmol), methyl 4-isocyanobenzoate (0.166 g, 1.033 mmol), and Intermediate 2 (0.259 g, 1.033 mmol) was added MeOH (20 mL). The reaction was heated to reflux for 24 h. After cooling to rt the product was filtered off as (0.318 g, 55.3%) a yellow solid. MS (ESI) m/z: 557.0 (M+H)$^+$.

Example 20: To ice cold solution of 20C (0.1 g, 0.180 mmol) in THF/H$_2$O (15 mL) was added LiOH (0.023 g, 0.539 mmol). After 2 h, the reaction was acidified with 1N HCl and extracted with EtOAc (3×15 mL), brine (10 mL) and dried (MgSO$_4$). Purification by reverse phase HPLC and freeze-drying afforded 14 mg (14%) of desired product as white solid. $^1$H NMR (400 MHz, MeOD) δ 8.23 (1 H, s), 6.90 (1 H, s), 6.65 (2 H, d, J=8.34 Hz), 6.32-6.43 (3 H, m), 6.28 (1 H, d, J=8.34 Hz), 6.01-6.15 (2 H, m), 5.88 (1 H, d, J=15.4 Hz), 5.76-5.84 (2 H, m), 4.48 (1 H, s), 2.94-3.06 (1 H, m), 2.52 (1 H, br. s), 1.54-1.68 (2 H, m), 1.03 (3 H, s) ppm. MS (ESI) m/z: 543.0 (M+H)$^+$. Analytical HPLC: RT=8.36 min.

Example 21

(E)-4-(3-Amino-6-(3-(5-chloro-2-(1H-tetrazol-1-yl)phenyl)acryloyl)-8,8-dimethyl-5,6,7,8-tetrahydro-1,6-naphthyridine-5-carboxamido)benzoic acid, bis TFA Salt

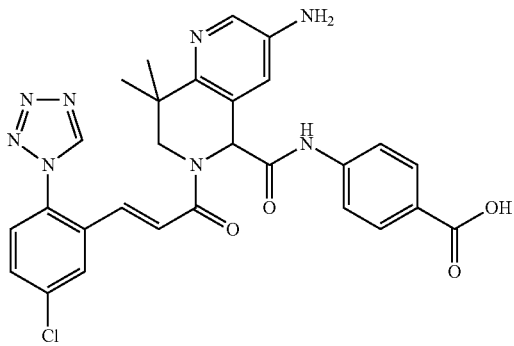 [SMILES: CC1(C)CN(C(=O)/C=C/c2cc(Cl)ccc2-n2cnnn2)C(C(=O)Nc2ccc(C(=O)O)cc2)c2cc(N)cnc21]

21A: 8,8-Dimethyl-3-nitro-5,6,7,8-dihydro-1,6-naphthyridine: To a solution of t-butyl 8,8-dimethyl-3-nitro-7,8-dihydro-1,6-naphthyridine-6 (5H)-carboxylate (1 g, 3.0 mmol) in DCM (10 mL) at 0° C., HCl in Dioxane (1 mL) was added. After 1 h, the reaction mixture was concentrated and made basic. The aqueous layer was extracted with DCM and the combined layers were washed with H$_2$O, brine, dried (Na$_2$SO$_4$), filtered and concentrated to afford 0.60 g of 21A. The crude product was taken to next step without further purification. MS (ESI) m/z: 207 (M+H)$^+$.

21B: 8,8-Dimethyl-3-nitro-7,8-dihydro-1,6-naphthyridine: To a solution of 21A (0.4 g, 0.2 mmol) in DCM (4 mL), added mercuric (II) oxide followed by iodine at 0° C. After 1 h at rt, the reaction mixture was quenched with H$_2$O then extracted with DCM. The combined organic layers were washed with H$_2$O, brine, Na$_2$S2O3, dried (Na$_2$SO$_4$) and concentrated to give 0.3 g of 21B. MS (ESI) m/z: 205 (M+H)$^+$.

21C: (E)-tert-Butyl 4-(6-(3-(5-chloro-2-(1H-tetrazol-1-yl)phenyl)acryloyl)-8,8-dimethyl-3-nitro-5,6,7,8-tetrahydro-1,6-naphthyridine-5-carboxamido)benzoate: 21C was prepared by the Ugi reaction as in Example 20 using 21B and Intermediates 2 and 6 to afford 0.1 g of desired product. MS (ESI) m/z: 764 (M+H)$^+$.

21D: (E)-tert-Butyl4-(3-amino-6-(3-(5-chloro-2-(1H-tetrazol-1-yl)phenyl)acryloyl)-8,8-dimethyl-5,6,7,8-tetrahydro-1,6-naphthyridine-5-carboxamido)benzoate: To a solution of 21C (0.1 g 0.15 mmol) in EtOH (4 mL) at 0° C. was added ammonium chloride, after 5 min, indium powder was added and reaction was heated to reflux for 3 h. The reaction mixture was filtered through Celite® and concentrated. Water was added to the residue and it was extracted with EtOAc twice. The combined organic layers were washed with saturated NaHCO$_3$ solution, H$_2$O, brine, dried (Na$_2$SO$_4$), filtered and concentrated to give 0.08 g of 21D. MS (ESI) m/z: 630 (M+H)$^+$.

Example 21: To 21D (0.08 g) in DCM (1 mL) was added TFA (0.1 mL). After 4 h, the reaction mixture was concentrated and purified by reverse phase HPLC and freeze-dried to afford 0.01 g of Example 21 as a white solid. $^1$H NMR (400 MHz, DMSO-d$_6$) δ 12.76 (1 H, bs), 10.91 (1 H, s), 9.87 (1 H, s), 8.46 (1 H, d, J=2.4 Hz), 7.86-7.91 (2 H, m), 7.71-7.78 (4 H, m), 7.58 (1 H, d, J=15.2 Hz), 6.54-7.21 (3 H, m), 5.87 (1 H, s), 4.26 (1 H, d, J=14.0 Hz), 3.91 (1 H, d, J=12.8 Hz), 1.38 (3 H, s), 1.24 (3 H, s). MS (ESI) m/z: 573 (M+H)$^+$. Analytical HPLC: RT=6.41 min

Example 22

(E)-4-(3-chloro-6-(3-(5-chloro-2-(1H-tetrazol-1-yl)phenyl)acryloyl)-8,8-dimethyl-5,6,7,8-tetrahydro-1,6-naphthyridine-5-carboxamido)benzoic acid, TFA Salt

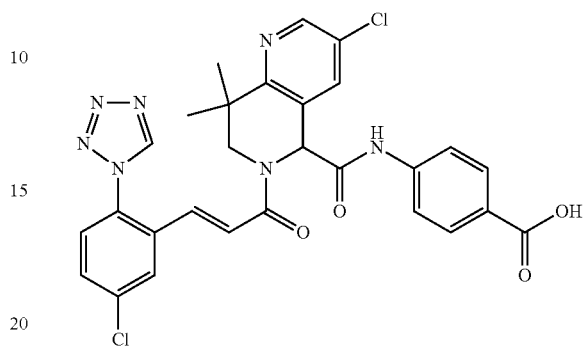

22A: tert-butyl 3-chloro-8,8-dimethyl-7,8-dihydro-1,6-naphthyridine-6(5H)-carboxylate: To copper chloride (0.089 g, 0.9 mmol) in ACN (1 mL) at 0° C., was added isopentyl nitrite (105 mg, 0.9 mmol). Then tert-butyl 3-amino-8,8-dimethyl-7,8-dihydro-1,6-naphthyridine-6(5H)-carboxylate (0.089 g, 1.36 mmol) in ACN (1 mL) was added. After 4 h at rt, the reaction mixture was concentrated and purified by column chromatography to afford 0.06 g of 22A. MS (ESI) m/z: 296 (M+H)$^+$.

Example 22: 22A was deprotected and oxidized in a similar manner as described previously and carried onto an Ugi reaction with Intermediates 2 and 6 as in Example 20 followed by TFA deprotection and purification to afford 7 mg of Example 22 as a white solid. $^1$H NMR (400 MHz, DMSO-d$_6$) δ 12.8 (1 H, b s), 10.8 (1 H, s), 9.88 (1 H, s), 8.59 (1 H, d, J=2.0 Hz), 8.47 (1 H, d, J=2.0 Hz), 7.99 (1 H, d, J=2.0 Hz), 7.92 (2 H, d, J=8.0 Hz), 7.70-7.80 (4 H, m), 7.63 (1H, d, J=15.2 Hz), 7.03-7.08 (1 H, m), 6.54 (1 H, bs), 6.07 (1 H, s), 4.38 (1 H, d, J=16.0 Hz), 3.96 (1 H, d, J=14.0 Hz), 1.46 (3 H, s), 1.22 (3 H, s) ppm. MS (ESI) m/z: 592 (M+H)$^+$. Analytical HPLC: RT=17.7 min.

Example 23

(E)-5-(4-Carbamoylphenyl)-2-(3-(3-chloro-2-fluoro-6-(1H-tetrazol-1-yl)phenyl)acryloyl)-N-(1H-indazol-6-yl)-1,2,3,4-tetrahydro-2,6-naphthyridine-1-carboxamide, TFA salt

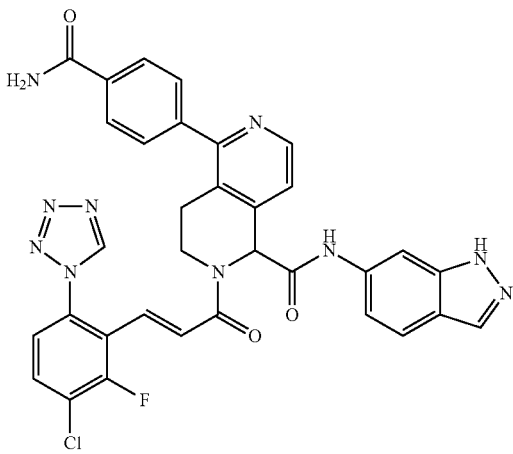 [SMILES: NC(=O)c1ccc(-c2nccc3c2CCN(C(=O)/C=C/c2c(-n4cnnn4)ccc(Cl)c2F)C3C(=O)Nc2ccc3cn[nH]c3c2)cc1]

23A: 4-(6-Benzyl-5,6,7,8-tetrahydro-2,6-naphthyridin-1-yl)benzamide: 2-benzyl-5-chloro-1,2,3,4-tetrahydro-2,6-naphthyridine (100 mg, 0.339 mmol), 4-carbamoylphenylboronic acid (61.5 mg, 0.373 mmol) and $K_2CO_3$ (61.5 mg, 0.373 mmol) were combined in a microwave reaction tube. Added toluene (2.5 mL) and EtOH (0.5 mL) and the resulting suspension was degassed. Tetrakistriphenyl phosphine palladium (0) (3.91 mg, 3.39 µmol) was added and the reaction was heated in a microwave for 15 min at 130° C. The mixture was diluted with DCM (10 mL) and washed with $H_2O$ (5 mL) and brine (5 mL). The organic portion was dried over $MgSO_4$, filtered and concentrated. Purified by flash chromatography to give 23A (82 mg, 71%) as an off-white solid. MS (ESI) m/z: 344 $(M+H)^+$.

23B: 4-(5,6,7,8-Tetrahydro-2,6-naphthyridin-1-yl)benzamide: To 23A (56 mg, 0.147 mmol) in MeOH (2 mL), palladium on carbon (12 mg, 0.011 mmol) was added and the reaction vessel was placed under hydrogen gas (1 atm) and stirred for 18 h. The reaction mixture was filtered under argon, the filtrate was concentrated and dried to give 23B (37 mg, 99% yield) as a brown oil. MS (ESI) m/z: 254 $(M+H)^+$.

Example 23: 23B was oxidized and then subjected to Ugi reaction using intermediate 3A and intermediate 8 as with Example 20. $^1$H NMR (500 MHz, DMSO-$d_6$) δ 12.91 (1 H, br. s), 10.78 (1 H, s), 9.86 (1 H, s), 8.58 (1 H, d, J=4.95 Hz), 7.90-8.11 (6 H, m), 7.62-7.76 (5 H, m), 7.43 (1 H, br. s), 7.19 (1 H, dd, J=8.80, 1.65 Hz), 7.15 (1 H, d, J=15.68 Hz), 6.98 (1 H, d, J=15.68 Hz), 5.98 (1 H, s), 4.00-4.07 (1 H, m), 3.77-3.83 (1 H, m), 2.94-3.12 (2 H, m) ppm. MS (ESI) m/z: 663 $(M+H)^+$. Analytical HPLC: RT=5.43 min.

Example 24

(E)-2-(3-(3-Chloro-2-fluoro-6-(1H-tetrazol-1-yl)phenyl)acryloyl)-N-(1H-indazol-6-yl)-5-(4-methylpiperazin-1-yl)-1,2,3,4-tetrahydro-2,6-naphthyridine-1-carboxamide, bis TFA salt

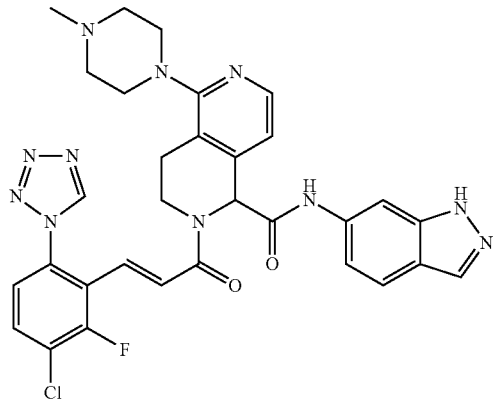 [SMILES: CN1CCN(c2nccc3c2CCN(C(=O)/C=C/c2c(-n4cnnn4)ccc(Cl)c2F)C3C(=O)Nc2ccc3cn[nH]c3c2)CC1]

24A: 2-Benzyl-5-(4-methylpiperazin-1-yl)-1,2,3,4-tetrahydro-2,6-naphthyridine: 2-Benzyl-5-chloro-1,2,3,4-tetrahydro-2,6-naphthyridine (120 mg, 0.464 mmol) was partially suspended in 1-methylpiperazine (500 µL, 0.464 mmol) and the mixture was heated at 160° C. for 40 h. The solvent was removed in vacuo and the residue was dissolved in DCM (10 mL) and washed with $H_2O$ (5 mL). The organic portion was dried over anhydrous $MgSO_4$, filtered and concentrated. The crude product was purified by silica gel chromatography to provide 24A (139 mg, 93%). MS (ESI) m/z: 323 $(M+H)^+$.

24B: 5-(4-Methylpiperazin-1-yl)-1,2,3,4-tetrahydro-2,6-naphthyridine: To a solution of DIEA (89 uL, 0.508 mmol) in DCM (677 uL) was added 24A. The mixture was cooled to 0° C. and 1-chloroethyl chloroformate (23.78 uL, 0.220 mmol) was added dropwise. The reaction mixture was stirred at 0° C. for 1 h and then warmed to rt and stirred for 18 h. The solvent was removed in vacuo and the crude was redissolved in EtOH (1 mL) and heated at reflux for 3 h. Concentrated in vacuo and added DCM (5 mL) and 1 N HCl (10 mL). The aqueous layer was removed and adjusted to pH 12 by adding 10 N NaOH. Extracted with DCM and the combined organic layers were dried over anhydrous $MgSO_4$, filtered and concentrated to provide the 24B (19 mg, 66%). MS (ESI) m/z: 233 $(M+H)^+$.

24C: 5-(4-Methylpiperzin-1-yl)-3,4-dihydro-2,6-napthyridine: 24C was prepared from 24B as described in Example 20B. MS (ESI) m/z: 231 $(M+H)^+$.

Example 24 was prepared from 24C, intermediate 3A and intermediate 8 following the procedure used to prepare Example 20. $^1$H NMR (500 MHz, MeOD) δ 9.55 (1 H, s), 8.20 (1 H, d, J=5.50 Hz), 8.01 (1 H, s), 7.97 (1 H, s), 7.80 (1 H, t, J=8.12 Hz), 7.70 (1 H, d, J=8.80 Hz), 7.49 (1 H, dd, J=8.67, 1.24 Hz), 7.26 (1 H, d, J=5.23 Hz), 7.10-7.17 (2 H, m), 6.95-7.02 (1 H, m), 5.84 (1 H, s), 4.08 (1 H, ddd, J=12.52, 6.88, 4.54 Hz), 3.66-3.77 (3 H, m), 3.56-3.65 (2 H, m), 3.33-3.46 (3 H, m), 3.10-3.29 (4 H, m), 2.99 (3 H, s), 2.88-2.96 (1 H, m) ppm. MS (ESI) m/z: 642 $(M+H)^+$. Analytical HPLC: RT=4.73 min.

Example 25

(E)-2-(3-(5-Chloro-2-(1H-tetrazol-1-yl)phenyl)acryloyl)-5-(2-(dimethylamino)ethylamino)-N-(1H-indazol-6-yl)-1,2,3,4-tetrahydro-2,6-naphthyridine-1-carboxamide, bis TFA salt

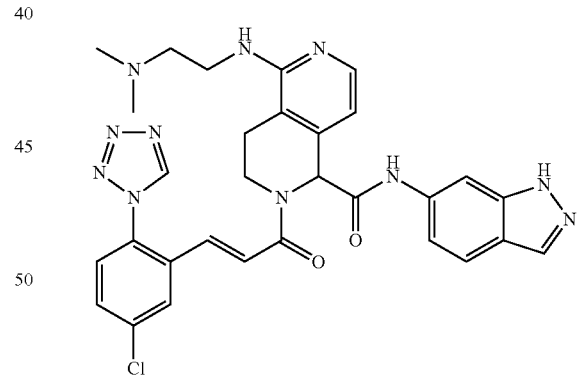

Example 25 was prepared in a similar manner as Example 24 using 2-benzyl-5-bromo-1,2,3,4-tetrahydro-2,6-naphthyridine (Patent WO 03076427) and N,N-dimethylaminoethylamine. $^1$H NMR (500 MHz, MeOD) δ 9.53 (1 H, s), 8.19 (1 H, d, J=1.93 Hz), 8.01-8.07 (1 H, m), 7.94-8.00 (2 H, m), 7.71 (1 H, d, J=8.80 Hz), 7.68 (1 H, dd, J=8.53, 2.48 Hz), 7.59 (1 H, d, J=8.25 Hz), 7.30-7.36 (1 H, m), 7.19-7.25 (1 H, m), 7.15 (1 H, d, J=8.53 Hz), 6.91 (1 H, d, J=5.78 Hz), 5.96 (1 H, s), 4.26-4.33 (1 H, m), 4.15-4.23 (1 H, m), 3.73-3.89 (2 H, m), 3.39-3.43 (2 H, m), 2.98 (6 H, s), 2.72-2.87 (2H, m) ppm. MS (ESI) m/z: 612 $(M+H)^+$. Analytical HPLC: RT=4.19 min.

Example 26

(E)-2-(3-(5-Chloro-2-(1H-tetrazol-1-yl)phenyl)acryloyl)-N-(1H-indazol-6-yl)-5-morpholino-1,2,3,4-tetrahydro-2,6-naphthyridine-1-carboxamide, TFA Salt

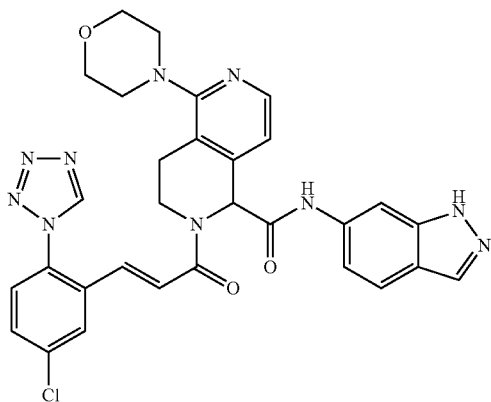 [SMILES: O=C(Nc1ccc2cn[nH]c2c1)C1c2ccnc(N3CCOCC3)c2CCN1C(=O)/C=C/c1cc(Cl)ccc1-n1cnnn1]

Example 26 was prepared in a similar manner as Example 24 using morpholine. $^1$H NMR (400 MHz, MeOD) δ 9.53 (1 H, s), 8.19 (1 H, d, J=2.01 Hz), 8.12 (1 H, d, J=5.77 Hz), 7.95-8.03 (2 H, m), 7.65-7.72 (2 H, m), 7.56-7.61 (1 H, m), 7.29-7.37 (2 H, m), 7.16-7.23 (1 H, m), 7.13 (1 H, d, J=8.03 Hz), 5.93 (1 H, s), 4.17-4.24 (1 H, m), 3.89 (5 H, d, J=4.27 Hz), 3.33-3.39 (4 H, m), 3.11-3.18 (1 H, m), 2.97-3.06 (1 H, m) ppm. MS (ESI) m/z: 611 (M+H)$^+$. Analytical HPLC: RT=5.72 min.

Example 27

(E)-4-(2-(3-(3-Chloro-2-fluoro-6-(1H-tetrazol-1-yl)phenyl)acryloyl)-5-(3-oxomorpholino)-1,2,3,4-tetrahydro-2,6-naphthyridine-1-carboxamido)benzoic acid

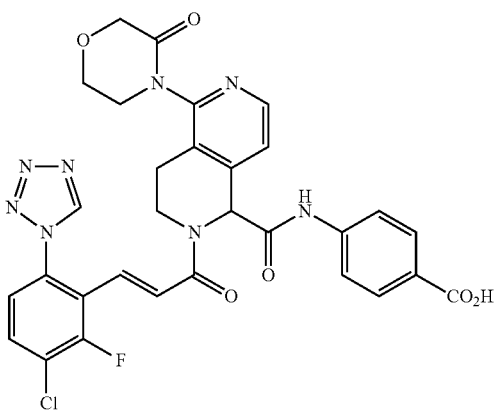 [SMILES: O=C(O)c1ccc(NC(=O)C2c3ccnc(N4CCOCC4=O)c3CCN2C(=O)/C=C/c2c(-n3cnnn3)ccc(Cl)c2F)cc1]

27A: 4-(6-Benzyl-5,6,7,8-tetrahydro-2,6-naphthyridin-1-yl)morpholin-3-one: To a mixture of 2-benzyl-5-bromo-1,2,3,4-tetrahydro-2,6-naphthyridine (64 mg, 0.211 mmol) and morpholin-3-one (21.34 mg, 0.211 mmol) was added DMSO (4 mL), 1,10-phenanthroline (3.80 mg, 0.021 mmol) and K$_2$CO$_3$ (72.9 mg, 0.528 mmol). The mixture was degassed and copper (I) iodide (8.04 mg, 0.042 mmol) was added and the reaction was heated at 130° C. for 18 h. The reaction mixture was diluted with H$_2$O (10 mL) and extracted with EtOAc (2×5 mL). The organic portion was dried over anhydrous MgSO$_4$, filtered and concentrated. The crude product was purified by flash chromatography followed by reverse phase HPLC to give 27A (20 mg, 29%) as a yellow oil. MS (ESI) m/z: 324 (M+H)$^+$.

Example 27: 27A was transformed to the imine as described in the previous examples and carried onto the Ugi reaction as previously described to produce Example 27. $^1$H NMR: Several rotamers observed. MS (ESI) m/z: 647 (M+H)$^+$. Analytical HPLC: RT=6.75 min.

Example 28

(E)-4-(2-(3-(3-Chloro-2-fluoro-6-(1H-tetrazol-1-yl)phenyl)acryloyl)-5-morpholino-1,2,3,4-tetrahydro-2,6-naphthyridine-1-carboxamido)benzoic acid, TFA Salt

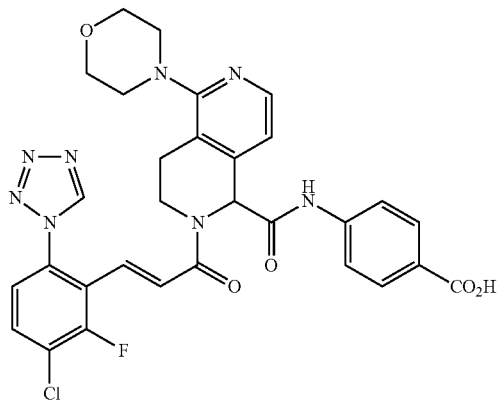 [SMILES: O=C(O)c1ccc(NC(=O)C2c3ccnc(N4CCOCC4)c3CCN2C(=O)/C=C/c2c(-n3cnnn3)ccc(Cl)c2F)cc1]

Example 28 was prepared in a similar manner as Example 27 substituting intermediate 6 for intermediate 8. $^1$H NMR (500 MHz, DMSO-d$_6$) δ 10.87 (1 H, s), 9.86 (1 H, s), 8.15 (1 H, d, J=5.23 Hz), 7.96 (1 H, t, J=8.25 Hz), 7.88 (2 H, d, J=8.80 Hz), 7.64-7.71 (3 H, m), 7.21 (1 H, d, J=5.23 Hz), 7.15 (1 H, d, J=15.96 Hz), 6.95 (1 H, d, J=15.68 Hz), 5.75 (1 H, s), 4.00-4.07 (1 H, m), 3.72-3.79 (4 H, m), 3.65-3.71 (1 H, m), 3.02-3.17 (4 H, m), 2.96-3.03 (1 H, m), 2.85 (1 H, td, J=10.80, 4.81 Hz) ppm. MS (ESI) m/z: 633.0 (M+H)$^+$. Analytical HPLC: RT=5.44 min.

Example 29

(E)-4-(2-(3-(3-Chloro-2-fluoro-6-(1H-tetrazol-1-yl)phenyl)acryloyl)-5-(2-oxopiperidin-1-yl)-1,2,3,4-tetrahydro-2,6-naphthyridine-1-carboxamido)benzoic acid, TFA Salt

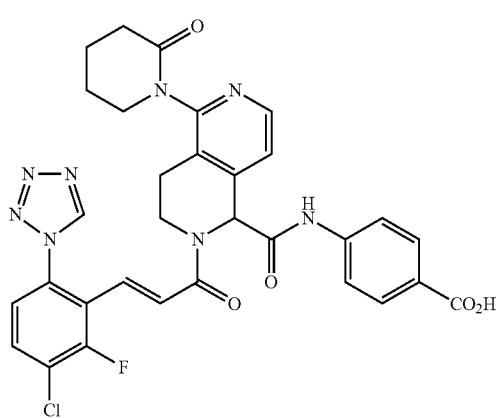 [SMILES: O=C(O)c1ccc(NC(=O)C2c3ccnc(N4CCCCC4=O)c3CCN2C(=O)/C=C/c2c(-n3cnnn3)ccc(Cl)c2F)cc1]

Example 29 was prepared in a similar manner as Example 27 substituting piperidin-2-one for morpholin-3-one. ¹H NMR: Several rotamers observed. MS (ESI) m/z: 645 (M+H)⁺. Analytical HPLC: RT=6.61 min.

The following examples in Table 2 were made by the Ugi reaction as described in 24, using Intermediate 2, Intermediate 3A, the corresponding imine intermediates, made in a similar manner as Intermediate 3, from commercially available isoquinolines and methyl 4-isocyanobenzoate, Intermediate 6, Intermediate 11, isocyanobenzene or 1-fluoro-4-isocyanobenzene. Methyl esters were hydrolyzed as in Example 20 or t-butyl esters were removed with TFA in DCM as previously described.

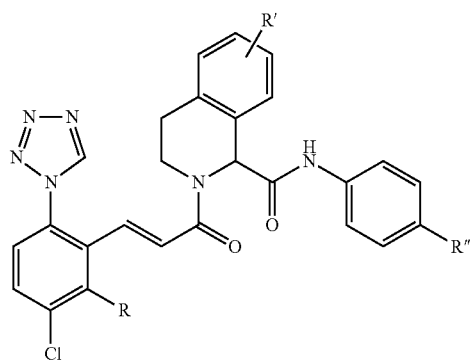

TABLE 2

| Example # | R | R' | R" | M + H | RT |
|---|---|---|---|---|---|
| 30 | H | 7-F | CO2Me | 561.0 | 7.04* |
| 31 | H | 7-F | COOH | 547.0 | 6.55* |
| 32 | H | 7-Me | CO2Me | 557.0 | 9.57 |
| 33 | H | 7-Me | COOH | 543.0 | 8.53 |
| 34 | H | 7-CO2Me | COOH | 587.2 | 7.92 |
| 35 | H | 6-CO2Me | COOH | 587.2 | 7.56 |
| 36 | H | 7-CN | COOH | 553.8 | 8.42 |
| 37 | H | 8-CO2Me | COOH | 586.9 | 9.03 |
| 38 | H | H | F | 503.0 | 9.82 |
| 39 | H | 6-CONHPh | COOH | 587.2 | 7.87 |

*method B

Example 40

(1S)-2-((E)-3-(5-Chloro-2-(1H-tetrazol-1-yl)phenyl) acryloyl)-N-(4-(pyrrolidin-2-yl)phenyl)-1,2,3,4-tetrahydroisoquinoline-1-carboxamide, TFA salt

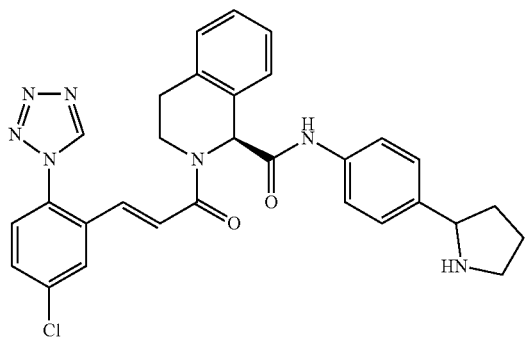 [SMILES: O=C(Nc1ccc(C2CCCN2)cc1)[C@@H]1c2ccccc2CCN1C(=O)/C=C/c1cc(Cl)ccc1-n1cnnn1]

Example 40 was prepared in a similar manner as Example 20 starting with tert-butyl 2-(4-aminophenyl)pyrrolidine-1-carboxylate. ¹H NMR (400 MHz, MeOD) δ 9.49-9.57 (1 H, m), 8.17 (1 H, d, J=2.27 Hz), 7.46-7.70 (5 H, m), 7.37-7.44 (2 H, m), 7.36 (1 H, d, J=12.88 Hz), 7.22-7.30 (3 H, m), 7.16 (1 H, d, J=15.41 Hz), 5.80 (1H, s), 4.52-4.62 (1 H, m), 4.29 (1 H, ddd, J=12.19, 5.37, 5.18 Hz), 3.82 (1 H, ddd, J=12.38, 8.84, 4.04 Hz), 3.39-3.50 (2 H, m), 3.23-3.31 (1 H, m), 2.94 (1 H, ddd, J=15.85, 4.86, 4.55 Hz), 2.36-2.46 (1 H, m), 2.11-2.34 (3 H, m) ppm. MS (ESI) m/z: 554.1 (M+H)⁺. Analytical HPLC: RT=5.72 min.

Example 41

(S,E)-N-(3-amino-1H-indazol-6-yl)-2-(3-(5-chloro-2-(1H-tetrazol-1-yl)phenyl)acryloyl)-1,2,3,4-tetrahydroisoquinoline-1-carboxamide, TFA salt

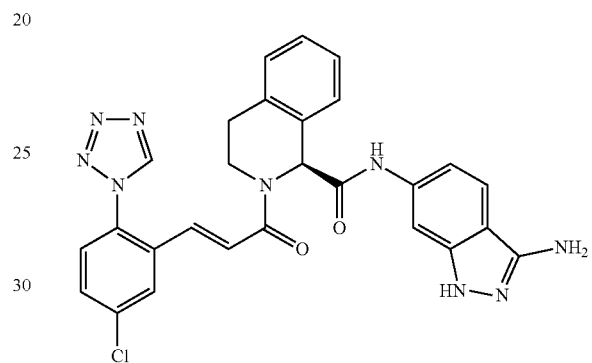

41A: 4-Amino-2-fluorobenzonitrile: 2-fluoro-4-nitrobenzonitrile (0.125 g, 0.751 mmol) was hydrogenated at 50 psi in the presence of 10% Pd/C (40 mg) in EtOH/EtOAc (15 mL) for 1 h. Filtered through Celite® and concentrated to an orange solid that was carried onto next step. MS (ESI) m/z: 137 (M+H)⁺.

41B: (S)-(9H-fluoren-9-yl)methyl 1-(4-cyano-3-fluorophenylcarbamoyl)-3,4-dihydro isoquinoline-2(1H)-carboxylate: 41A was combined with (S)-2-(((9H-fluoren-9-yl)methoxy)carbonyl)-1,2,3,4-tetrahydroisoquinoline-1-carboxylic acid (0.3 g, 0.751 mmol) in DCM (5 mL) and cooled in ice/acetone bath. Pyridine (0.304 mL, 3.76 mmol) and POCl₃ (0.070 mL, 0.751 mmol) were added. After 45 min, the reaction was partitioned with dilute HCl (20 mL) and EtOAc (70 mL). The organic layer was washed with brine (10 mL) and dried (MgSO₄). Purification by normal phase chromatography afforded the desired product as (0.38 g, 98%) a white foam. MS (ESI) m/z: 518.1 (M+H)⁺.

41C: (S)—N-(3-Amino-1H-indazol-6-yl)-1,2,3,4-tetrahydroisoquinoline-1-carboxamide: To 41B (0.13 g, 0.251 mmol) in EtOH (10 mL) was added hydrazine hydrate (0.063 mL, 2.009 mmol) and the reaction was heated at 160° C. for 35 min in microwave. The solvents were removed and crude product used in next step. MS (ESI) m/z: 308.3 (M+H)⁺.

Example 41: To crude 41C (0.077 g, 0.251 mmol) and Intermediate 1 (0.087 g, 0.251 mmol) was added DMF (1 mL) and DIEA (0.131 mL, 0.752 mmol). No desired product was detected. Added Intermediate 2 (0.063 g, 0.251 mmol) and 50% T3P in EtOAc (0.071 mL, 0.251 mmol). The reaction was partitioned with H₂O (10 mL) and EtOAc (40 mL). The organic layer was washed with brine (10 mL) and dried (MgSO₄). Purified by reverse phase HPLC and freeze-dried to afford 24 mg (14%) as pale yellow solid. ¹H NMR (400 MHz, MeOD) δ 9.53 (1 H, s), 8.19 (1 H, d, J=2.27 Hz), 7.94 (1 H, s), 7.84 (1 H, d, J=9.09 Hz), 7.67 (1H, d, J=2.27 Hz), 7.55-7.62 (1 H, m), 7.52 (1 H, d, J=5.56 Hz), 7.38 (1 H, d, J=15.41 Hz), 7.25-7.33 (3 H, m), 7.12-7.24 (2 H, m), 5.82 (1 H, s), 4.33 (1 H, ddd, J=12.13, 5.31, 5.05 Hz), 3.73-3.89 (1H, m), 3.32-3.41 (1 H, m), 2.97 (1H, dt, J=15.60, 4.58 Hz) ppm. MS (ESI) m/z: 540.0 (M+H)⁺. Analytical HPLC: RT=5.81 min.

Example 42

(S,E)-Methyl 4-(2-(3-(5-chloro-2-(1H-tetrazol-1-yl)phenyl)acryloyl)-1,2,3,4-tetrahydroisoquinoline-1-carboxamido)benzylcarbamate

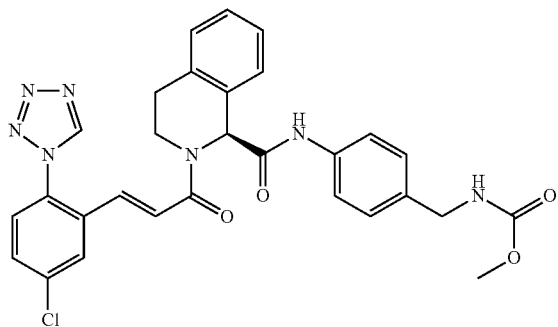 [SMILES: COC(=O)NCc1ccc(NC(=O)[C@@H]2c3ccccc3CCN2C(=O)/C=C/c2cc(Cl)ccc2-n2cnnn2)cc1]

42A: Methyl 4-nitrobenzylcarbamate: To (4-nitrophenyl)methanamine, HCl (0.075 g, 0.398 mmol) in DCM (6 mL), cooled to 0° C., was added pyridine (1 mL) and methyl chloroformate (0.031 mL, 0.398 mmol). After 24 h, quenched with H₂O (20 mL), extracted with DCM (3×20 mL), washed with brine (15 mL) and dried (MgSO₄). Collected 35 mg of 42A. MS (ESI) m/z: 211.0 (M+H)⁺.

42B: Methyl 4-aminobenzylcarbamate: 42A (35 mgs, 0.16 mmol) was hydrogenated at 50 psi in the presence of 10% Pd/C (10 mg) in EtOH (10 mL). Filtered through Celite® and concentrated to afford 42B. MS (ESI) m/z: 181 (M+H)⁺.

42C: (S)-Methyl 4-(1,2,3,4-tetrahydroisoquinoline-1-carboxamido) benzylcarbamate, TFA salt: To 42B in EtOAc (6 mL) was added (S)-2-(((9H-fluoren-9-yl)methoxy)carbonyl)-1,2,3,4-tetrahydroisoquinoline-1-carboxylic acid (0.09 g, 0.225 mmol), DIEA (0.104 mL, 0.596 mmol) and 50% T3P in EtOAc (0.112 mL, 0.398 mmol). After 24 h, to the reaction was added TBAF (0.398 mL, 0.398 mmol)/THF and DMF (1 mE). After 30 min., the reaction was partitioned with H₂O (10 mL) and EtOAc (30 mL). The organic layer was washed with brine (10 mL) and dried (MgSO₄). Purification by reverse phase HPLC afforded 48 mg of 42C as clear oil. MS (ESI) m/z: 340 (M+H)⁺.

Example 42: To 42C (30 mg, 0.088 mmol) in DMF (1.5 mL) was added Intermediate 1 (49 mg, 0.141 mmol) and DIEA (46.3 μL, 0.265 mmol). After 24 h, the reaction was purified by reverse phase HPLC and freeze-dried to afford 3.1 mg (6.1%) of a white solid. ¹H NMR (400 MHz, DMSO-d₆) δ 10.45 (1 H, s), 9.87 (1 H, s), 8.44 (1H, d, J=2.02 Hz), 7.68-7.82 (2 H, m), 7.45-7.66 (4 H, m), 7.21-7.32 (2 H, m), 7.15 (1H, d, J=8.34 Hz), 6.95 (1 H, d, J=15.41 Hz), 5.81 (1 H, s), 4.26-4.38 (1 H, m), 4.10 (2 H, d, J=6.06 Hz), 3.87-3.98 (1 H, m), 3.53 (3 H, s), 3.17 (1 H, d, J=18.95 Hz), 2.93 (1H, br. s), 2.67 (1 H, d, J=1.77 Hz) ppm. MS (ESI) m/z: 572.0 (M+H)⁺. Analytical HPLC: RT=8.22 min.

Example 43

Methyl 2-(4-((S)-2-((E)-3-(5-chloro-2-(1H-tetrazol-1-yl)phenyl) acryloyl)-1,2,3,4-tetrahydroisoquinoline-1-carboxamido)phenyl)pyrrolidine-1-carboxylate

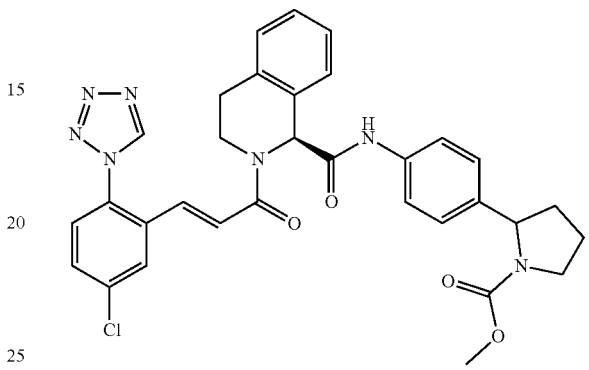

Example 43: To Example 40 (20 mg, 0.030 mmol) in DCM (1.5 mL) was added DIEA (5.21 μL, 0.030 mmol) and methyl chloroformate (2.319 μL, 0.030 mmol). After 24 h, the reaction was concentrated and then purified by reverse phase HPLC and freeze-dried to afford 7.1 mg (37%) of desired product as a white solid. ¹H NMR (400 MHz, MeOD) δ 10.19 (1 H, br. s), 9.55 (1 H, s), 8.21 (1 H, d, J=2.02 Hz), 7.67-7.72 (1H, m), 7.59 (1 H, d, J=8.59 Hz), 7.49-7.54 (1 H, m), 7.43-7.49 (2 H, m), 7.37 (1 H, d, J=15.41 Hz), 7.25-7.33 (3 H, m), 7.20 (1H, d, J=15.41 Hz), 7.12 (2 H, br. s), 5.83 (1H, s), 4.26-4.36 (1 H, m), 3.89 (1 H, ddd, J=12.38, 8.46, 4.17 Hz), 3.48-3.72 (5 H, m), 3.27-3.32 (1 H, m), 2.92-3.00 (1 H, m), 2.31 (1 H, br. s), 1.77-1.97 (3 H, m) ppm. MS (ESI) m/z: 612.1 (M+H)+. Analytical HPLC: RT=8.94 min.

Example 44

(E)-4-(7-(benzyloxycarbonylamino)-2-(3-(5-chloro-2-(1H-tetrazol-1-yl)phenyl)acryloyl)-1,2,3,4-tetrahydroisoquinoline-1-carboxamido)benzoic acid

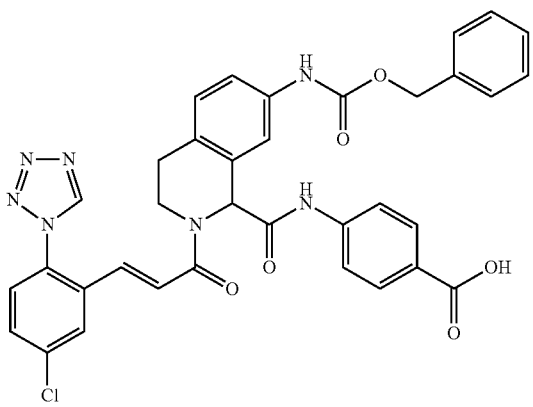 [SMILES: O=C(Nc1ccc2c(c1)C(C(=O)Nc1ccc(C(=O)O)cc1)N(C(=O)/C=C/c1cc(Cl)ccc1-n1cnnn1)CC2)OCc1ccccc1]

44A: tert-Butyl 7-(benzyloxycarbonylamino)-3,4-dihydroisoquinoline-2(1H)-carboxylate: To 1,2,3,4-tetrahydroisoquinolin-7-amine (0.5 g, 2.329 mmol) in DCM (50 mL) and saturated aqueous NaHCO$_3$ (20 mL) in a separatory funnel was added benzyl chloroformate (0.333 mL, 2.329 mmol). After 10 min, the layers were separated, washed with brine and dried (MgSO$_4$). Purification by normal phase chromatography afforded 0.619 g (62%) of 44A. MS (ESI) m/z: 383.0 (M+H)$^+$.

44B: Benzyl 1,2,3,4-tetrahydroisoquinolin-7-ylcarbamate: To 44A (0.61 g, 2.19 mmol) in DCM (30 mL) was added TFA (10 mL) and after 4 h, the reaction was concentrated. The reaction was partitioned with saturated aqueous NaHCO$_3$ (15 mL) and EtOAc (60 mL). The organic layer was washed with brine (10 mL) and dried (MgSO$_4$). Collected 0.61 g (93%) of 44B as a tan solid. MS (ESI) m/z: 283.0 (M+H)$^+$.

44C: 44C was prepared from 44B in a similar manner as Example 15. MS (ESI) m/z: 692.1 (M+H)$^+$.

Example 44: To 44C (54 mg, 0.078 mmol) in THF (2 mL)/H$_2$O (2 mL), cooled to 0° C., was added LiOH hydrate (13.10 mg, 0.312 mmol). After 3 h, the reaction was partitioned with 1N HCl (5 mL) and EtOAc (20 mL). The organic layer was washed with brine (10 mL) and dried (MgSO$_4$). The crude product was then purified by reverse phase HPLC. $^1$H NMR (400 MHz, MeOD) δ □9.54 (1H, s), 8.20 (1H, d, J=2.02 Hz), 7.96 (2 H, d, J=8.59 Hz), 7.76 (1 H, br. s), 7.63-7.71 (4 H, m), 7.58 (1 H, d, J=8.59 Hz), 7.28-7.42 (8 H, m), 7.16-7.22 (2 H, m), 5.83 (1 H, s), 5.16-5.20 (2 H, m), 4.21-4.31 (1 H, m), 3.90 (1 H, ddd, J=12.19, 8.27, 4.29 Hz), 3.18-3.25 (1 H, m), 2.90-2.96 (1 H, m) ppm. MS (ESI) m/z: 678.1 (M+H)$^+$. Analytical HPLC: RT=8.64 min.

Example 45

(S,E)-N-(4-(1H-imidazol-2-yl)phenyl)-2-(3-(3-chloro-2-fluoro-6-(1H-tetrazol-1-yl)phenyl)acryloyl)-1,2,3,4-tetrahydroisoquinoline-1-carboxamide, TFA Salt

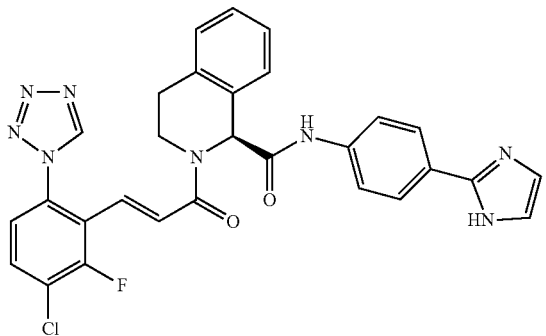 [SMILES: O=C(Nc1ccc(-c2ncc[nH]2)cc1)[C@@H]1c2ccccc2CCN1C(=O)/C=C/c1c(-n2cnnn2)ccc(Cl)c1F]

Example 45 was prepared in a similar manner as Example 42 using commercially available 4-(1H-imidazol-2-yl)aniline and Intermediate 3A. $^1$H NMR (400 MHz, MeOD) δ 9.56 (1 H, s), 7.84-7.91 (5 H, m), 7.81 (1 H, t, J=8.2 Hz), 7.61 (2 H, s), 7.48-7.57 (2 H, m), 7.26-7.35 (3 H, m), 7.13 (2 H, s), 5.83 (1 H, s), 4.11-4.27 (1 H, m), 3.62-3.75 (1 H, m), 2.96 (1 H, ddd, J=15.5, 4.5, 4.4 Hz) ppm. MS (ESI) m/z: 569.0 (M+H)+. Analytical HPLC: RT=5.72 min.

Example 46

(S,E)-N-(3-acetamido-1-methyl-1H-indazol-5-yl)-2-(3-(5-chloro-2-(1H-tetrazol-1-yl)phenyl)acryloyl)-1,2,3,4-tetrahydroisoquinoline-1-carboxamide

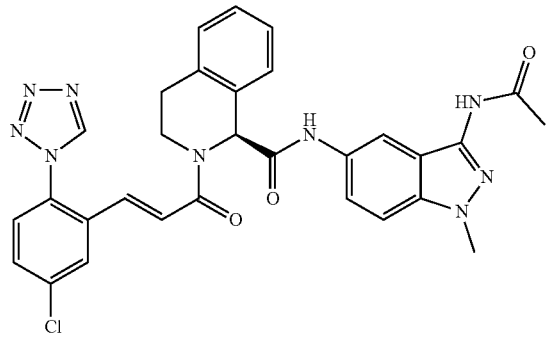 [SMILES: CC(=O)Nc1nn(C)c2ccc(NC(=O)[C@@H]3c4ccccc4CCN3C(=O)/C=C/c3cc(Cl)ccc3-n3cnnn3)cc12]

46A: 1-Methyl-5-nitro-1H-indazol-3-amine. To 2-fluoro-5-nitrobenzonitrile (1.9 g, 11.44 mmol) in EtOH (30 mL) was added methyl hydrazine (0.527 g, 11.44 mmol). The reaction was heated to 70° C. for 1 h. Cooled to rt and filtered off an orange-yellow solid that was washed with EtOH and dried to afford 1.89 g (86%) of 46A. MS (ESI) m/z: 193.0 (M+H)$^+$.

46B: N-(1-methyl-5-nitro-1H-indazol-3-yl)acetamide: To 46A (0.19 g, 0.989 mmol) in pyridine (5 mL) was added acetyl chloride (0.070 mL, 0.989 mmol). After 24 h, the reaction was concentrated and partitioned with dilute HCl (10 mL) and EtOAc (20 mL). Product was difficult to dissolve. The yellow solid was filtered and filtrate extracted. All product fractions were combined and purified by normal phase chromatography to afford 190 mg of desired product as bright yellow foam. MS (ESI) m/z: 235.0 (M+H)$^+$.

46C: N-(5-amino-1-methyl-1H-indazol-3-yl)acetamide: 46B was hydrogenated at 55 psi in EtOH (30 mL) with 10% Pd/C (40 mg). After 3 h, the reaction was filtered through Celite® and collected 0.15 g (74%) of 46C as an off-white solid. MS (ESI) m/z: 205 (M+H)$^+$.

Example 46: Example 46 was made from 46C in a similar manner as Example 20 using Intermediate 1. $^1$H NMR (400 MHz, MeOD) δ □9.52 (1 H, s), 8.15 (1 H, d, J=2.2 Hz), 7.90 (1 H, s), 7.63 (1 H, dd, J=8.2, 2.2 Hz), 7.49-7.58 (2 H, m), 7.38-7.45 (1 H, m), 7.30-7.37 (2 H, m), 7.22-7.30 (3 H, m), 7.12 (1 H, d, J=15.4 Hz), 5.84 (1 H, s), 4.25-4.35 (1 H, m), 3.92 (3 H, s), 3.81-3.88 (1 H, m), 3.23-3.30 (1 H, m), 2.90-3.00 (1 H, m), 2.17 (3 H, s) ppm. MS (ESI) m/z: 595.9 (M+H)$^+$. Analytical HPLC: RT=7.31 min.

Example 47

(S,E)-N-(3-acetamido-1H-indazol-5-yl)-2-(3-(5-chloro-2-(1H-tetrazol-1-yl)phenyl)acryloyl)-1,2,3,4-tetrahydroisoquinoline-1-carboxamide

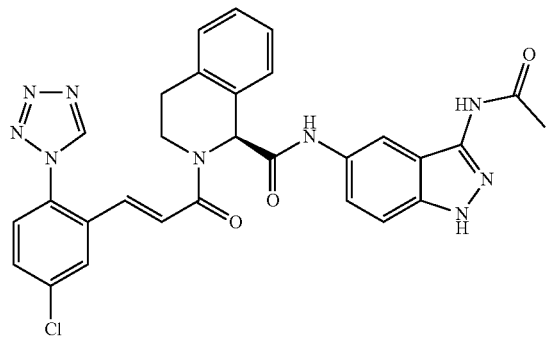 [SMILES: CC(=O)Nc1n[nH]c2ccc(NC(=O)[C@@H]3c4ccccc4CCN3C(=O)/C=C/c3cc(Cl)ccc3-n3cnnn3)cc12]

47A: tert-Butyl 3-amino-5-nitro-1H-indazole-1-carboxylate: To 2-fluoro-5-nitrobenzonitrile (1 g, 6.02 mmol) in EtOH (10 mL) was added hydrazine (1.512 mL, 48.2 mmol). The reaction exothermed and solidified. Diluted with EtOH (40 mL) and heated to reflux for 4 h. MS (ESI) m/z: 179 (M+H)$^+$. The reaction was concentrated and the crude product was dissolved in THF (20 mL) added di-tert-butyldicarbonate (1.398 mL, 6.02 mmol), DIEA (1.051 mL, 6.02 mmol), and a few crystals of DMAP. After 24 h, the reaction was concentrated and partitioned with aqueous saturated NH$_4$Cl (15 mL) and EtOAc (50 mL). The organic layer was washed with brine (10 mL) and dried (MgSO$_4$). Purified by normal phase chromatography and reverse phase HPLC and collected 47A as 0.266 g of a bright yellow solid. MS (ESI) m/z: 279 (M+H)+

Example 47 was made in a similar manner as Example 46 using 47A. $^1$H NMR (400 MHz, MeOD) δ:10.20 (1 H, br. s), 9.52 (1 H, s), 8.19 (1 H, d, J=2.3 Hz), 7.91 (1 H, br. s), 7.66 (1 H, dd, J=8.6, 2.3 Hz), 7.53-7.62 (2 H, m), 7.32-7.47 (3 H, m), 7.27 (2 H, d, J=3.3 Hz), 7.13-7.25 (1 H, d, J=15.4 Hz), 5.86 (1 H, s), 4.25-4.35 (1 H, m), 3.88 (1 H, td, J=8.3, 4.2 Hz), 2.90-3.02 (1 H, m), 2.70-2.81 (1 H, m), 2.19 (3H, br. s) ppm. MS (ESI) m/z: 581.9 (M+H)$^+$. Analytical HPLC: RT=6.89 min.

Example 48

(S)-4-(2-(3-(5-Chloro-2-(1H-tetrazol-1-yl)phenyl)propioloyl)-1,2,3,4-tetrahydroisoquinoline-1-carboxamido)benzoic acid

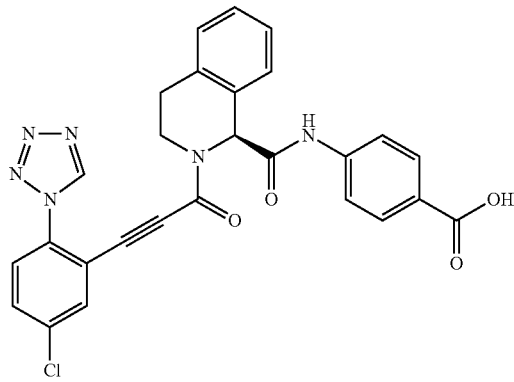 [SMILES: O=C(O)c1ccc(NC(=O)[C@@H]2c3ccccc3CCN2C(=O)C#Cc2cc(Cl)ccc2-n2cnnn2)cc1]

48A: Methyl 3-(tributylstannyl)propiolate: Combined methyl propiolate (5.89 g, 70.1 mmol) and tributyl(methoxy)stannane (13.45 mL, 46.7 mmol) in toluene and heated to 100° C. for 72 h. Cooled, concentrated and used as is in next step.

48B: Methyl 3-(5-chloro-2-(1H-tetrazol-1-yl)phenyl)propiolate: To crude 48A (8 g, 21.44 mmol) was added toluene (40 mL) and the solution was degassed with nitrogen. Added 1-(4-chloro-2-iodophenyl)-1H-tetrazole (6 g, 19.58 mmol), tetrakis(triphenylphospine)palladium (0) (0.113 g, 0.098 mmol) and the reaction was heated to 90° C. for 24 h. The reaction was filtered through paper and the filtrate partitioned with H$_2$O (30 mL) and EtOAc (100 mL). The organic layer was washed with 10% aqueous KF (25 mL) and insoluble solid filtered off. Aqueous layer was re-extracted with EtOAc (50 mL). Combined organic layers were washed with brine (50 mL) and dried (MgSO$_4$). Purification by normal phase chromatography afforded 3.9 g (76%) of 48B as a tan solid. MS (ESI) m/z: 263.2 (M+H)+

48C: 3-(5-Chloro-2-(1H-tetrazol-1-yl)phenyl)propiolic acid: To 48B (1 g, 3.81 mmol) in THF (15 mL) and H$_2$O (10 mL), cooled in ice bath, was added LiOH (0.274 g, 11.42 mmol). After 1 h at 0° C., the reaction was acidified with 1N HCl, solvents reduced and tan solid filtered off. Suspended solid in EtOAc and filtered to afford 0.8 g of 48C. MS (ESI) m/z: 249.1 (M+H)+.

48D: (S)-tert-Butyl 4-(2-(3-(5-chloro-2-(1H-tetrazol-1-yl)phenyl)propioloyl)-1,2,3,4-tetrahydroisoquinoline-1-carboxamido)benzoate: Combined 48C (0.055 g, 0.221 mmol), 3B (0.078 g, 0.221 mmol), BOP (0.098 g, 0.221 mmol), and DIEA (0.039 mL, 0.221 mmol) in DMF (1 mL). After 24 h, the reaction was partitioned with H$_2$O (10 mL) and brine (10 mL) and EtOAc (60 mL). The organic layer was washed with brine (10 mL) and dried (MgSO$_4$). MS (ESI) m/z: 582.9 (M+H)+.

Example 48: 48D was deprotected with 30% TFA in DCM (20 mL) for 1.5 h, concentrated and purified by reverse phase HPLC to afford 48 mg (39.1%) of desired product as pale yellow solid. $^1$H NMR (400 MHz, MeOD) δ 9.76 (1 H, s), 7.92-8.05 (3 H, m), 7.74-7.86 (2 H, m), 7.61-7.72 (2 H, m), 7.46-7.54 (1 H, m), 7.16-7.38 (3 H, m), 5.78 (1 H, s), 4.13 (1 H, ddd, J=12.1, 7.1, 4.5 Hz), 3.69 (1 H, ddd, J=12.6, 8.1, 4.3 Hz), 3.22 (1 H, ddd, J=15.7, 8.1, 4.3 Hz), 2.84-2.96 (1H, m) ppm. MS (ESI) m/z: 526.9 (M+H)$^+$. Analytical HPLC: RT=8.08 min.

Example 49

(S,E)-N-(3-amino-1-methyl-1H-indazol-5-yl)-2-(3-(5-chloro-2-(1H-tetrazol-1-yl)phenyl)acryloyl)-1,2,3,4-tetrahydroisoquinoline-1-carboxamide, TFA salt

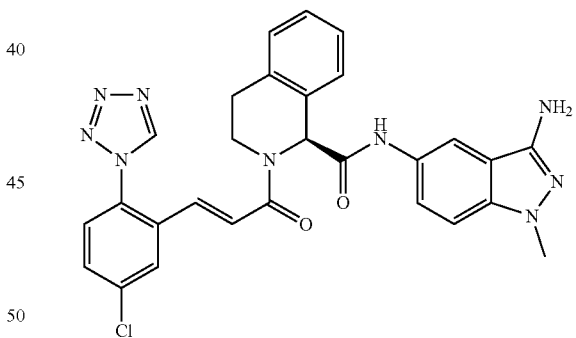

49A: 1-Methyl-1H-indazole-3,5-diamine: To 46A (0.28 g, 1.457 mmol) in acetone (20 mL) H$_2$O (15 mL) was added zinc (0.476 g, 7.29 mmol), cooled to 0° C., and added ammonium chloride (0.779 g, 14.57 mmol). After 24 h, filtered solids off and concentrated filtrate to afford crude product as a gummy dark solid. MS (ESI) m/z: 163 (M+H)$^+$.

Example 49 was made in a similar manner as Example 20 using 49A. $^1$H NMR (400 MHz, MeOD) δ 9.52 (1 H, s), 8.19 (1 H, d, J=2.3 Hz), 8.01 (1 H, d, J=1.3 Hz), 7.66 (1 H, dd, J=8.3, 2.3 Hz), 7.52-7.60 (2 H, m), 7.43-7.49 (1 H, m), 7.34-7.40 (2 H, m), 7.28 (3 H, d, J=2.5 Hz), 7.15-7.24 (1 H, d, J=15.4 Hz), 5.84 (1 H, s), 4.25-4.39 (1 H, m), 3.86-3.92 (1 H, m), 3.82 (3 H, s), 3.26-3.28 (1 H, m), 2.94-3.04 (1 H, m) ppm. MS (ESI) m/z: 554 (M+H)$^+$. Analytical HPLC: RT=6.83 min.

Example 50

(E)-4-(2-(3-(5-Chloro-2-(1H-tetrazol-1-yl)phenyl)acryloyl)-3,3-dimethyl-1,2,3,4-tetrahydroisoquinoline-1-carboxamido)benzoic acid

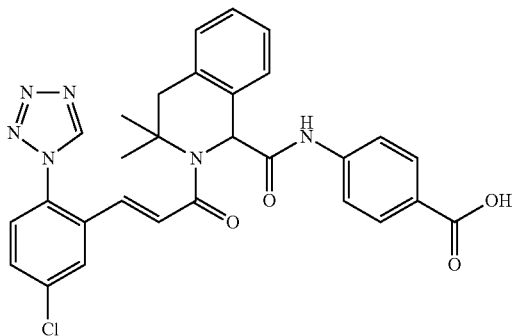 [SMILES: CC1(C)Cc2ccccc2C(C(=O)Nc2ccc(C(=O)O)cc2)N1C(=O)/C=C/c1cc(Cl)ccc1-n1cnnn1]

Example 50 was prepared by the Ugi reaction as in Example 20 starting from commercially available 3,3-dimethyl-1,2,3,4-tetrahydroisoquinoline and Intermediate 6 followed by TFA deprotection. $^1$H NMR (400 MHz, DMSO-d$_6$) δ 10.43 (1 H, s), 9.76 (1 H, s), 8.09 (1 H, br. s), 7.81 (2H, d, J=8.6 Hz), 7.53-7.73 (5 H, m), 7.20-7.28 (2 H, m), 7.14-7.19 (1 H, m), 7.10 (1 H, d, J=15.4 Hz), 6.83 (1 H, d, J=15.2 Hz), 5.80 (1 H, br. s), 3.47 (1 H, d, J=14.6 Hz.), 2.47-2.64 (2 H, q, J=14.9 Hz), 1.71 (3 H, s), 1.13 (3H, br. s) ppm. MS (ESI) m/z: 556.8 (M+H)$^+$. Analytical HPLC: RT=8.49 min.

Example 51

(E)-4-(2-(3-(5-Chloro-2-(1H-tetrazol-1-yl)phenyl)acryloyl)-4,4-dimethyl-1,2,3,4-tetrahydroisoquinoline-1-carboxamido)benzoic acid

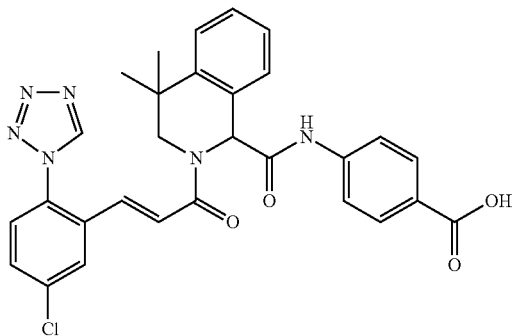 [SMILES: CC1(C)CN(C(=O)/C=C/c2cc(Cl)ccc2-n2cnnn2)C(C(=O)Nc2ccc(C(=O)O)cc2)c2ccccc21]

51A: 2-Methyl-2-phenylpropanenitrile: To a cold mixture of phenylacetonitrile (5 g, 0.047 moles) and methyl iodide (9.34 mL, 0.149 moles) in THF (30 mL) was added drop wise at 0° C. a cold slurry of NaH (60% in mineral oil, 2.05 g, 0.085 moles) in 20 mL of THF over a period of 30 min. The reaction was stirred for 30 min at 0° C. and gradually brought to rt and then stirring was continued for 4 h. The reaction mixture cooled to 0° C. then poured on 100 g of crushed ice, the aqueous layer was extracted with MTBE (2×100 mL). The combined organics were washed with H$_2$O, brine, dried over Na$_2$SO$_4$, filtered and concentrated to give 5 g of 51A as brown oil. The material was carried on to the next step without further purification. $^1$H NMR (400 MHz, CDCl$_3$) δ 7.48 (2 H, d, J=4.36 Hz), 7.39 (2 H, q, J=5.0 Hz), 7.31 (1 H, t, J=3.63 Hz), 1.73 (6 H, s) ppm.

51B: 2-Methyl-2-phenylpropan-1-amine: To 0° C. cooled slurry of lithium aluminium hydride (2.61 g, 0.068 moles) in 26 mL of THF was added 51A (5 g, 0.034 moles) in 60 mL of THF dropwise. Gradually, the reaction temperature was brought to rt and stirred for 3 h. After cooling the reaction to 0° C., 10 mL of saturated aqueous solution of sodium sulphate was added and then filtered on Celite® and washed with EtOAc. The filtrate washed with H$_2$O, brine, dried over Na$_2$SO$_4$, filtered and concentrated to give 4 g of 51B as a white solid. The material was carried onto the next step without further purification. MS (ESI) m/z: 149.2 (M+H)$^+$.

51C: 4, 4-Dimethyl-3, 4-dihydroisoquinoline: A mixture of 51B (500 mg, 3.35 mmol) and 5 mL of 98% formic acid was slowly heated to 180° C. and kept at this temperature for 1 h and during this time excess formic acid was allowed to distill. Then, 3.5 g of polyphosphoric acid and 750 mg of P2O5 were added. The reaction was heated to 180° C. for 2 h. The reaction was diluted with cold H$_2$O and extracted with DCM. The aqueous layer was basified with 40% NaOH solution and extracted with DCM. The combined organic layer was washed with H$_2$O, brine, dried over Na$_2$SO$_4$, filtered and concentrated to give 250 mg of 51C as a white solid. LCMS m/z: 160.2 (M+H)$^+$. MS (ESI) m/z: 160.2 (M+H)$^+$.

Example 51 was prepared by the Ugi reaction as in Example 50 starting from 51C and Intermediates 2 and 6 followed by TFA deprotection to afford 10 mg of desired product as white solid. $^1$H NMR (400 MHz, DMSO-d$_6$) δ 10.97 (1 H, s), 9.89 (1 H, s), 8.46 (1 H, d, J=2.0 Hz), 7.90 (2 H, d, J=8.68 Hz), 7.75 (4 H, m, J=6.8 Hz), 7.58 (1 H, d, J=15.2 Hz), 7.50 (1 H, t, J=9.24 Hz), 7.29 (1 H, t, J=7.34 Hz), 7.23 (1 H, t, J=7.48 Hz), 7.04 (1 H, d, J=15 Hz), 5.94 (1 H, s), 4.17 (1 H, d, J=13.8 Hz), 3.96 (1 H, d, J=13.0 Hz), 1.47 (3 H, s), 1.21 (1 H, s) ppm. MS (ESI) m/z: 556.9 (M+H)$^+$. Analytical HPLC: RT=17.41 min.

Example 52

(E)-4-(7-Bromo-2-(3-(5-chloro-2-(1H-tetrazol-1-yl)phenyl)acryloyl)-4,4-dimethyl-1,2,3,4-tetrahydroisoquinoline-1-carboxamido)benzoic acid

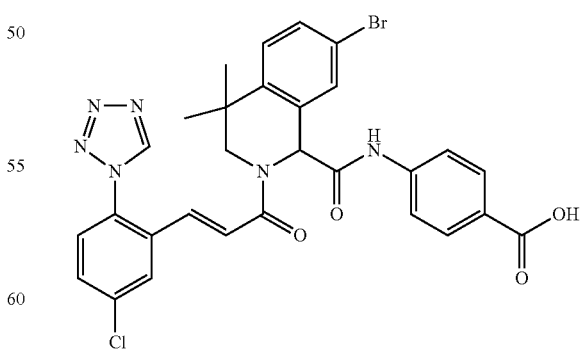

52A: 2-(4-Bromophenyl)-2-methylpropanenitrile: Methyl iodide was added to a solution of 2-(4-bromophenyl)acetonitrile (1.5 g, 2.5 m mol) in dry THF (20 mL) at 0° C., stirred for 10 min and then added to a solution of NaH (1.2 g, 5.1 mmol) in dry THF (80 mL) at 0° C. The reaction mixture was slowly brought to rt and stirred for 4 h. The reaction mixture was poured into crushed ice and extracted with EtOAc (2×), the combined organics were washed with H₂O, brine, dried over Na₂SO₄, concentrated to give 5 g of 52A as a brown liquid. ¹H NMR (400 MHz, CDCl₃) δ 7.53 (2 H, d, J=1.2 Hz), 7.36 (2 H, d, J=1.2 Hz), 1.72 (6 H, s) ppm.

52B: 2-(4-Bromophenyl)-2-methylpropan-1-amine: To a solution of 52A (1 g, 4.4 mmol) in toluene (45 mL), Red-Al (7.2 g, 3.5 mmol) in toluene (5 mL) was added at 0° C. drop-wise and stirred for 1 h. The reaction mixture was poured into ice and filtered through Celite®. The filtrate was extracted with DCM, the combined organics were washed with H₂O, brine, dried over Na₂SO₄, filtered and concentrated to give 0.75 g of 52B as a pink liquid. MS (ESI) m/z: 230 (M+H)⁺.

52C: N-(2-(4-Bromophenyl)-2-methylpropyl)formamide: 52B (0.5 g, 2.1 mmol) in 98% formic acid (5 mL) was slowly heated to 180° C. for 1 h and during this time excess formic acid was allowed to distill to afford 0.2 g of colorless liquid. The crude 52C was taken to next step directly without further purification. ¹H NMR (400 MHz, CDCl₃) δ 8.11 (1 H, s), 7.86 (2 H, d, J=6.8 Hz), 7.26 (2 H, d, J=4.8 Hz), 5.14 (1H, s), 3.53 (2H, d, J=6.0 Hz), 1.35 (6 H, s). MS (ESI) m/z: 256 (M+H)⁺.

52D: 7-Bromo-4,4-dimethyl-3,4-dihydroisoquinoline: To 52C (0.1 g, 0.7 mmol) was added P₂O₅ and the reaction was refluxed for 2 h at 180° C. The reaction mixture was quenched with ice cold H₂O, made basic with NaHCO₃, extracted with EtOAc twice. The combined organic layers were washed with H₂O, brine, dried over Na₂SO₄, filtered and concentrated to give 70 mg of 52D as brown liquid. MS (ESI) m/z: 240 (M+H)⁺.

Example 52 was prepared by the Ugi reaction as in Example 50 starting from 52D and Intermediates 2 and 6 followed by TFA deprotection to afford 10 mg of desired product as a white solid. ¹H NMR (400 MHz, CDCl₃) δ 10.89 (1 H, s), 9.88 (1 H, s), 8.45 (1 H, d, J=2.0 Hz), 7.92 (2 H, d, J=8.8 Hz), 7.80 (4 H, m), 7.66 (1 H, s), 7.59 (1 H, d, J=15.2 Hz), 7.48 (2 H, s), 7.08 (1 H, d, J=15.2 Hz), 5.95 (1 H, s), 4.20 (1H, d, J=13.6 Hz), 3.94 (1 H, d, J=13.6 Hz), 1.45 (3 H, s), 1.20 (3H, s) ppm. MS (ESI) m/z: 636 (M+H)⁺. Analytical HPLC: RT=11.13 min.

Example 53

(R,E)-Methyl 4-(2-(3-(5-chloro-2-(1H-tetrazol-1-yl) phenyl)acryloyl)-1,2,3,4-tetrahydroisoquinoline-1-carboxamido)benzoylcarbamate

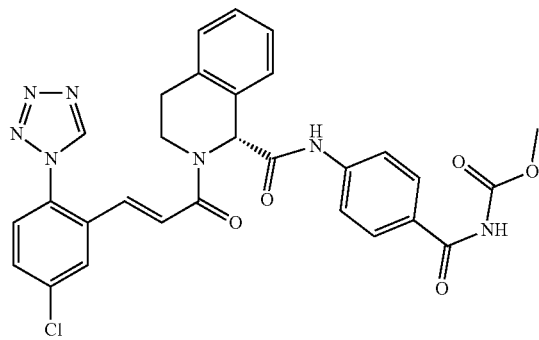 [SMILES: COC(=O)NC(=O)c1ccc(NC(=O)[C@H]2c3ccccc3CCN2C(=O)/C=C/c2cc(Cl)ccc2-n2cnnn2)cc1]

53A: Methyl 4-nitrobenzoylcarbamate: (Following the procedure of Sestanj, K, et. al., U.S. Pat. No. 4,843,062). Dissolved 4-nitrobenzoyl chloride (2.5 g, 13.4 mmol) in CCl₄ (100 mL) and added to a suspension of silver cyanate (2.0 g, 13.4 mmol) in CCl₄ (100 mL) and the reaction was heated to reflux for 18 h. The reaction was concentrated and then heated to 90° C. in toluene (50 mL) and MeOH (20 mL) for 6 h. The reaction mixture was filtered, concentrated and purified by normal phase chromatography to afford 0.29 g (9.6%) of desired product as a white solid. MS (ESI) m/z: 224.9 (M+H)⁺.

53B: Methyl 4-aminobenzoylcarbamate: 53A was hydrogenated at 55 psi in EtOH (25 mL) in presence of 10% Pd/C (30 mg). Filtration and concentration afforded 0.25 g (9.6%) a white solid as the desired product. MS (ESI) m/z: 195.0 (M+H)⁺.

53C: (R)-Methyl 4-(1,2,3,4-tetrahydroisoquinoline-1-carboxamido)benzoyl carbamate: To (R)-2-(((9H-fluoren-9-yl) methoxy)carbonyl)-1,2,3,4-tetrahydroisoquinoline-1-carboxylic acid (144 mg, 0.360 mmol) and 53B (70 mg, 0.360 mmol) in DMF (2 mL) was added BOP (0.159 g, 0.360 mmol) and DIEA (94 µL, 0.541 mmol). After 24 h, the reaction was quenched with 1N HCl (10 mL) and extracted with EtOAc (3×20 mL). The combined organic layers were washed with brine (10 mL) and dried (MgSO₄). MS (ESI) m/z: 575.9 (M+H)⁺. Crude product was deprotected with 1.5 mL of 20% piperidine in DMF. After 40 min, the reaction was acidified, diluted with MeOH, filtered, and purified by reverse phase HPLC to afford 49 mg (38%) of 53C. MS (ESI) m/z: 353.9 (M+H)⁺.

Example 53 was prepared from 53C and Intermediate 1 in a manner similar to Example 1. ¹H NMR (400 MHz, MeOD) δ 9.51-9.59 (1 H, m), 8.20 (1 H, d, J=2.0 Hz), 7.85 (2 H, d, J=8.8 Hz), 7.65-7.75 (3 H, m), 7.49-7.62 (2 H, m), 7.30-7.41 (1 H, d, J=15.4 Hz)), 7.27-7.32 (3 H, m), 7.21 (1 H, d, J=15.4 Hz), 5.84 (1 H, s), 4.27-4.38 (1 H, m), 3.84-3.92 (1 H, m), 3.82 (3 H, s), 3.36 (1 H, m), 2.98 (1 H, ddd, J=16.2, 5.2, 5.1 Hz) ppm. MS (ESI) m/z: 585.9 (M+H)⁺. Analytical HPLC: RT=8.38 min.

Example 54

(E)-2-(3-(5-Chloro-2-(1H-tetrazol-1-yl)phenyl)acryloyl)-N-(4-hydroxy-2-oxo-1,2-dihydroquinolin-6-yl)-1,2,3,4-tetrahydroisoquinoline-1-carboxamide

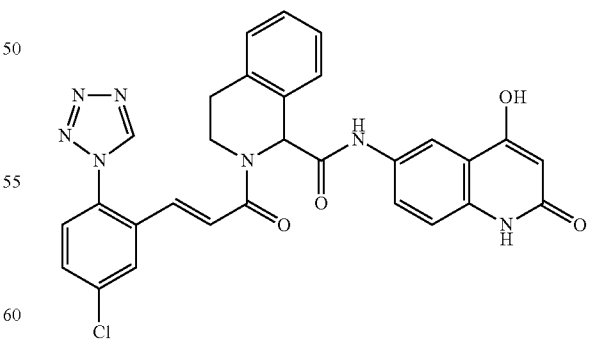

54A: tert-Butyl 3-(4-(tert-butoxycarbonylamino)phenylamino)-3-oxopropanoate: To tert-butyl 4-aminophenylcarbamate (2.60 g, 12.49 mmol) and 3-tert-butoxy-3-oxopropanoic acid (2 g, 12.49 mmol) in EtOAc (100 mL), cooled to 0° C., was added TEA (5.22 mL, 37.5 mmol) and a 50% solution of T3P in DMF (6.00 mL, 21.23 mmol). After 24 h, the reaction was partitioned with dilute HCl (15 mL) and EtOAc (75 mL). The organic layer was washed with brine (15 mL) and dried (MgSO₄). Purified by silica gel chromatography to afford 3.3 g (75%). MS (ESI) m/z: 351 (M+H)⁺.

54B: 6-Amino-4-hydroxyquinolin-2(1H)-one: To 54A (1 g, 2.85 mmol) was added PPA (6 mL, 2.85 mmol) and the mixture was heated to 140° C. for 4 h. After 48 h at rt, the reaction was quenched with ice H₂O and filtered to afford 0.68 g of a tan solid. MS (ESI) m/z: 177 (M+H)⁺.

Example 54 was prepared from 54B in a similar manner as Example 53, and the product was determined to be racemic. ¹H NMR (400 MHz, MeOD) δ 9.54 (1 H, s), 8.20 (2 H, s), 7.76 (1 H, dd, J=8.8, 1.8 Hz), 7.67 (1 H, dd, J=8.6, 2.3 Hz), 7.52-7.61 (2 H, m), 7.25-7.41 (6 H, m), 7.17-7.26 (1 H, d, J=15.7 Hz), 6.01 (1 H, s), 5.86 (1 H, s), 4.30-4.39 (1 H, m), 3.88 (1 H, ddd, J=12.4, 8.7, 4.2 Hz), 3.13-3.21 (1 H, m), 2.96-3.04 (1 H, m) ppm. MS (ESI) m/z: 567.9 (M+H)⁺. Analytical HPLC: RT=7.30 min.

Examples 55 and 56

(E)-4-(8-bromo-2-(3-(5-chloro-2-(1H-tetrazol-1-yl)phenyl)acryloyl)-4,4-dimethyl-1,2,3,4-tetrahydroisoquinoline-1-carboxamido)benzoic acid and (E)-4-(6-bromo-2-(3-(5-chloro-2-(1H-tetrazol-1-yl)phenyl)acryloyl)-4,4-dimethyl-1,2,3,4-tetrahydroisoquinoline-1-carboxamido)benzoic acid

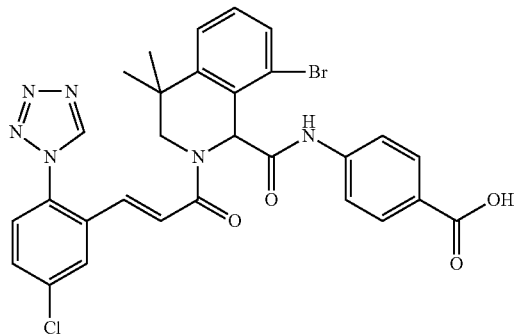

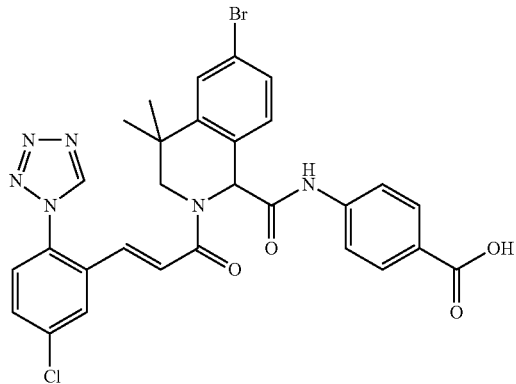

55A: 8-Bromo-4,4-dimethyl-3,4-dihydroisoquinoline and 56A: 6-bromo-4,4-dimethyl-3,4-dihydroisoquinoline: 55A and 56A were synthesized as in Example 52. N-(2-(3-bromophenyl)-2-methylpropyl)formamide (0.22 g, 0.8 mmol) was heated to reflux in P₂O₅(7 mL) for 2 h at 180° C. The crude reaction was purified by column chromatography using basic alumina to provide 40 mg of each regioisomer 55A and 56A. MS (ESI) m/z: 240 (M+H)⁺.

Examples 55 and 56 were prepared by the Ugi reaction as in Example 52 starting from a mixture of 55A and 56A and Intermediates 2 and 6 followed by separation of regioisomers and by TFA deprotection to afford 0.010 g of Example 55 as a white solid. ¹H NMR (400 MHz, DMSO-d₆) δ 12.76 (1 H, s), 10.4 (1 H, s), 9.88 (1 H, s), 8.46 (1 H, d, J=2.0 Hz), 7.88 (2 H, d, J=8.8 Hz), 7.37-7.80 (3 H, m), 7.49-7.62 (3 H, m), 7.28 (1 H, t, J=8.0 Hz), 6.95-7.21 (2 H, m), 6.40-6.50 (1 H, s), 4.39 (1 H, d, J=14.4 Hz), 3.53 (1 H, d, J=14 Hz), 1.40 (3 H, s), 1.15 (3 H, s) ppm. MS (ESI) m/z: 635 (M+H)⁺. Analytical HPLC: RT=10.97 min.

Example 56 was synthesized as in Example 55 to afford 10 mg of a white solid. ¹H NMR (400 MHz, DMSO-d₆) δ 10.93 (1 H, s), 9.87 (1 H, s), 8.44 (1 H, d, J=12 Hz), 7.67-7.79 (5 H, m), 7.57 (1 H, d, J=15.6 Hz), 7.41-7.47 (2 H, m), 7.05 (1 H, d, J=15.2 Hz), 5.91-6.54 (1 H, s) 4.17 (1H, d, J=14.0 Hz), 3.93 (1 H, d, J=14.0 Hz), 1.46 (3 H, s), 1.21 (3 H, s) ppm. MS (ESI) m/z: 635 (M+H)⁺. Analytical HPLC: RT=19.42 min.

Example 57

(E)-methyl 4-(5-(3-(5-chloro-2-(1H-tetrazol-1-yl)phenyl)acryloyl)-4,5,6,7-tetrahydro-3H-imidazo[4,5-c]pyridine-4-carboxamido)phenylcarbamate, TFA salt

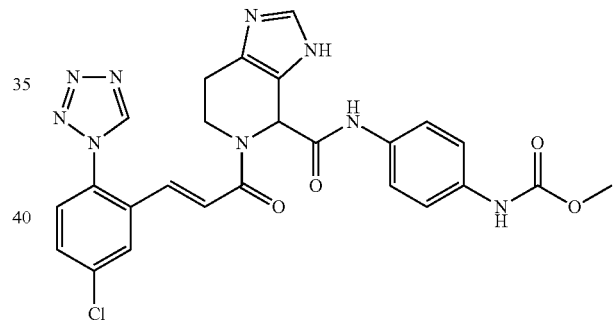

57A: (E)-5-(3-(5-chloro-2-(1H-tetrazol-1-yl)phenyl)acryloyl)-4,5,6,7-tetrahydro-3H-imidazo[4,5-c]pyridine-4-carboxylic acid: To commercially available 4,5,6,7-tetrahydro-3H-imidazo[4,5-c]pyridine-4-carboxylic acid, 2 HCl (0.2 g, 0.833 mmol) and Intermediate 1 (0.15 g, 0.431 mmol) in DMF (1.2 mL) was added DIEA (0.873 mL, 5.00 mmol). After 24 h, the crude reaction mixture was taken onto the next step. MS (ESI) m/z: 400.2 (M+H)⁺.

Example 57: To 57A (0.15 g, 0.375 mmol) and methyl 4-aminophenyl carbamate, HCl (0.076 g, 0.375 mmol) in EtOAc (5 mL) and CHCl₃ (1 mL) cooled in ice bath, was added, DIEA (0.262 mL, 1.501 mmol) and 50% solution of T3P in EtOAc (0.159 mL, 0.563 mmol). After 24 h, the reaction was concentrated, purified by reverse phase HPLC and freeze-dried to afford 35 mg (14%) of Example 57 as a tan solid. ¹H NMR (400 MHz, MeOD) δ □9.45 (1 H, s), 8.75 (1 H, s), 8.13 (1 H, d, J=1.52 Hz), 7.59 (1 H, dd, J=8.59, 2.02 Hz), 7.48-7.54 (1 H, m), 7.34-7.40 (2 H, m), 7.24-7.32 (3 H, m), 7.11-7.24 (1 H, m), 6.19 (1 H, s), 4.50-4.61 (1 H, m), 3.63 (3H, s), 3.54-3.65 (1 H, m), 2.73-2.99 (2 H, m) ppm. MS (ESI) m/z: 548.3 (M+H)⁺. Analytical HPLC: RT=5.62 min.

Example 58

(E)-4-(2-(3-(5-Chloro-2-(1H-tetrazol-1-yl)phenyl)acryloyl)-2,3,4,5-tetrahydro-1H-pyrido[4,3-b]indole-1-carboxamido)benzoic acid

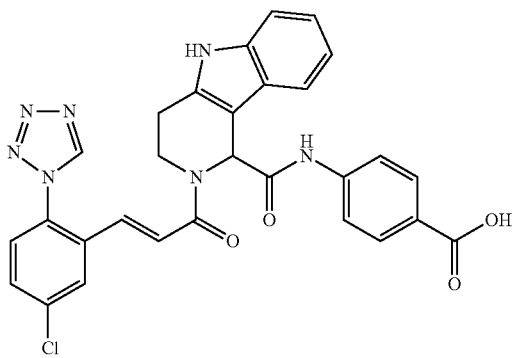 [SMILES: O=C(O)c1ccc(NC(=O)C2c3c([nH]c4ccccc34)CCN2C(=O)/C=C/c2cc(Cl)ccc2-n2cnnn2)cc1]

58A: 2-Benzyl 1-methyl 3,4-dihydro-1H-pyrido[4,3-b]indole-1,2(5H)-dicarboxylate: To commercially available 2,3,4,5-tetrahydro-1H-pyrido[4,3-b]indole-1-carboxylic acid (0.5 g, 2.312 mmol) in MeOH (30 mL) was added thionyl chloride (0.338 mL, 4.62 mmol). After 24 h, additional thionyl chloride was added. The reaction was concentrated and then, partitioned between DCM (25 mL) and saturated NaHCO₃ (20 mL). To the above mixture was then added benzyl chloroformate (0.429 mL, 3.01 mmol). After 1.5 h, the reaction was partitioned with H₂O (15 mL) and DCM (60 mL). The organic layer was washed with brine (15 mL) and dried (MgSO₄). Purification by silica gel chromatography afforded a 0.8 g mixture of two compounds that were carried onto the next step. MS (ESI) m/z: 365.0 (M+H)⁺.

58B: Benzyl 1-(4-(tert-butoxycarbonyl)phenylcarbamoyl)-3,4-dihydro-1H-pyrido[4,3-b]indole-2(5H)-carboxylate: To a mixture of 58A (0.4 g, 1.098 mmol) and 5-benzyl 1-methyl 3,4-dihydro-1H-pyrido[4,3-b]indole-1,5(2H)-dicarboxylate (0.400 g, 1.098 mmol) was added 1:1 THF and H₂O (30 mL), cooled in ice bath, and added LiOH (0.138 g, 3.29 mmol). After 24 h, the reaction was carefully acidified and concentrated, then combined in EtOAc (30 mL) with tert-butyl 4-aminobenzoate (0.424 g, 2.195 mmol), DIEA (1.150 mL, 6.59 mmol) and a 50% solution of T3P in EtOAc (0.931 mL, 3.29 mmol). After 24 h, the reaction was quenched with H₂O (20 mL) and extracted with EtOAc (3×50 mL). The combined organic layers were washed with brine (20 mL) and dried (MgSO₄). Purification by silica gel chromatography afforded 0.23 g (40%) of a mixture of solids MS (ESI) m/z: 526.1 (M+H)⁺.

58C: tert-Butyl 4-(2,3,4,5-tetrahydro-1H-pyrido[4,3-b]indole-1-carboxamido)benzoate: 58B (0.115 g, 0.219 mmol) and Pd/C (15 mg) in EtOH (20 mL) were hydrogenated at 50 psi for 2 h. The reaction was filtered and purified by reverse phase HPLC to afford 70 mg (1.6%) of 58C as a white solid. MS (ESI) m/z: 392.0 (M+H)⁺.

Example 58: To Intermediate 1 (0.018 g, 0.052 mmol) and 58C (0.032 g, 0.052 mmol) was added DMF (0.7 mL) and DIEA (0.036 mL, 0.207 mmol). After 24 h, the reaction was purified by reverse phase HPLC and then deprotected with 30% TFA/DCM. Re-purification by reverse phase HPLC afforded 4.5 mg (15%) of Example 58 as a tan solid. ¹H NMR (400 MHz, MeOD)☐ δ 9.53 (1 H, s), 8.24 (1 H, d, J=2.27 Hz), 7.98 (2H, d, J=8.59 Hz), 7.72 (2H, dd, J=8.84, 1.52 Hz), 7.64-7.71 (1 H, m), 7.56-7.60 (1 H, m), 7.45-7.52 (2 H, m), 7.35 (1 H, d, J=8.08 Hz), 7.22 (1 H, d, J=15.41 Hz), 7.09-7.15 (1 H, m), 7.03 (1 H, t, J=7.45 Hz), 6.13 (1 H, s), 4.55 (1H, dt, J=13.64, 3.41 Hz), 3.86-4.04 (1 H, m), 2.91-3.02 (2 H, m) ppm. MS (ESI) m/z: 568.0 (M+H)⁺. Analytical HPLC: RT=8.48 min.

Example 59

(E)-4-(5-(3-(5-Chloro-2-(1H-tetrazol-1-yl)phenyl)acryloyl)-1,3-dimethyl-4,5,6,7-tetrahydro-1H-pyrazolo[4,3-c]pyridine-4-carboxamido)benzoic acid

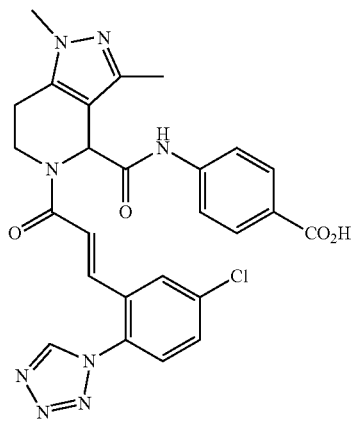 [SMILES: Cc1nn(C)c2c1C(C(=O)Nc1ccc(C(=O)O)cc1)N(C(=O)/C=C/c1cc(Cl)ccc1-n1cnnn1)CC2]

59A: Methyl 3-(benzyl amino) propanoate: Benzaldehyde (75 g, 0.707 mol), methyl 3-aminopropanoate (98.6 g, 0.707 mol) and 4A molecular sieves (150 g) were taken in DCM (1.2 L) and cooled to 0° C. To this cooled solution was then added TEA (295 mL). After 18 h at rt, the reaction mixture was filtered through Celite® and the filtrate was washed with 10% NaHCO₃, brine, dried over Na₂SO₄, filtered and concentrated to give the imine (110 g) as pale yellow liquid. To a solution of the imine in dry MeOH (1.2 L) was added NaBH₄ (15.3 g, 0.4 mol) at −40° C., the reaction mixture was slowly brought to −20° C. and stirred for 2 h. The reaction was quenched with saturated NaHCO₃ solution. MeOH was removed under vacuum and the product was extracted with EtOAc. The crude product was purified by acid-base workup to give 40 g of 59A as yellow solid. ¹H NMR (400 MHz, CDCl₃) δ 7.23-7.36 (5H, m), 3.81 (2H, s), 3.75 (3H, s), 2.88-2.93 (2H, t, J=8.4 Hz), 2.53-2.57 (2H, t, J=8.4 Hz) ppm.

59B: Methyl 3-(N-benzyl-3-oxobutanamido) propanoate: To a solution of 59A (20 g, 0.103 mmol) in xylenes (250 mL) was slowly added 2, 2, 6-trimethyl-4H-1, 3-dioxin-4-one (16.2 mL, 235.3 mmol) and the reaction was stirred at 130° C. for 2 h. The reaction was then concentrated and the crude material was cooled and washed with cold petroleum ether to give 24 g of 59B as brown oil. ¹H NMR (400 MHz, CDCl₃) δ 7.15-7.39 (5 H, m), 4.50 (2 H, s), 3.70 (3 H, s), 3.40-3.60 (2 H, m), 2.70 (2 H, s), 2.30-2.50 (2 H, m), 2.20 (3 H, s) ppm.

59C: 3-Acetyl-1-benzyl-4-hydroxy-5,6-dihydropyridin-2(1H)-one: To a solution of NaOMe (freshly prepared from Na (2.5 g, 0.108 mol) in MeOH (500 mL)) at 0° C., was added 59B (25 g, 0.09 mol) in dry MeOH (200 mL) and the reaction was heated at 50° C. for 2 h. The solvent was removed and quenched with 1N HCl solution, extracted with EtOAc twice, the combined organics were washed with H₂O, brine, dried over Na₂SO₄, filtered and concentrated. The crude was purified by silica gel chromatography to give 59C (18 g) as a pale brown liquid. MS (ESI) m/z: 246.2 (M+H)⁺.

59D: 5-Benzyl-1,3-dimethyl-6,7-dihydro-1H-pyrazolo[4,3-c]pyridin-4(5H)-one and 5-benzyl-2,3-dimethyl-6,7-dihydro-2H-pyrazolo[4,3-c]pyridin-4(5H)-one: To a solution of 59C (18 g, 0.073 mmol) in EtOH (400 mL) was added dry K$_2$CO$_3$ (20.1 g, 0.146 mol) and methyl hydrazine sulphate (12.7 g, 0.088 mol). The reaction was heated to reflux for 18 h. The solvent was removed and the residue was diluted with H$_2$O, extracted with EtOAc twice, the combined organics were washed with H$_2$O, brine, dried over Na$_2$SO$_4$, filtered and concentrated. The crude was purified by silica gel column chromatography to afford 12 g of 59D (mixture of isomers) as an off-white solid. MS (ESI) m/z: 256.2 (M+H)$^+$.

59E: 5-Benzyl-1,3-dimethyl-4,5,6,7-tetrahydro-1H-pyrazolo[4,3-c]pyridine and 5-benzyl-2,3-dimethyl-4,5,6,7-tetrahydro-2H-pyrazolo[4,3-c]pyridine: To a 0° C. solution of lithium aluminium hydride (8.9 g, 0.235 mol) in THF (200 mL) was drop-wise added a solution of 59D (12 g, 0.047 mol). The reaction mixture was stirred at 70° C. for 18 h. The reaction mixture was cooled to 0° C., quenched with H$_2$O, 15% NaOH solution, filtered and filtrate was concentrated to afford 10 g of 59E (mixture of isomers). MS (ESI) m/z: 242.4 (M+H)$^+$.

59F: 1,3-Dimethyl-4,5,6,7-tetrahydro-1H-pyrazolo[4,3-c]pyridine and 2,3-dimethyl-4,5,6,7-tetrahydro-2H-pyrazolo[4,3-c]pyridine: 59E (10 g) was hydrogenated in EtOH (200 mL) in the presence of Pd(OH)$_2$ (6 g) at 50° C. and 10 kg/cm$^2$ pressure for 18 h. The reaction mixture was cooled to rt, filtered through Celite® and washed twice with MeOH. The combined organics were evaporated to give 5.5 g of 59F (mixture of isomers). MS (ESI) m/z: 152.2 (M+H)$^+$.

59G: 1,3-Dimethyl-6,7-dihydro-1H-pyrazolo[4,3-c]pyridine and 2,3-dimethyl-6,7-dihydro-2H-pyrazolo[4,3-c]pyridine: 59F (5.5 g) was oxidized in a similar manner as Example 20B to give 3 g of 59G (mixture of isomers) as pale brown liquid. MS (ESI) m/z: 250.2 (M+H)$^+$.

Example 59 (20 mg), as the first of two isomers, was prepared from 59G (150 mg, 1.0 mmol) (mixture of isomers), Intermediate 2, and Intermediate 6, as described for Example 20, followed by HCl deprotection. $^1$H NMR (400 MHz, MeOD) δ 9.54 (1 H, s), 8.22-8.23 (1 H, d, J=2.4 Hz), 7.97-8.00 (2 H, d, J=8.8 Hz), 7.66-7.69 (3 H, m), 7.57-7.60 (1 H, d, J=8.4 Hz), 7.35-7.39 (1 H, d, J=15.8 Hz), 7.18-7.22 (1 H, d, J=15.2 Hz), 5.93 (1 H, s), 4.60 (1 H, s), 4.42-4.45 (1 H, d, J=12.8 Hz), 3.95-4.00 (1 H, m), 3.73 (3 H, s), 2.81-2.89 (2 H, m), 2.19 (3 H, s) ppm. MS (ESI) m/z: 547.2 (M+H)$^+$. Analytical HPLC: RT=9.61 min.

Example 60

(E)-5-(3-(3-Chloro-2-fluoro-6-(1H-tetrazol-1-yl)phenyl)acryloyl)-1,3-dimethyl-N-(2-oxo-1,2,3,4-tetrahydroquinolin-6-yl)-4,5,6,7-tetrahydro-1H-pyrazolo[4,3-c]pyridine-4-carboxamide

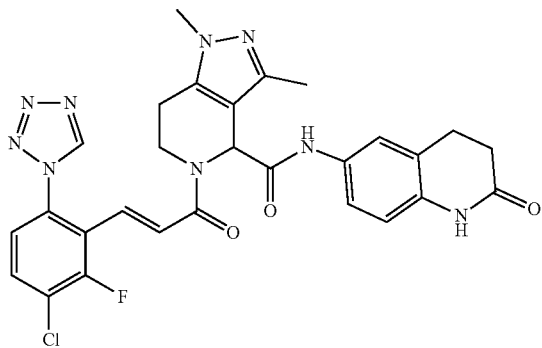 [SMILES: Cc1nn(C)c2c1C(C(=O)Nc1ccc3c(c1)CCC(=O)N3)N(C(=O)/C=C/c1c(-n3cnnn3)ccc(Cl)c1F)CC2]

60A and 60B: Benzyl 4-cyano-1, 3-dimethyl-6,7-dihydro-1H-pyrazolo[4,3-c]pyridine-5(4H)-carboxylate and Benzyl 4-cyano-2, 3-dimethyl-6,7-dihydro-2H-pyrazolo[4,3-c]pyridine-5(4H)-carboxylate: To a solution of 59G (mixture of isomers) (3.0 g, 0.0201 mol) and trimethylsilyl cyanide (2.19 g, 0.022 mol) in DCM (100 mL) cooled to 0° C. was added benzyl chloroformate (3.75 g, 0.022 mol) and anhydrous AlCl$_3$ (50 mg) and the reaction mixture was stirred at rt for 2 h. Reaction mixture was poured in to 10% NaHCO$_3$ solution (100 mL) and extracted with DCM (2×100 mL). Combined organic extracts were washed with H$_2$O, brine, dried over Na$_2$SO$_4$ and concentrated to give crude product. The crude was then purified by silica gel column chromatography to give 1.3 g of 60A and 0.5 g of 60B. MS (ESI) m/z: 311.2 (M+H)$^+$.

60C: 1, 3-dimethyl-4,5,6,7-tetrahydro-1H-pyrazolo[4,3-c]pyridine-4-carboxylic acid hydrochloride: 60A (1.3 g, 4.19 mol) was taken in concentrated HCl (60 mL) and stirred at 100° C. overnight. Reaction mixture was concentrated under reduced pressure to give 400 mg of 60C as hydrochloride salt. MS (ESI) m/z: 194.2 (M–H)–.

60D: 5-(tert-butoxycarbonyl)-1, 3-dimethyl-4,5,6,7-tetrahydro-1H-pyrazolo[4,3-c]pyridine-4-carboxylic acid: To 60C (0.9 g, 3.9 mmol) in H$_2$O (25 mL), was added NaHCO$_3$ (1.63 g, 19.4 mmol) and Boc$_2$O (2.55 g, 11.6 mmol). After 18 h, the reaction mixture was diluted with H$_2$O, washed with Et$_2$O. The aqueous layer was separated, acidified with 10% citric acid solution and extracted with EtOAc (2×100 mL). Combined organic extracts were washed with H$_2$O, brine, dried over Na$_2$SO$_4$, filtered and concentrated to give crude product, which was washed with hexane and dried under vacuum to give 950 mg of the 60D. $^1$H NMR (400 MHz, MeOD) δ 5.32 (1H, s), 4.92 (2H, s), 3.67 (3H, s), 2.62-2.72 (2H, m), 2.26 (3H, s), 1.50 (9H, s) ppm. MS (ESI) m/z: 296.4

60E: 1,3-Dimethyl-N-(2-oxo-1,2,3,4-tetrahydroquinolin-6-yl)-4,5,6,7-tetrahydro-1H-pyrazolo[4,3-c]pyridine-4-carboxamide: To a mixture of 60D (82 mg, 0.277 mmol) and 6-amino-3,4-dihydroquinolin-2(1H)-one (45 mg, 0.277 mmol) in EtOAc (2 mL)/DMF (0.5 mL) was added DIEA (194 μL, 1.110 mmol) and a 1M solution of T3P in EtOAc (555 μL, 0.555 mmol). The reaction was concentrated and treated with a 30% solution of TFA in DCM (4 mL). After 1 h, the reaction was concentrated and purified by reverse phase HPLC and freeze-dried to afford 99 mg of 60E. MS (ESI) m/z: 340 (M+H)$^+$.

Example 60: To 60E (0.099 g, 0.290 mmol) and Intermediate 3A (0.078 g, 0.290 mmol) in EtOAc (2 mL)/DMF (1 mL) was added DIEA (0.203 mL, 1.161 mmol) and a 1M solution of T3P in EtOAc (0.581 mL, 0.581 mmol). After 24 h, the reaction was concentrated and purified by reverse phase HPLC and freeze-dried to afford 11.5 mg (6.4%) of Example 60 as a white solid. $^1$H NMR (400 MHz, MeOD) □δ 9.56 (1 H, s), 7.81 (1 H, t, J=8.1 Hz), 7.48-7.55 (1 H, m), 7.40 (1 H, s), 7.31-7.37 (1H, m), 7.11-7.21 (1 H, m), 7.00-7.10 (1 H, m), 6.84 (1 H, d, J=8.3 Hz), 5.95 (1 H, s), 4.13-4.24 (1 H, m), 3.86-3.99 (1 H, m), 3.76 (3 H, s), 2.91-3.02 (2 H, m), 2.80 (1 H, d, J=10.6 Hz), 2.54-2.63 (2 H, m), 2.24 (3 H, s), 1.32-1.45 (1 H, m) ppm. MS (ESI) m/z: 590.0 (M+H)$^+$. Analytical HPLC: RT=5.86 min.

Example 61

(E)-4-(5-(3-(5-Chloro-2-(1H-tetrazol-1-yl)phenyl)acryloyl)-2-methyl-4,5,6,7-tetrahydro-1H-imidazo[4,5-c]pyridine-4-carboxamido)benzoic acid, TFA salt

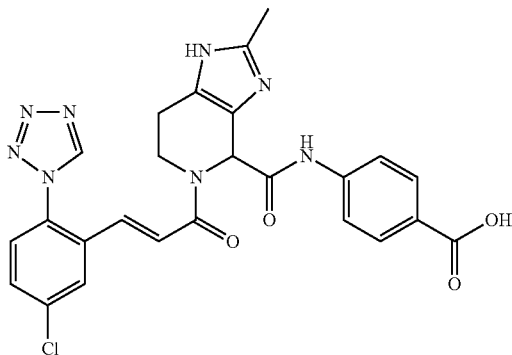 [SMILES: Cc1nc2c([nH]1)CCN(C(=O)/C=C/c1cc(Cl)ccc1-n1cnnn1)C2C(=O)Nc1ccc(C(=O)O)cc1]

Example 61 was made in a similar manner as Example 20 starting with commercially available 2-methyl-4,5,6,7-tetrahydro-1H-imidazo[4,5-c]pyridine. $^1$H NMR (400 MHz, MeOD) δ 9.44 (1 H, s), 8.12 (1 H, d, J=1.8 Hz), 7.89 (2 H, d, J=8.8 Hz), 7.56-7.70 (3 H, m), 7.50 (1 H, d, J=8.3 Hz), 7.22-7.30 (1 H, d, J=15.4 Hz), 7.14-7.22 (1 H, d, J=15.4 Hz), 6.13 (1 H, s), 4.51 (1 H, br. s), 3.61 (1 H, br. s), 2.83-2.90 (1 H, m), 2.69-2.78 (1 H, m), 2.54 (3 H, s) ppm. MS (ESI) m/z: 533.2 (M+H)$^+$. Analytical HPLC: RT=4.25 min (method B).

Example 62

(E)-4-(5-(3-(5-Chloro-2-(1H-tetrazol-1-yl)phenyl)acryloyl)-4,5,6,7-tetrahydro-1H-pyrazolo[4,3-c]pyridine-4-carboxamido)benzoic acid

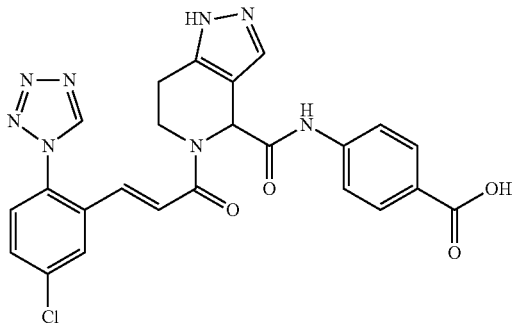 [SMILES: O=C(O)c1ccc(NC(=O)C2c3cn[nH]c3CCN2C(=O)/C=C/c2cc(Cl)ccc2-n2cnnn2)cc1]

Example 62 was made in a similar manner as Example 20 starting with commercially available 4,5,6,7-tetrahydro-1H-pyrazolo[4,3-c]pyridine. $^1$H NMR (400 MHz, DMSO-d$_6$) δ 12.48-12.85 (1 H, m), 10.68 (1 H, s), 9.87 (1 H, s), 8.49 (1 H, d, J=2.0 Hz), 7.86-7.97 (2 H, m), 7.65-7.81 (5 H, m), 7.63 (1 H, d, J=3.3 Hz), 6.95 (1 H, d, J=15.2 Hz), 5.89 (1 H, s), 4.53-4.68 (1 H, m), 3.76-3.94 (1 H, m), 2.92-3.14 (1 H, m), 2.77-2.87 (2 H, m) ppm. MS (ESI) m/z: 519.1 (M+H)$^+$. Analytical HPLC: RT=5.62 min.

Example 63

(E)-N-(4-(1H-imidazol-2-yl)phenyl)-5-(3-(3-chloro-2-fluoro-6-(1H-tetrazol-1-yl)phenyl)acryloyl)-1,3-dimethyl-4,5,6,7-tetrahydro-1H-pyrazolo[4,3-c]pyridine-4-carboxamide, TFA salt

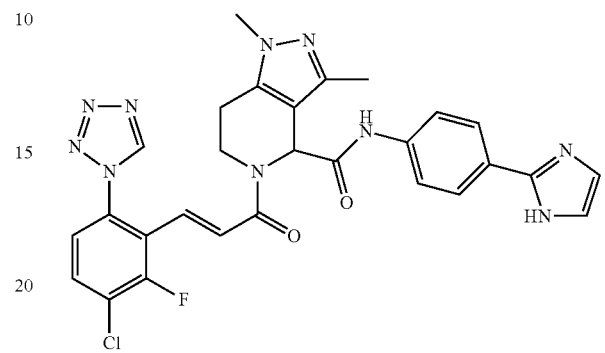

Example 63 was made in a similar manner as Example 60 substituting commercially available 4-(1H-imidazol-2-yl)aniline for 6-amino-3,4-dihydroquinolin-2(1H)-one for 6-amino-3,4-dihydroquinolin-2(1H)-one. $^1$H NMR (400 MHz, MeOD) δ 10.45 (1 H, br. s), 9.54 (1 H, s), 7.87 (3 H, s), 7.75-7.83 (1 H, m), 7.61 (2 H, s), 7.49 (1H, dd, J=8.6, 1.3 Hz), 6.99-7.23 (2H, m), 5.90 (1 H, s), 4.11-4.21 (1 H, m), 3.87-3.99 (1 H, m), 3.73 (3 H, s), 2.66-2.97 (2 H, m), 2.19 (3 H, s) ppm. MS (ESI) m/z: 578(M+H)$^+$. Analytical HPLC: RT=4.78 min (method B).

Example 64

(E)-4-(6-(3-(5-Chloro-2-(1H-tetrazol-1-yl)phenyl)acryloyl)-1,3-dimethyl-4,5,6,7-tetrahydro-1H-pyrazolo[3,4-c]pyridine-7-carboxamido)benzoic acid

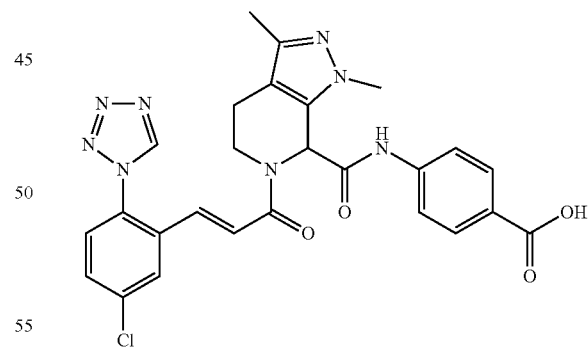

64A: 4-Hydroxy-N-(4-methoxybenzyl)pentanamide: 5-Methyldihydrofuran-2(3H)-one (30 g, 299.6 mmol) and p-methoxy benzylamine (45 g, 329.6 mmol) were heated at 85° C. for 16 h. The reaction was cooled to 60° C. and EtOAc was added. After further cooling to rt, petroleum ether was added and the crystallized product was filtered and dried under vacuum to give 46 g of 64A as a white solid. MS (ESI) m/z: 238.2 (M+H)$^+$.

64B: 5-(4-Methoxybenzylamino)pentan-2-ol: To a 0° C. solution of 64A (28 g, 117.6 mmol) in dry THF (250 mL)

was added borane-DMS complex (12.3 mL, 235.3 mmol). After 1 h at rt, the reaction was heated to reflux for 18 h. The solvent was removed and the residue was dissolved in EtOAc, washed with H$_2$O, brine, dried over Na$_2$SO$_4$, filtered and concentrated to give 28 g of 64B as a white solid. MS (ESI) m/z: 224.2 (M+H)$^+$.

64C: Ethyl 2-((4-hydroxypentyl)(4-methoxybenzyl)amino)-2-oxoacetate: To a 0° C. solution of 64B (28 g, 125.4 mmol) in dry THF (600 mL) was added TEA (35.49 mL, 250.78 mmol) and, slowly, ethyloxaloyl chloride (15.68 g, 138 mmol). After 2.5 h at rt, the reaction mixture was diluted with H$_2$O, extracted with EtOAc (2×), the combined organics were washed with brine, dried over Na$_2$SO$_4$, filtered and concentrated to give 37 g of 64C as a brown solid. MS (ESI) m/z: 324.2 (M+H)$^+$.

64D: Ethyl 2-((4-methoxybenzyl)(4-oxopentyl)amino)-2-oxoacetate: To a 0° C. solution of 64C (37 g, 114.44 mmol) in DCM (400 mL) was slowly added Dess-Martin periodinane (97 g, 228.88 mmol). After 3 h at rt, the reaction mixture was quenched with simultaneous addition of saturated Na$_2$SO$_3$ solution and saturated NaHCO$_3$ solution. The resultant clear solution was extracted with DCM twice. The combined organics were washed with H$_2$O, brine, dried over Na$_2$SO$_4$, filtered and concentrated to give 64D (36 g) as a brown solid. MS (ESI) m/z: 322.2 (M+H)$^+$.

64E: 4-Acetyl-3-hydroxy-1-(4-methoxybenzyl)-5,6-dihydropyridin-2(1H)-one: To a freshly prepared 0° C. solution of NaOMe (Na (8.3 g, 364.48 mmol) in MeOH was added 64D (78 g, 243 mmol) in MeOH (300 mL). The reaction mixture was heated at 60° C. for 3 h. The solvent was removed and the residue was quenched with 1N HCl solution, extracted with EtOAc twice, the combined organics were washed with H$_2$O, brine, dried over Na$_2$SO$_4$, filtered and concentrated to give 64E (10 g) as a brown liquid. MS (ESI) m/z: 276.2 (M+H)$^+$.

64F and 64G: 6-(4-Methoxybenzyl)-1,3-dimethyl-5,6-dihydro-1H-pyrazolo[3,4-c]pyridin-7(4H)-one and 6-(4-methoxybenzyl)-2,3-dimethyl-5,6-dihydro-2H-pyrazolo[3,4-c]pyridin-7(4H)-one: To a solution of 64E (10 g, 36.32 mmol) in EtOH (100 mL) was added K$_2$CO$_3$ (10 g, 72.64 mmol) and methyl hydrazine sulfate (6.28 g, 43.58 mmol) and the reaction mixture was heated to reflux for 18 h. The solvent was removed and the residue was diluted with H$_2$O, extracted with EtOAc twice, the combined organics were washed with H$_2$O, brine, dried over Na$_2$SO$_4$, filtered and concentrated. The crude was separated by silica gel column chromatography to give a mixture of 64F (2.5 g) as white solid and 64G (6.5 g) as white solid. MS (ESI) m/z: 286.2 (M+H)$^+$.

64H: 6-(4-Methoxybenzyl)-2,3-dimethyl-4,5,6,7-tetrahydro-2H-pyrazolo[3,4-c]pyridine: To a 0° C. solution of 64G (5 g, 17.52 mmol) in THF (50 mL) was added borane-DMS complex (3.32 mL, 35.05 mmol). After 1 h at rt, the reaction was heated to reflux for 18 h. The solvent was removed and the residue was quenched with MeOH. After heating to reflux for 18 h, excess MeOH was removed. The residue was dissolved in EtOAc, washed with H$_2$O, brine, dried over Na$_2$SO$_4$, filtered and concentrated to give 4.2 g of 64H as a white solid. MS (ESI) m/z: 272.2 (M+H)$^+$.

64I: 2,3-Dimethyl-4,5,6,7-tetrahydro-2H-pyrazolo[3,4-c]pyridine: 64H (4.2 g) in mEtOH (42 mL) was hydrogenated at atmospheric pressure in the presence of 10% Pd/C (420 mg) and Pd(OH)$_2$ (420 mg) for 3 days The reaction mixture was filtered through Celite® and washed twice with MeOH. The combined organics were evaporated to give 1.8 g of 64I as a white solid. MS (ESI) m/z: 152.0 (M+H)$^+$.

64J: 2,3-Dimethyl-4,5-dihydro-2H-pyrazolo[3,4-c]pyridine: 64I (150 mg) was oxidized as described in Example 20B to afford 150 mg of 64J as a pale yellow solid. MS (ESI) m/z: 150.0 (M+H)$^+$.

Example 64 (10 mg) was prepared from 64J (150 mg, 1.0 mmol), Intermediate 2, and Intermediate 6, as described for Example 20, followed by TFA deprotection. $^1$H NMR (400 MHz, DMSO-d$_6$) δ 12.68 (1 H, s), 10.74 (1 H, s), 9.83-9.86 (1 H, d, J=12.0 Hz), 8.47 (1 H, s), 7.87-7.93 (2 H, m), 7.61-7.77 (5 H, m), 6.90-6.96 (1 H, m), 6.54 (1 H, s), 5.84 (1 H, s), 4.52-4.55 (1 H, d, J=13.2 Hz), 3.69-3.75 (4 H, m), 2.58-2.54 (2H, m), 2.18 (3 H, s) ppm. MS (ESI) m/z: 547.0 (M+H)$^+$. Analytical HPLC: RT=9.08 min.

Example 65

(E)-4-(5-(3-(5-Chloro-2-(1H-tetrazol-1-yl)phenyl)acryloyl)-3-ethyl-1-methyl-4,5,6,7-tetrahydro-1H-pyrazolo[4,3-c]pyridine-4-carboxamido)benzoic acid, TFA salt

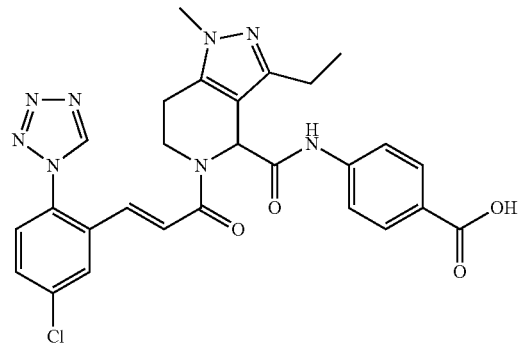 [SMILES: CCc1nn(C)c2c1C(C(=O)Nc1ccc(C(=O)O)cc1)N(C(=O)/C=C/c1cc(Cl)ccc1-n1cnnn1)CC2]

65A and 65B: tert-Butyl 3-ethyl-2-methyl-6,7-dihydro-2H-pyrazolo[4,3-c]pyridine-5(4H)-carboxylate and tert-butyl 3-ethyl-1-methyl-6,7-dihydro-1H-pyrazolo[4,3-c]pyridine-5(4H)-carboxylate: To a 0° C. solution of N-boc-4-piperidone (2.0 g, 0.0082 mol) in toluene (20 mL) was added LiHMDS (1.0 M in THF) (9 mL, 0.0091 mol) and stirred for 15 mins and the formed anion was allowed to sit for 1 minute before the addition of propionyl chloride (0.15 mL, 0.0016 mol) in one portion with stirring. The ice bath was removed and 10 mL of AcOH, 50 mL EtOH and 25 mL THF were added to form a homogeneous mixture. Methyl hydrazine (2.1 mL, 0.041 mol) was added and the mixture was heated to reflux for 4 h. The reaction mixture was added to 1.0 N NaOH solution and extracted with EtOAc. The organic layer was then washed with brine, and dried over Na$_2$SO$_4$. Purification by flash column chromatography and then, by chiral preparative HPLC afforded 600 mg of 65A and 300 mg of 65B. MS (ESI) m/z: 266.2 (M+H)+

65C: 3-Ethyl-1-methyl-4,5,6,7-tetrahydro-1H-pyrazolo[4,3-c]pyridine: To a 0° C. solution of 65B (120 mg) in DCM (2 mL) was added HCl in dioxane solution (0.12 mL). After 18 h at rt, the reaction was concentrated. The crude was dissolved in H$_2$O, added 10% NaHCO$_3$, extracted with EtOAc (4×20 mL), dried over Na$_2$SO$_4$, filtered and concentrated to afford 100 mg of 65C. MS (ESI) m/z: 166.2 (M+H)$^+$.

65D: 3-Ethyl-1-methyl-6,7-dihydro-1H-pyrazolo[4,3-c]pyridine: 65C (100 mg) was oxidized as described in Example 20B to afford 100 mg of 65D. MS (ESI) m/z: 164.0 (M+H)$^+$.

Example 65 was prepared from 65D, Intermediate 2 and Intermediate 6 in an Ugi reaction as described in Example 20 followed by TFA deprotection. $^1$H NMR (400 MHz, DMSO-$d_6$) δ 12.74 (1H, s), 10.70 (1 H, s), 9.87 (1 H, s), 8.45 (1 H, d, J=2.0 Hz), 7.88-7.93 (2 H, m), 7.71-7.79 (4 H, m), 7.60 (1 H, d, J=15.2 Hz), 6.97 (1 H, d, J=12.4 Hz), 5.86 (1 H, s), 4.50-4.54 (1 H, m), 3.93-4.00 (1 H, m), 3.63-3.69 (4 H, m), 2.50-2.88 (4 H, m), 0.96-1.00 (3 H, t, J=7.6 Hz) ppm. MS (ESI) m/z: 561.0 (M+H)$^+$. Analytical HPLC: RT=8.33 min.

Example 66

(E)-4-(1-Benzyl-5-(3-(3-chloro-2-fluoro-6-(1H-tetrazol-1-yl)phenyl)acryloyl)-3-methyl-4,5,6,7-tetrahydro-1H-pyrazolo[4,3-c]pyridine-4-carboxamido)benzoic acid

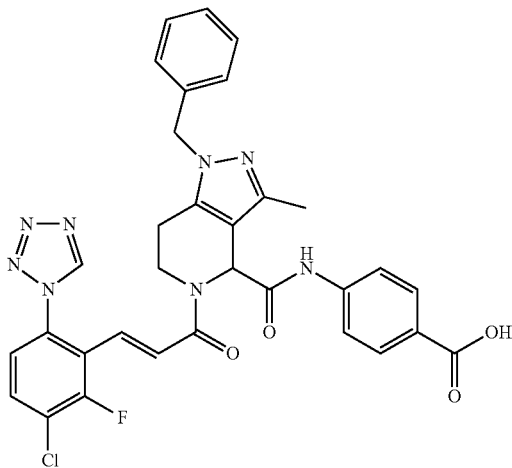 [SMILES: Cc1nn(Cc2ccccc2)c2c1C(C(=O)Nc1ccc(C(=O)O)cc1)N(C(=O)/C=C/c1c(-n3cnnn3)ccc(Cl)c1F)CC2]

66A: tert-Butyl 1-benzyl-3-methyl-6,7-dihydro-1H-pyrazolo[4,3-c]pyridine-5(4H)-carboxylate: tert-Butyl 3-acetyl-4-oxopiperidine-1-carboxylate (4.83 g, 20.0 mmol) TEA (5.58 mL, 40.0 mmol) and benzyl hydrazine, 2 HCl (4.68 g, 24.00 mmol) were combined in EtOH (50 mL). After 4 h, the solvent was removed in vacuo and the crude product was purified by flash chromatography to provide 66A (2.84 g, 44%) as a mixture of regioisomers MS (ESI) m/z: 328 (M+H)$^+$.

66B: To 66A (750 mg, 2.29 mmol) was added 10 mL of a 50% solution of TFA in DCM. The mixture was stirred at room temperature for 30 min and then basified by adding a solution of saturated NaHCO$_3$. The organic portion was dried over MgSO$_4$, filtered and concentrated providing 66B (502 mg, 94%) as a colorless oil. MS (ESI) m/z: 228 (M+H)$^+$.

66C: 2-Benzyl-3-methyl-6,7-dihydro-2H-pyrazolo[4,3-c] pyridine: IBX (115 mg, 0.409 mmol) was suspended in DMSO (10 mL) and stirred at rt for 0.5 h. The IBX solution was added dropwise to a solution of 66B (1.08 g, 4.75 mmol) in DMSO (10 mL). After stirring for 45 min, the reaction was stopped by addition of 10 mL of 10% aqueous Na$_2$S2O3 followed by 10 mL of saturated aqueous NaHCO$_3$. The mixture was extracted with diethyl ether 2×200 mL. The organic portion was dried over anhydrous MgSO$_4$, filtered and then solvent was removed to give 66C (1.01 g, 4.48 mol, 100% yield). MS (ESI) m/z: 226 (M+H)$^+$.

66D: tert-Butyl 4-(2-benzyl-3-methyl-5-(2,2,2-trifluoroacetyl)-4,5,6,7-tetrahydro-2H-pyrazolo[4,3-c]pyridine-4-carboxamido)benzoate: To a solution of crude 66C (1.01 g, 4.48 mmol) was added tert-butyl 4-cyanobenzoate (0.911 g, 4.48 mmol) followed by 2,2,2-trifluoroacetic acid (0.345 mL, 4.48 mmol). After 18 h, the reaction mixture was transferred to a separatory funnel, washed with saturated NaHCO$_3$ (10 mL) and the organic layer was dried over MgSO$_4$, filtered and concentrated. The crude solid was purified by preparative HPLC to provide 66D (676 mg, 28%) as a green solid. MS (ESI) m/z: 543 (M+H)$^+$.

66E: tert-Butyl 4-(1-benzyl-3-methyl-4,5,6,7-tetrahydro-1H-pyrazolo[4,3-c]pyridine-4-carboxamido)benzoate: To a solution of 66D (20 mg, 0.037 mmol) in EtOH (1 mL) was added NaBH$_4$ (6.97 mg, 0.184 mmol). After 1 h, the solvent was removed and the residue was partitioned between EtOAc (50 mL) and saturated NaHCO$_3$ (10 mL). The organic portion was dried over anhydrous MgSO$_4$, filtered, and the solvent concentrated to give 66E (16 mg, 97%) as a white solid. MS (ESI) m/z: 447.0 (M+H)$^+$.

66F: (E)-tert-Butyl 4-(1-benzyl-5-(3-(3-chloro-2-fluoro-6-(1H-tetrazol-1-yl)phenyl)acryloyl)-3-methyl-4,5,6,7-tetrahydro-1H-pyrazolo[4,3-c]pyridine-4-carboxamido)benzoate: Intermediate 3A (9.63 mg, 0.036 mmol) was suspended in DCM (0.5 mL) and 1-chloro-N,N,2-trimethylprop-1-en-1-amine (6.16 µl, 0.047 mmol) was added. After 1 h, added 67E (16 mg, 0.036 mmol) in DCM (0.5 mL) followed by pyridine (0.012 mL, 0.143 mmol) and the mixture was stirred at rt for 18 h. The solvent was removed in vacuo and the crude regioisomers were separated by preparative HPLC providing 66F (9.7 mg, 39%) as a white solid. MS (ESI) m/z: 697 (M+H)$^+$.

Example 66: To 66F (9.5 mg, 0.014 mmol) was added 1 mL of TFA (50% solution in DCM) and after 3 h, the solvent was removed in vacuo providing Example 66 (2.56 mg) as a white solid. $^1$H NMR (500 MHz, DMSO-$d_6$) δ 10.72 (1 H, s), 9.84 (1 H, s), 7.87-7.99 (3 H, m), 7.72 (2 H, d, J=8.80 Hz), 7.65 (1 H, d, J=8.80 Hz), 7.34 (2 H, t, J=7.43 Hz), 7.25-7.30 (1 H, m), 7.18 (2 H, d, J=7.15 Hz), 7.12 (1 H, d, J=15.68 Hz), 6.93 (1 H, d, J=15.96 Hz), 5.83 (1 H, s), 5.22 (1 H, d, J=15.41 Hz), 5.16 (1 H, d, J=15.41 Hz), 4.11-4.17 (1 H, m), 3.86-3.95 (1 H, m), 2.84-2.91 (1 H, m), 2.63 (1 H, d, J=1.93 Hz), 2.13 (3 H, s) ppm. MS (ESI) m/z: 641 (M+H)$^+$. Analytical HPLC: RT=8.23 min.

Example 67

(E)-4-(5-(3-(5-Chloro-2-(1H-tetrazol-1-yl)phenyl)acryloyl)-2,3-dimethyl-4,5,6,7-tetrahydro-1H-pyrazolo[4,3-c]pyridine-4-carboxamido)benzoic acid

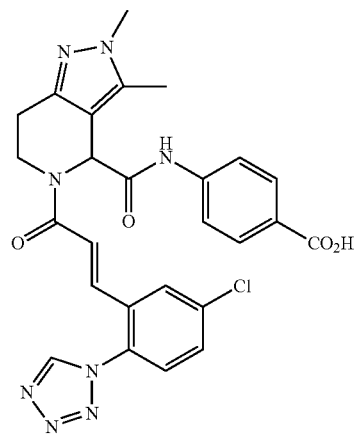 [SMILES: Cc1c2c(nn1C)CCN(C(=O)/C=C/c1cc(Cl)ccc1-n1cnnn1)C2C(=O)Nc1ccc(C(=O)O)cc1]

Example 67 (15 mg) was prepared from 61G (150 mg, 1.0 mmol) (mixture of isomers), Intermediate 2, and Intermediate 6, as described for Example 20, followed by HCl deprotection. Example 67 separated as the second of two isomers by prep HPLC $^1$H NMR (400 MHz, CDCl$_3$) δ 9.55

(1 H, s), 8.24 (1 H, s), 7.99 (2 H, d, J=8.8 Hz), 7.68 (3H, d, J=8.4 Hz), 7.59 (1 H, d, J=8.4 Hz), 7.39 (1H, d, J=14.8 Hz), 7.24 (1 H, d, J=15.2 Hz), 6.08 (1 H, s), 4.43 (1 H, bs), 3.86-3.92 (4 H, m), 2.94 (2 H, bs), 2.37 (3 H, s). MS (ESI) m/z: 547.0 (M+H)⁺. Analytical HPLC: RT=9.54 min.

Example 68

(E)-N-(4-(1H-imidazol-2-yl)phenyl)-5-(3-(5-chloro-2-(1H-tetrazol-1-yl)phenyl)acryloyl)-2,3-dimethyl-4,5,6,7-tetrahydro-2H-pyrazolo[4,3-c]pyridine-4-carboxamide, TFA salt

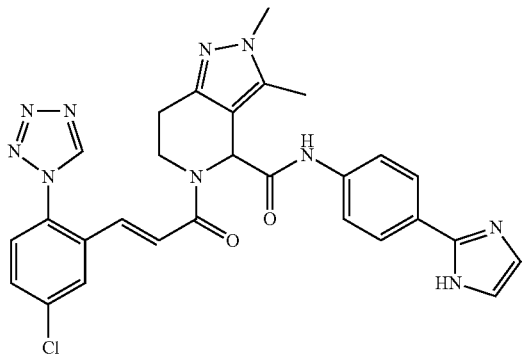 [SMILES: Cc1c2c(nn1C)CCN(C(=O)/C=C/c1cc(Cl)ccc1-n1cnnn1)C2C(=O)Nc1ccc(-c2ncc[nH]2)cc1]

Example 68 was made in a similar manner as Example 67 using 5-(tert-butoxycarbonyl)-2,3-dimethyl-4,5,6,7-tetrahydro-2H-pyrazolo[4,3-c]pyridine-4-carboxylic acid and commercially available 4-(1H-imidazol-2-yl)aniline for 6-amino-3,4-dihydroquinolin-2(1 H)-one. ¹H NMR (400 MHz, MeOD) δ 9.55 (1 H, s), 8.24 (1H, d, J=2.0 Hz), 7.89 (4 H, s), 7.66-7.74 (1 H, m), 7.56-7.65 (3 H, m), 7.41 (1 H, d, J=15.4 Hz), 7.17-7.27 (1 H, J=15.4 Hz), 5.95 (1 H, s), 4.30-4.40 (1 H, m), 3.98 (1 H, ddd, J=14.1, 8.6, 5.8 Hz), 3.78 (3 H, s), 2.85-2.95 (2 H, m), 2.31 (3 H, s) ppm. MS (ESI) m/z: 569 (M+H)⁺. Analytical HPLC: RT=4.64 min.

Example 69

(E)-4-(5-(3-(5-Chloro-2-(1H-tetrazol-1-yl)phenyl) acryloyl)-2-methyl-4,5,6,7-tetrahydro-2H-pyrazolo [4,3-c]pyridine-4-carboxamido)benzoic acid, TFA salt

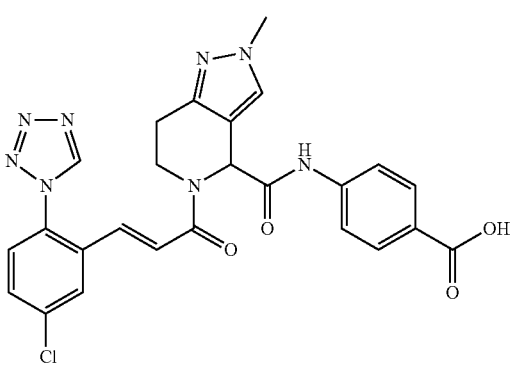 [SMILES: Cn1cc2c(n1)CCN(C(=O)/C=C/c1cc(Cl)ccc1-n1cnnn1)C2C(=O)Nc1ccc(C(=O)O)cc1]

69A: tert-Butyl 4-(2-methyl hydrazono) piperidine-1-carboxylate: To a solution of tert-butyl 4-oxopiperidine-1-carboxylate (2 g) in EtOH (16 mL) was added methyl hydrazine sulphate (2.17 g) and K₂CO₃ (2.5 g). The reaction was heated to reflux for 12 h. The reaction was concentrated to dryness to give 2.5 g of 69A as a colorless gum. ¹H NMR (400 MHz, MeOD) δ 3.48-3.57 (4 H, m), 3.3 (3 H, s), 2.38 (4 H, t, J=8.0 Hz), 1.46 (9 H, s) ppm.

69B: tert-Butyl 2-methyl-6,7-dihydro-2H-pyrazolo[4,3-c] pyridine-5(4 H)-carboxylate: 69A (500 bs) was heated to 90° C. in dimethylformamide dimetylacetal (2.5 mL) and DMF (2.5 mL) for 12 h. The reaction was concentrated to dryness and purified by column chromatography to give 400 mg of 69B as pale yellow oil. MS (ESI) m/z: 238.2 (M+H)⁺.

69C: 2-Methyl-4, 5, 6, 7-tetrahydro-2H-pyrazolo[4,3-c] pyridine: To a 0° C. solution of 69B (0.23 g) in dioxane (5 mL) was added HCl in dioxane (4M, 2 mL). After 18 h at rt, the reaction was concentrated. The crude was dissolved in H₂O and 10% NaHCO₃ was added. The aqueous layer was extracted with EtOAc (4×20 mL), dried over Na₂SO₄, filtered and concentrated to afford 120 mg of 69C as a pale yellow solid. ¹H NMR (400 MHz, CDCl₃) δ 7.04 (1 H, s), 3.86 (5 H, d, J=9.0 Hz), 3.13 (2 H, t, J=6.0 Hz), 2.73 (2H, t, J=6.0 Hz) ppm.

69D: 2-Methyl-6,7-dihydro-2H-pyrazolo[4,3-c]pyridine: 69C (107 mg) was oxidized as described in Example 20B to afford 80 mg of 69D. ¹H NMR (300 MHz, CDCl₃) δ 8.30 (1 H, s), 7.36 (1 H, s), 3.89 (3 H, s), 3.85 (2 H, d, J=6.0 Hz), 2.77 (2 H, t, J=9.0 Hz) ppm.

Example 69: Example 69 (40 mg) was prepared by an Ugi reaction as described in Example 20 using 69D, Intermediate 2 and Intermediate 6 followed by TFA deprotection. ¹H NMR (400 MHz, DMSO-d₆) δ 12.77 (1 H, bs), 10.71 (1 H, s), 9.88 (1 H, s), 8.49 (1 H, s), 7.89 (2 H, d, J=8.0 Hz), 7.65-7.77 (6 H, m), 6.92 (1 H, d, J=15.2 Hz), 5.84 (1 H, s), 5.76 (3 H, s), 4.50-4.61 (2 H, m), 3.78 (4 H, s), 2.75 (2 H, s), 1.99-2.01 (1 H, m), 1.50 (2 H, d, J=7.2 Hz) ppm. MS (ESI) m/z: 532.8 (M+H)⁺. Analytical HPLC: RT=8.66 min Example 70

(E)-4-(5-(3-(5-Chloro-2-(1H-tetrazol-1-yl)phenyl) acryloyl)-2-phenyl-4,5,6,7-tetrahydro-2H-pyrazolo [4,3-c]pyridine-4-carboxamido)benzoic acid

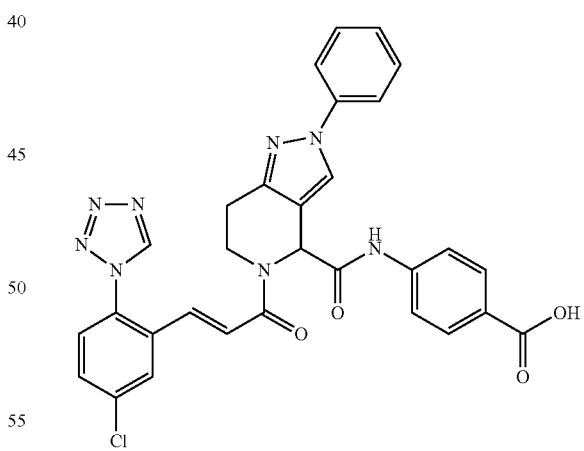

70A: (E)-tert-Butyl 3-((dimethylamino)methylene)-4-oxopiperidine-1-carboxylate: To a solution of tert-butyl 4-oxopiperidine-1-carboxylate (10 g) in DMF (50 mL) was added DMF-DMA (50 mL). The reaction was heated to reflux and after 4 h the solvents were removed. The residue was quenched with H₂O, extracted with EtOAc, dried over Na₂SO₄, filtered and concentrated to afford 11 g of 70A. MS (ESI) m/z: 255 (M+H)+.

70B: tert-Butyl 2-phenyl-6,7-dihydro 2H-pyrazolo[4,3-c] pyridine-5(4H)-carboxylate: To a solution of 70A (1 g, 4.9 mmol) in EtOH (20 mL) was added phenyl hydrazine (0.6 g, 5.8 m mol) and the reaction was heated to 80° C. for 6 h. The reaction mixture was concentrated and quenched with H₂O, extracted with EtOAc twice; the combined organics were washed with saturated NaHCO₃ solution, H₂O, brine, dried over Na₂SO₄, filtered and concentrated. The crude was purified by flash column chromatography to afford 0.4 g of 70B. MS (ESI) m/z: 300 (M+H)+.

70C: 2-Phenyl-4, 5, 6, 7-tetrahydro-2H-pyrazolo[4,3-c]pyridine: To a 0° C. solution of 70B (600 mg) in DCM (10 mL), HCl in Dioxane (6 mL) was slowly added. After 5 h at rt, the reaction was concentrated and quenched with H₂O, basified using NaOH, then extracted with EtOAc twice; the combined organics were washed with H₂O, brine, dried over Na₂SO₄, filtered and concentrated to afford 0.4 g of 70C. MS (ESI) m/z: 200 (M+H)+

70D: 2-Phenyl-6,7-dihydro-2H-pyrazolo[4,3-c]pyridine: To a 0° C. solution of 70C (0.2 g, 1.0 mmol) in EtOH (2 mL) were added sodium acetate (164 mg, 2.0 mmol) and Iodine (508 mg, 2.0 mmol). After 2 h at rt, the reaction mixture was quenched with H₂O and then extracted with DCM. The combined organics were washed with H₂O, brine, Na₂S2O3, concentrated to get 0.15 g of 70D. MS (ESI) m/z: 198 (M+H)⁺.

Example 70: Example 70 (12 mg) was prepared by Ugi reaction as described in Example 20 using 70D, Intermediate 2 and Intermediate 6 followed by TFA deprotection. ¹H NMR (400 MHz, DMSO-d₆) δ 12.7 (1 H, bs), 10.74 (1 H, s), 9.89 (1 H, s), 8.43-8.60 (2 H, m), 7.94-7.69 (9 H, m), 7.48 (2 H, t, J=7.6 Hz), 6.98-6.95 (2 H, m), 6.01 (1 H, s), 4.70 (1 H, d, J=14.8 Hz), 3.80-3.60 (1 H, m), 2.80-2.90 (2 H, m) ppm. MS (ESI) m/z: 594.8 (M+H)⁺. Analytical HPLC: RT=9.92 min.

Example 71

(E)-7-(3-(3-Chloro-2-fluoro-6-(1H-tetrazol-1-yl)phenyl)acryloyl)-N-(1H-indazol-6-yl)-3-(4-methylpiperazin-1-yl)-5,6,7,8-tetrahydroimidazo[1,5-a]pyrazine-8-carboxamide

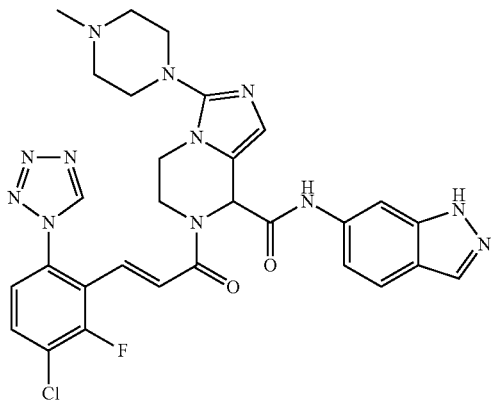 [SMILES: CN1CCN(c2ncc3n2CCN(C(=O)/C=C/c2c(-n4cnnn4)ccc(Cl)c2F)C3C(=O)Nc2ccc3cn[nH]c3c2)CC1]

71A: 7-Benzyl-3-bromo-5,6,7,8-tetrahydroimidazo[1,5-a]pyrazine: The synthesis of 7-benzyl-3-bromo-5,6,7,8-tetrahydroimidazo[1,5-a]pyrazine is described in PCT/IB03/00998 WO 03/076427 A1. A solution of 7-benzyl-5,6,7,8-tetrahydro imidazo[1,5-a]pyrazine (450 mg, 2.110 mmol) in THF was cooled in dry ice acetone bath. n-Butyllithium (0.928 mL, 2.321 mmol) was added dropwise. After 15 mins, bromine (0.120 mL, 2.321 mmol) was added dropwise. After 1 h, the solution was poured into H₂O and extracted with DCM (3×). Purified by normal phase chromatography to afford 7-benzyl-1-bromo-5,6,7,8-tetrahydroimidazo[1,5-a]pyrazine (112 mg, 0.383 mmol, 18.2% yield) and 71A (260 mg, 0.890 mmol, 42.2% yield). ¹H NMR (400 MHz, CDCl₃) δ 7.18-7.44 (m, 5 H) 6.71 (s, 1 H) 3.78-3.95 (m, 2 H) 3.68 (s, 2 H) 3.60 (s, 2 H) 2.75-2.97 (m, 2 H) ppm.

71B: 7-Benzyl-3-(4-methylpiperazin-1-yl)-5,6,7,8-tetrahydroimidazo[1,5-a]pyrazine: A solution of 71A (100 mg, 0.342 mmol) and N-methylpiperazine (100 μL, 0.902 mmol) was heated at 160° C. for 2 days. To the reaction mixture was added H₂O and the mixture was extracted with DCM (3×). The organic layer was concentrated and placed under vacuum to give 71B (87 mg, 82%) which was used without further purification. MS(ESI) m/z: 312.2 (M+H)⁺.

71C: 3-(4-Methylpiperazin-1-yl)-5,6,7,8-tetrahydroimidazo[1,5-a]pyrazine: To a solution of 71B (200 mg, 0.642 mmol) in acetic acid (2 mL) under N₂ was added 10% Pd/C (30 mg, 0.282 mmol). The mixture was hydrogenated under hydrogen balloon overnight. After filtration and concentration, the mixture was purified by reverse phase HPLC. Product containing fractions were concentrated and the TFA salt was dissolved in EtOH and put through PL-HCO3 MPSPE (500 mg 0.9 mmol) basic cartridge to give 71C (50 mg, 23%) as brownish glass MS(ESI) m/z: 222.2 (M+H)+

71D: 3-(4-Methylpiperazin-1-yl)-5,6-dihydroimidazo[1,5-a]pyrazine: 71D was prepared in a similar manner as Intermediate 18 using intermediate 71C. MS(ESI) m/z: 220.2 (M+H)⁺.

Example 71: Example 71 was prepared in a similar manner as Example 20 using Intermediate 3A, 8 and 71D followed by deprotection using 1:1 TFA/DCM solution for 30 min at rt. The reaction was concentrated and purified by reverse phase HPLC to afford Example 71 (1.5 mg, 1%) as yellow glass ¹H NMR (400 MHz, MeOD) δ 9.55-9.60 (m, 1 H) 8.05 (s, 1 H) 7.98 (s, 1 H) 7.82 (t, J=8.24 Hz, 1 H) 7.72 (d, J=8.79 Hz, 1 H) 7.51 (d, J=8.25 Hz, 1 H) 7.26 (s, 1 H) 7.11-7.21 (m, 2 H) 7.03 (d, J=15.94 Hz, 1H) 6.01-6.07 (m, 1 H) 4.30-4.40 (m, 1 H) 4.30-4.41 (m, 1 H) 4.13-4.23 (m, 1 H) 4.12-4.22 (m, 2 H) 3.99-4.10 (m, 1 H) 3.46-3.71 (m, 6 H) 2.99-3.04 (m, 3 H) ppm. MS(ESI) m/z: 631.3 (M+H)⁺. Analytical HPLC: RT=4.48 min.

Example 72

(E)-4-(2-Benzyl-5-(3-(5-chloro-2-(1H-tetrazol-1-yl)phenyl)acryloyl)-4,5,6,7-tetrahydro-2H-pyrazolo[4,3-c]pyridine-4-carboxamido)benzoic acid

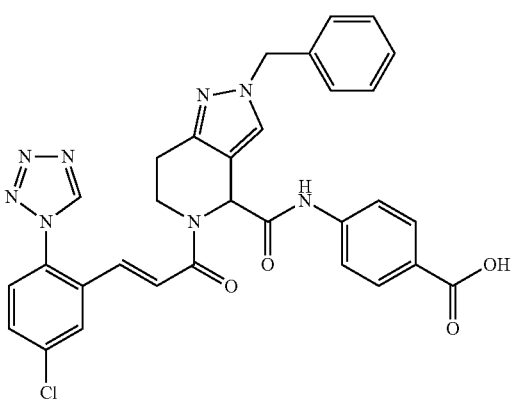 [SMILES: O=C(O)c1ccc(NC(=O)C2c3cn(Cc4ccccc4)nc3CCN2C(=O)/C=C/c2cc(Cl)ccc2-n2cnnn2)cc1]

72A: (E)-tert-Butyl 2-benzyl-6,7-dihydro 2H-pyrazolo[4,3-c]pyridine-5(4H)-carboxylate: To a solution of 72A (2 g, 7.8 mmol) in EtOH (20 mL) was added benzyl hydrazine (1.5 g, 7.8 mmol) and $K_2CO_3$ (3.2 g, 23 mmol). The reaction mixture was heated for 6 h at 75° C. in a sealed tube. The reaction mixture was concentrated and quenched with $H_2O$, extracted with EtOAc twice; the combined organics were washed with saturated $NaHCO_3$ solution, $H_2O$, brine, dried over $Na_2SO_4$, filtered and concentrated. The crude was purified by silica gel column chromatography to afford 1.3 g of 72A. MS (ESI) m/z: 314 (M+H)$^+$.

72B: 2-Benzyl-4, 5, 6, 7-tetrahydro-2H-pyrazolo[4,3-c]pyridine: To a 0° C. solution of 72A (1.0 g) in 1, 4-dioxane (10 mL) was added 4N HCl in dioxane (10 mL). After 1 h at rt, the reaction mixture was concentrated and quenched with $H_2O$, basified with NaOH, then extracted with EtOAc twice. The combined organics were washed with $H_2O$, brine, dried over $Na_2SO_4$, concentrated to give 0.050 g of 72B. MS (ESI) m/z: 214 (M+H)$^+$.

72C: 2-Benzyl-6,7-dihydro-2H-pyrazolo[4,3-c]pyridine: To a 0° C. solution of 72B (0.2 g, 0.9 mmol) in DCM (4 mL) was added mercuric (II) oxide (304 mg, 1.4 mmol), and Iodine (356 mg, 1.4 mmol). After 2 h at rt, the reaction mixture was quenched with $H_2O$ then extracted with DCM. The combined organics were washed with $H_2O$, brine, $Na_2S2O3$, concentrated to get 0.15 g of 72C. MS (ESI) m/z: 212 (M+H)$^+$.

Example 72: Example 72 (10 mg) was prepared by an Ugi reaction, as described in Example 20, using 72C, Intermediate 2 and Intermediate 6, followed by TFA deprotection. $^1$H NMR (400 MHz, DMSO-d$_6$) δ 12.7 (1 H, bs), 10.75 (1 H, s), 9.87 (1 H, s), 7.89 (1 H, d, J=8.8 Hz), 7.62-7.80 (4 H, m), 7.54 (1 H, s), 7.26-7.36 (2 H, m), 7.20-7.17 (2 H, m), 6.94 (1 H, d, J=5.2 Hz), 5.30 (1 H, d, J=6.4 Hz), 4.64-4.60 (1 H, m), 3.70-3.90 (1 H, m), 2.94-2.90 (2 H, m) ppm. MS (ESI) m/z: 608.8 (M+H)$^+$. Analytical HPLC: RT=9.61 min.

Example 73

(E)-4-(6-(3-(5-Chloro-2-(1H-tetrazol-1-yl)phenyl)acryloyl)-1,3-dimethyl-4,5,6,7-tetrahydro-1H-pyrazolo[3,4-c]pyridine-7-carboxamido)benzoic acid

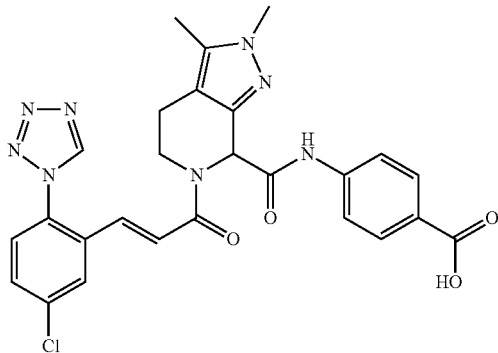 [SMILES: Cc1c2c(nn1C)C(C(=O)Nc1ccc(C(=O)O)cc1)N(C(=O)/C=C/c1cc(Cl)ccc1-n1cnnn1)CC2]

Example 73 (8 mg) was prepared in a similar manner as Example 65. $^1$H NMR (400 MHz, DMSO-d$_6$) δ 12.74 (1 H, s), 10.55 (1 H, s), 9.86-9.87 (1 H, d, J=6.8 Hz), 8.48 (1 H, s), 7.88-7.90 (2 H, d, J=4.8 Hz), 7.57-7.83 (5 H, m), 6.96-7.02 (1 H, m), 6.20 (1 H, s), 4.92-4.52 (1 H, d, J=14.0 Hz), 3.63-3.80 (4 H, m), 2.55-2.54 (2 H, m), 2.04 (3H, s) ppm. MS (ESI) m/z: 547.0 (M+H)$^+$. Analytical HPLC: RT=8.70 min.

Example 74

(E)-4-(6-(3-(3-Chloro-2-fluoro-6-(1H-tetrazol-1-yl)phenyl)acryloyl)-1-ethyl-3-methyl-4,5,6,7-tetrahydro-1H-pyrazolo[3,4-c]pyridine-7-carboxamido)benzoic acid

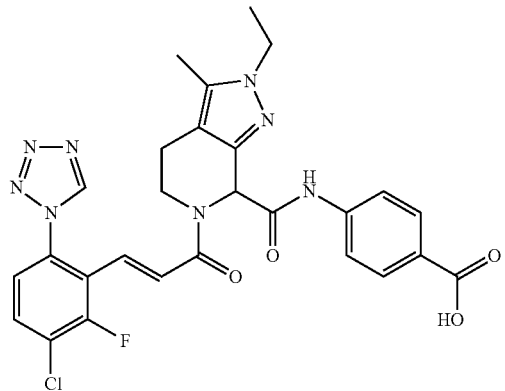 [SMILES: CCn1nc2c(c1C)CCN(C(=O)/C=C/c1c(-n3cnnn3)ccc(Cl)c1F)C2C(=O)Nc1ccc(C(=O)O)cc1]

74A: tert-butyl 1-ethyl-3-methyl-4,5-dihydro-1H-pyrazolo[3,4-c]pyridine-6(7H)-carboxylate and 74B: tert-butyl 2-ethyl-3-methyl-4,5-dihydro-2H-pyrazolo[3,4-c]pyridine-6(7H)-carboxylate: To a 0° C. solution of N-boc-3-piperidone (2.0 g, 0.0082 mol) in toluene (20 mL) was added LiHMDS (1.0 M in THF) (9.0 mL, 0.0091 mol). After stirring for 15 mins, the formed anion was allowed to sit for 1 min before the addition of acetyl chloride (0.3 mL, 0.0041 mol). The ice bath was removed and 10 mL of AcOH, 50 mL EtOH, 25 mL THF were added, followed by ethyl hydrazine oxalate (6.1 g, 0.041 mol). After heating at reflux for 3 h, to the reaction was added to 1.0 N NaOH solution and extracted with EtOAc. The organic layer was washed with brine, dried over $Na_2SO_4$, and evaporated under reduced pressure. Purification by flash column chromatography followed by chiral preparative HPLC separated both regioisomers: 74A (250 mg) and 74B (300 mg). MS (ESI) m/z: 266.2 (M+H)$^+$.

74C: 1-ethyl-3-methyl-4,5-dihydro-1H-pyrazolo[3,4-c]pyridine: 74A was deprotected with TFA, free-based and oxidized as described in Example 20B to afford 74C. MS (ESI) m/z: 164.2 (M+H)$^+$.

Example 74 (12 mg) was prepared in a similar manner as Example 20 by an Ugi reaction using 74C, Intermediate 3A, and Intermediate 6, followed by TFA deprotection. $^1$H NMR (400 MHz, DMSO-d$_6$) δ 10.08 (1 H, s), 9.87 (1 H, s), 7.95 (1 H, t, J=8.4 Hz), 7.81 (2 H, d, J=8.4 Hz), 7.66 (1 H, d, J=8.8 Hz), 7.56 (2H, d, J=8.0 Hz), 6.96 (1 H, d, J=15.6 Hz), 6.81 (1 H, d, J=16.4 Hz), 5.13-5.22 (1 H, m), 3.98-4.06 (2 H, m), 2.49-2.67 (2 H, m), 2.07-2.33 (5 H, m), 1.24-1.30 (3 H, m) ppm. MS (ESI) m/z: 579.2.0 (M+H)$^+$. Analytical HPLC: RT=8.41 min.

Example 75

(E)-4-(5-(3-(3-chloro-2-fluoro-6-(1H-tetrazol-1-yl)phenyl)acryloyl)-2,3-dimethyl-4,5,6,7-tetrahydro-2H-pyrazolo[4,3-c]pyridine-4-carboxamido)benzoic acid, TFA salt

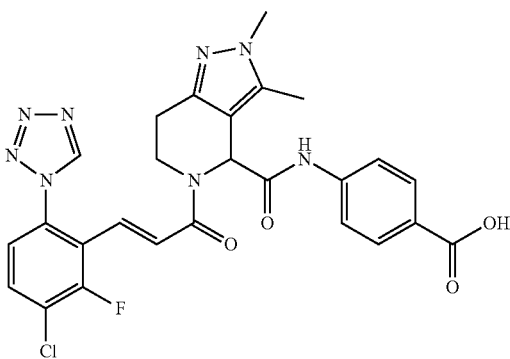 [SMILES: Cc1c2c(nn1C)CCN(C(=O)/C=C/c1c(-n3cnnn3)ccc(Cl)c1F)C2C(=O)Nc1ccc(C(=O)O)cc1]

Example 75 was made in a similar manner as Example 68, substituting Intermediate 3A for Intermediate 2. $^1$H NMR (400 MHz, DMSO-$d_6$) δ 12.70 (1 H, s), 10.64 (1H, s), 9.83 (1 H, s), 7.90-7.98 (3 H, m), 7.64-7.88 (3 H, m), 7.13 (1 H, d, J=16 Hz), 6.94 (1 H, d, J=15.6 Hz), 5.83 (1 H, s), 3.91-4.05 (2 H, m), 3.65 (3 H, s), 2.59-2.73 (3 H, m), 2.23 (3 H, s) ppm. MS (ESI) m/z: 565.2 (M+H)$^+$. Analytical HPLC: RT=7.93 min.

Example 76

(E)-tert-butyl 4-(5-(3-(3-chloro-2-fluoro-6-(1H-tetrazol-1-yl)phenyl)acryloyl)-3-methyl-4,5,6,7-tetrahydro-2H-pyrazolo[4,3-c]pyridine-4-carboxamido)benzoate, TFA salt

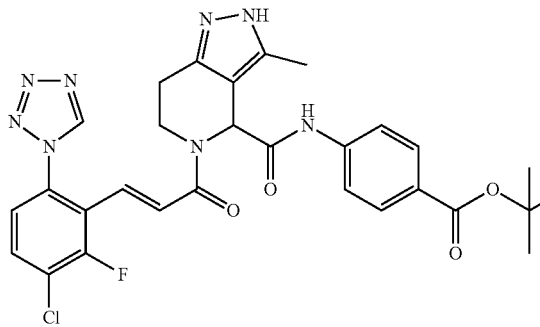

76A: 3-Methyl-6,7-dihydro-1H-pyrazolo[4,3-c]pyridine: To a solution of 3-methyl-4,5,6,7-tetrahydro-1H-pyrazolo[4,3-c]pyridine (127 mg, 0.926 mmol) in DCM (1 mL) and MeOH (0.100 mL) at 0° C. was portionwise added NCS (136 mg, 1.018 mmol). After 1 h at rt, DBU (0.153 mL, 1.018 mmol) was added and the reaction was stirred for 1 h. The reaction mixture was concentrated in vacuo, yielding an oily residue, which was subjected to the following reaction without further purification. MS (ESI) m/z: 136.0 (M+H)$^+$.

Example 76 was prepared in an Ugi reaction in a similar manner as Example 20 using 76A, Intermediate 3A and Intermediate 6. $^1$H NMR (400 MHz, MeOD) δ 9.58 (1 H, s), 7.94 (2 H, d, J=8.8 Hz), 7.82 (1 H, t, J=8.2 Hz), 7.69 (2H, d, J=8.8 Hz), 7.45-7.58 (1 H, m), 6.99-7.26 (2 H, m), 6.03 (1H, s), 4.10-4.33 (1 H, m), 3.82-4.01 (1H, m), 2.75-3.03 (2 H, m), 2.34 (3 H, s), 1.58-1.72 (9 H, m) ppm. MS (ESI) m/z: 607.0 (M+H)$^+$. Analytical HPLC: RT=8.54 min

Example 77

(E)-4-(5-(3-(3-chloro-2-fluoro-6-(1H-tetrazol-1-yl)phenyl)acryloyl)-3-methyl-4,5,6,7-tetrahydro-2H-pyrazolo[4,3-c]pyridine-4-carboxamido)benzoic acid, TFA salt

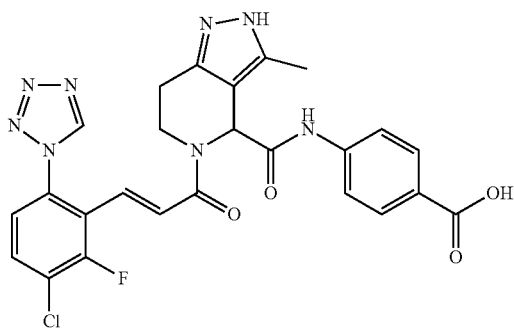 [SMILES: Cc1[nH]nc2c1C(C(=O)Nc1ccc(C(=O)O)cc1)N(C(=O)/C=C/c1c(-n3cnnn3)ccc(Cl)c1F)CC2]

Example 77 was made by subjecting Example 76 to TFA deprotection. $^1$H NMR (400 MHz, MeOD) δ 9.57 (1 H, s), 8.01 (2 H, d, J=8.8 Hz), 7.82 (1 H, t, J=8.0 Hz), 7.71 (2 H, d, J=8.5 Hz), 7.51 (1 H, d, J=8.5 Hz), 6.99-7.28 (2 H, m), 6.04 (1 H, s), 4.17 (1 H, br. s), 3.82-3.97 (1 H, m), 2.77-3.04 (2 H, m), 2.35 (3 H, s) ppm. MS (ESI) m/z: 550.9 (M+H)$^+$. Analytical HPLC: RT=6.19 min.

Example 78

(E)-4-(3-bromo-6-(3-(5-chloro-2-(1H-tetrazol-1-yl)phenyl)acryloyl)-5,6,7,8-tetrahydro-1,6-naphthyridine-5-carboxamido)benzoic acid, TFA salt

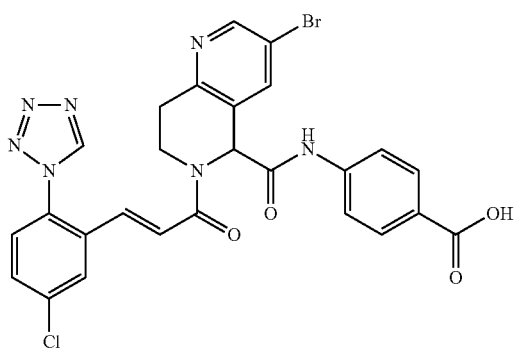 [SMILES: O=C(O)c1ccc(NC(=O)C2c3cc(Br)cnc3CCN2C(=O)/C=C/c2cc(Cl)ccc2-n2cnnn2)cc1]

78A: (E)-Methyl 4-(3-bromo-6-(3-(5-chloro-2-(1H-tetrazol-1-yl)phenyl)acryloyl)-5,6,7,8-tetrahydro-1,6-naphthyridine-5-carboxamido)benzoate: Methyl ester 78A was made in a similar manner as Example 53 starting with commercially available 3-bromo-5,6,7,8-tetrahydro-1,6-naphthyridine. MS (ESI) m/z: 621 (M+H)$^+$.

Example 78 was made from 78A in a similar manner as Example 45. $^1$H NMR (400 MHz, DMSO-$d_6$) δ 12.77 (1 H, br. s), 10.76 (1 H, s), 9.88 (1 H, s), 8.58-8.67 (1 H, m), 8.48 (1H, d, J=2.27 Hz), 8.22 (1H, d, J=2.02 Hz), 7.90 (2 H, d, J=8.59 Hz), 7.67-7.80 (5 H, m), 7.64 (1 H, d, J=15.16 Hz), 6.98 (1 H, d, J=15.16 Hz), 5.95 (1 H, s), 4.19-4.36 (1 H, m), 3.15-3.26 (1 H, m), 3.00-3.11 (1 H, m) ppm. MS (ESI) m/z: 609.9 (M+H)$^+$. Analytical HPLC: RT=7.49 min.

Example 79

(E)-4-(3-Acetamido-6-(3-(5-chloro-2-(1H-tetrazol-1-yl)phenyl)acryloyl)-5,6,7,8-tetrahydro-1,6-naphthyridine-5-carboxamido)benzoic acid, TFA salt

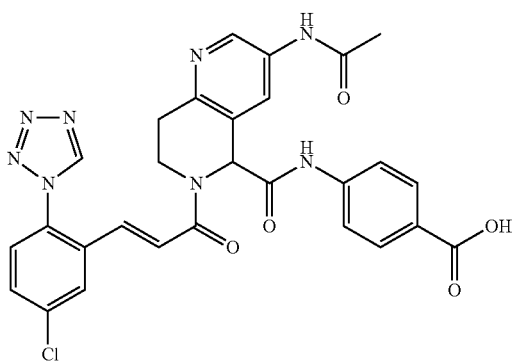 [SMILES: CC(=O)Nc1cnc2c(c1)C(C(=O)Nc1ccc(C(=O)O)cc1)N(C(=O)/C=C/c1cc(Cl)ccc1-n1cnnn1)CC2]

79A: tert-Butyl 3-acetamido-7,8-dihydro-1,6-naphthyridine-6(5H)-carboxylate: To tert-butyl 3-amino-7,8-dihydro-1,6-naphthyridine-6(5H)-carboxylate (0.45 g, 1.805 mmol) in THF (20 mL) was added TEA (0.252 mL, 1.805 mmol) and acetic anhydride (0.170 mL, 1.805 mmol). After 24 h, the reaction was quenched with H$_2$O (15 mL) and extracted with EtOAc (3×30 mL). The combined organic layers were washed with brine (10 mL) and dried (MgSO$_4$). Collected 0.55 g (105%) of 79A as a yellow foam. MS (ESI) m/z: 292.0 (M+H)+.

79B: N-(5,6,7,8-Tetrahydro-1,6-naphthyridin-3-yl)acetamide: 79A (0.55 g, 1.80 mmol) was deprotected with 30% TFA/DCM (20 mL) for 1.5 h. The reaction was concentrated and then, partitioned with sat'd NaHCO$_3$ (15 mL) and EtOAc (50 mL). The organic layer was washed with brine (10 mL) and dried (MgSO$_4$). Only small amount of material was isolated from extraction. Aqueous layer was filtered and concentrated. MS (ESI) m/z: 192.1 (M+H)+.

79C: N-(7,8-Dihydro-1,6-naphthyridin-3-yl)acetamide: Crude 79B and salts were oxidized as in Example 20B. Filtered and concentrated to 0.21 g yellow solid (49%). MS (ESI) m/z: 190.0 (M+H)+.

Example 79 was made from the Ugi reaction using 79C as described in Example 20 to yield 79D, which was hydrolyzed as in Example 20 to yield the desired final product 79. $^1$H NMR (400 MHz, MeOD) δ 10.44-10.64 (1 H, m), 9.50-9.58 (1 H, m), 8.69-8.81 (1 H, m), 8.39-8.48 (1 H, m), 8.20-8.29 (1 H, m), 7.92-8.09 (2 H, m), 7.66-7.75 (2 H, m), 7.57-7.64 (1H, m), 7.37-7.49 (1H, d, J=15.4 Hz), 7.17-7.33 (1 H, d, J=15.4 Hz), 6.07 (1 H, s), 4.15-4.38 (2 H, m), 3.11-3.34 (2 H, m), 2.17 (3 H, s) ppm. MS (ESI) m/z: 587.3 (M+H)$^+$. Analytical HPLC: RT=5.09 min (method B).

Example 80

(E)-4-(2-chloro-6-(3-(5-chloro-2-(1H-tetrazol-1-yl)phenyl)acryloyl)-5,6,7,8-tetrahydro-1,6-naphthyridine-5-carboxamido)benzoic acid, TFA salt

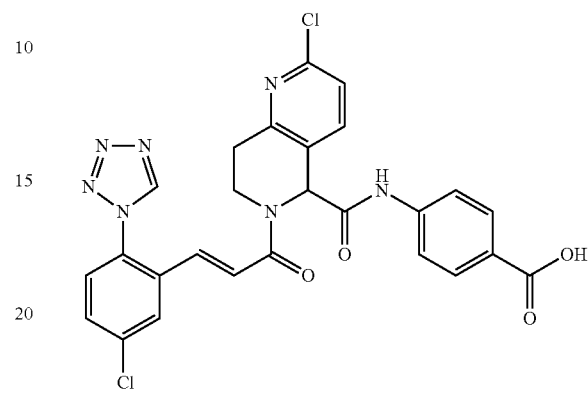

Example 80 was made in a similar manner as Example 20 starting with commercially available 2-chloro-5,6,7,8-tetrahydro-1,6-naphthyridine and Intermediate 6. $^1$H NMR (400 MHz, DMSO-$d_6$) δ 12.77 (1 H, br. s), 10.84 (1 H, s), 9.88 (1 H, s), 8.48 (1 H, d, J=2.3 Hz), 8.01 (1 H, d, J=8.3 Hz), 7.86-7.95 (2 H, m), 7.59-7.83 (5 H, m), 7.47 (1 H, d, J=8.3 Hz), 6.98 (1 H, d, J=15.2 Hz), 5.95 (1 H, s), 4.19-4.39 (2H, m), 3.14-3.22 (1H, m), 3.01-3.11 (1 H, m) ppm. MS (ESI) m/z: 564 (M+H)$^+$. Analytical HPLC: RT=7.67 min.

Example 81

(E)-methyl 4-(2-chloro-6-(3-(5-chloro-2-(1H-tetrazol-1-yl)phenyl)acryloyl)-5,6,7,8-tetrahydro-1,6-naphthyridine-5-carboxamido) phenylcarbamate

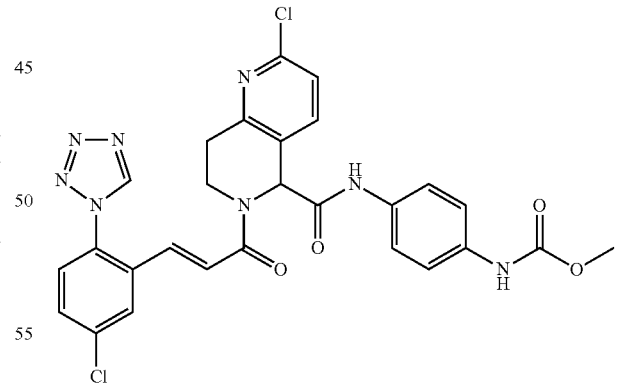

Example 81 was made in a similar manner as Example 80 starting with Intermediate 10. $^1$H NMR (400 MHz, DMSO-$d_6$) δ 2.95-3.15 (2 H, m) 3.62 (3 H, s) 4.21 (1 H, ddd, J=13.33, 8.93, 4.67 Hz) 4.28-4.35 (1 H, m) 5.91 (1 H, s) 6.89-7.03 (1 H, m) 7.32-7.40 (2 H, m) 7.39-7.50 (3 H, m) 7.62 (1 H, d, J=14.84 Hz) 7.69-7.78 (2 H, m) 7.96 (1 H, d, J=8.24 Hz) 8.46 (1 H, d, J=2.20 Hz) 9.57 (1 H, br. s) 9.86 (1 H, s) 10.37-10.46 (1 H, m) ppm. MS (ESI) m/z: 593-595 (M+H)$^+$. Analytical HPLC: RT=7.94 min.

Example 82

(E)-4-(2-(3-(5-chloro-2-(1H-tetrazol-1-yl)phenyl)acryloyl)-1,2,3,4-tetrahydro-2,7-naphthyridine-1-carboxamido)benzoic acid, TFA salt

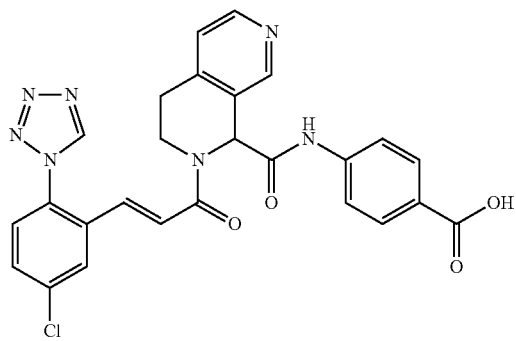 [SMILES: O=C(O)c1ccc(NC(=O)C2c3cnccc3CCN2C(=O)/C=C/c2cc(Cl)ccc2-n2cnnn2)cc1]

Example 82 was made by an Ugi reaction as described in Example 20 starting with commercially available 1,2,3,4-tetrahydro-2,7-naphthyridine. $^1$H NMR (400 MHz, MeOD) δ 9.53 (1 H, s), 8.79 (1 H, s), 8.55 (1 H, br. s), 8.21 (1 H, d, J=1.8 Hz), 7.97 (2H, d, J=8.6 Hz), 7.52-7.72 (4 H, d, J=15.6 Hz), 7.32-7.42 (1 H, m), 7.20-7.31 (1 H, d, J=15.4 Hz), 6.19 (1 H, s), 4.16 (1 H, br. s), 2.56-2.98 (4 H, m) ppm MS (ESI) m/z: 529.9 (M+H)$^+$. Analytical HPLC: RT=4.71 min.

Example 83

(E)-Methyl 4-(6-(3-(5-chloro-2-(1H-tetrazol-1-yl)phenyl)acryloyl)-8,8-dimethyl-3-nitro-5,6,7,8-tetrahydro-1,6-naphthyridine-5-carboxamido)phenylcarbamate

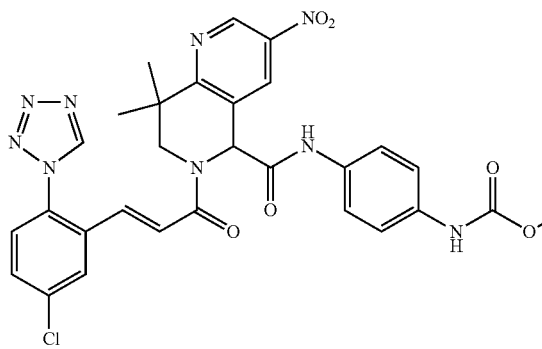

83A: 8,8-Dimethyl-3-nitro-7,8-dihydro-1,6-naphthyridine: 83A was made in a similar manner as Example 20B starting with commercially available tert-butyl 8,8-dimethyl-3-nitro-7,8-dihydro-1,6-naphthyridine-6(5H)-carboxylate. MS (ESI) m/z: 206.1 (M+H)$^+$.

Example 83: Example 83 was made in a similar manner as Example 20 using 83A and Intermediate 2 and Intermediate 10. $^1$H NMR (400 MHz, DMSO-d$_6$) δ 1.26 (3 H, s) 1.52 (3 H, s) 3.65 (3 H, s) 3.99 (1 H, d, J=14.15 Hz) 4.45 (1 H, d, J=14.15 Hz) 6.22 (1 H, s) 7.07 (1 H, d, J=15.16 Hz) 7.36-7.46 (2H, m) 7.47-7.53 (2 H, m) 7.63 (1H, d, J=15.16 Hz) 7.71-7.85 (2 H, m) 8.47 (1 H, d, J=2.02 Hz) 8.76 (1 H, d, J=2.27 Hz,) 9.31 (1 H, d, J=2.53 Hz) 9.61 (1 H, br.s) 9.88 (1 H, s) 10.48 (1 H, s) ppm. MS (ESI) m/z: 632.1 (M+H)$^+$. Analytical HPLC: RT=7.94 min.

Example 84

(E)-methyl 4-(6-(3-(5-chloro-2-(1H-tetrazol-1-yl)phenyl)acryloyl)-3-nitro-5,6,7,8-tetrahydro-1,6-naphthyridine-5-carboxamido)phenylcarbamate, TFA Salt

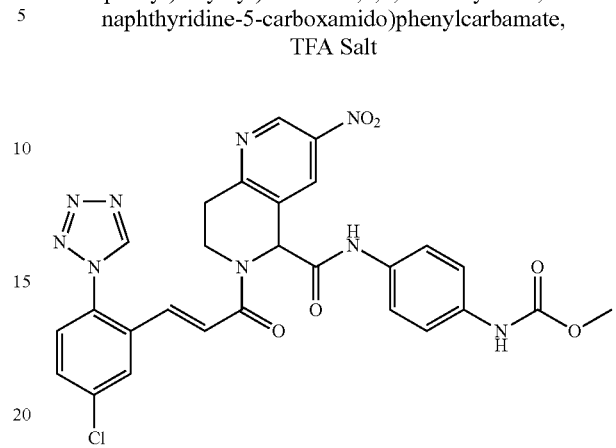

84A: 3-Nitro-7,8-dihydro-1,6-naphthyridine: tert-Butyl 3-nitro-7,8-dihydro-1,6-naphthyridine-6(5H)-carboxylate (0.21 g, 0.752 mmol) was treated with 30% TFA in DCM (10 mL) After 24 h, the reaction was concentrated and the residue was partitioned with saturated NaHCO$_3$ (10 mL) and EtOAc (20 mL). The aqueous layer was extracted with EtOAc (3×20 mL). The combined organic layers were washed with brine (10 mL) and dried (MgSO$_4$). A yellow solid (95 mg) was collected and oxidized with MnO$_2$ as in Example 20B to afford 66 mg of 84A as a brown solid. MS (ESI) m/z: 178 (M+H)$^+$.

Example 84 was prepared by Ugi reaction in a similar manner as Example 20 using 84A, Intermediate 10 and Intermediate 2. $^1$H NMR (400 MHz, DMSO-d$_6$) δ 10.43 (1 H, s), 9.87 (1 H, s), 9.57 (1 H, br. s), 9.26 (1 H, d, J=2.3 Hz), 8.83 (1 H, d, J=2.0 Hz), 8.47 (1 H, d, J=2.0 Hz), 7.72-7.83 (2 H, m), 7.65 (1 H, d, J=15.2 Hz), 7.44-7.54 (2 H, m), 7.35-7.43 (2 H, m), 7.00 (1 H, d, J=15.4 Hz), 6.12 (1 H, s), 4.25-4.40 (2 H, m), 3.65 (3 H, s), 3.14-3.25 (1 H, m), 2.90-3.06 (1 H, m) ppm. MS (ESI) m/z: 604.1 (M+H)$^+$. Analytical HPLC: RT=7.68 min.

Example 85

(E)-4-(6-(3-(5-chloro-2-(1H-tetrazol-1-yl)phenyl)acryloyl)-8,8-dimethyl-3-nitro-5,6,7,8-tetrahydro-1,6-naphthyridine-5-carboxamido)benzoic acid, TFA salt

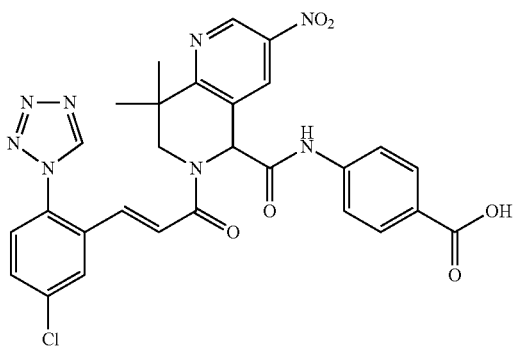 [SMILES: CC1(C)CN(C(=O)/C=C/c2cc(Cl)ccc2-n2cnnn2)C(C(=O)Nc2ccc(C(=O)O)cc2)c2cc([N+](=O)[O-])cnc21]

Example 85 was made in a similar manner as Example 83 substituting Intermediate 6 for Intermediate 10. $^1$H NMR (400 MHz, DMSO-d$_6$) δ 12.78 (1 H, br. s), 10.87 (1 H, s), 9.78-9.95 (1 H, m), 9.29 (1 H, d, J=2.7 Hz), 8.74 (1 H, d, J=2.7 Hz), 8.46 (1 H, d, J=2.2 Hz), 7.90 (2 H, d, J=8.8 Hz), 7.68-7.82 (3 H, m), 7.62 (1 H, d, J=15.4 Hz), 7.05 (1 H, d, J=15.4 Hz), 6.21 (1 H, s), 4.40 (1 H, d, J=14.3 Hz), 3.98 (1 H, d, J=14.3 Hz), 1.51 (3 H, s), 1.25 (3 H, s) ppm. MS (ESI) m/z: 603.0 (M+H)$^+$. Analytical HPLC: RT=8.46 min.

Example 86

(E)-4-(6-(3-(5-chloro-2-(1H-tetrazol-1-yl)phenyl)acryloyl)-5,6,7,8-tetrahydro-1,6-naphthyridine-5-carboxamido)benzoic acid, TFA salt

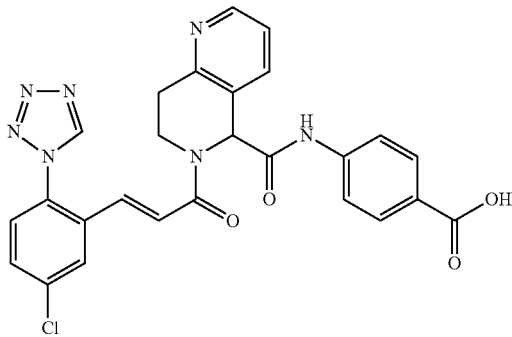 [SMILES: O=C(O)c1ccc(NC(=O)C2c3cccnc3CCN2C(=O)/C=C/c2cc(Cl)ccc2-n2cnnn2)cc1]

86A: 7,8-dihydro-1,6-naphthyridine: 3-bromo-5,6,7,8-tetrahydro-1,6-naphthyridine (0.5 g, 2.347 mmol) in EtOH (30 mL) with 10% Pd/C (40 mg) was hydrogenated at 55 psi for 3.5 h. MS (ESI) m/z: 135.0 (M+H)$^+$. Filtered through Celite® and concentrated to 0.5 g yellow solid which was oxidized with MnO$_2$ as in Example 20B to afford 0.4 g of 86A as an oily yellow solid. MS (ESI) m/z: 133.0 (M+H)$^+$.

Example 86 was made by Ugi reaction as in Example 20 using 86A and Intermediate 2 and Intermediate 6, followed by TFA deprotection. $^1$H NMR (400 MHz, MeOD) δ 9.52 (1 H, s), 8.72 (1 H, d, J=5.6 Hz), 8.54 (1 H, d, J=8.1 Hz), 8.19 (1 H, s), 7.93 (2 H, d, J=8.3 Hz), 7.85-7.92 (1 H, m), 7.62-7.69 (3 H, m), 7.54-7.59 (1 H, m), 7.42 (1 H, d, J=15.2 Hz), 7.22-7.28 (1 H, m), 6.29 (1 H, s), 4.46 (1 H, dd, J=8.7, 4.9 Hz), 4.11-4.29 (1 H, m), 3.44 (2 H, br. s) ppm. MS (ESI) m/z: 530.2 (M+H)$^+$. Analytical HPLC: RT=4.70 min.

Example 87

(E)-Methyl 4-(3-amino-6-(3-(5-chloro-2-(1H-tetrazol-1-yl)phenyl)acryloyl)-5,6,7,8-tetrahydro-1,6-naphthyridine-5-carboxamido)phenylcarbamate, bis TFA salt

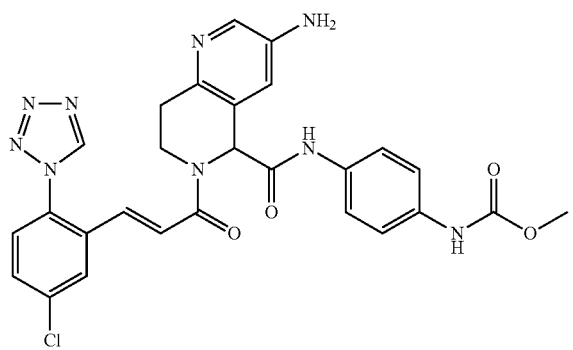

87A: N-(7,8-Dihydro-1,6-naphthyridin-3-yl)-2,2,2-trifluoroacetamide and 7,8-dihydro-1,6-naphthyridin-3-amine: To tert-butyl 3-amino-7,8-dihydro-1,6-naphthyridine-6(5H)-carboxylate (0.227 g, 0.911 mmol) in THF (20 mL) was added TEA (0.190 mL, 1.366 mmol) and TFAA (0.129 mL, 0.911 mmol). After 24 h, the reaction was concentrated and the residue was directly treated with 30% TFA/DCM (20 mL) for 2 h. The reaction was concentrated and the residue was partitioned with saturated NaHCO$_3$ (15 mL) and EtOAc (50 mL). The organic layer was washed with brine (10 mL) and dried (MgSO$_4$) to afford 0.148 g tan foam as a mixture of products. The mixture was oxidized as in Example 20B to afford 87A (0.134 g, 60%) as a mixture. LCMS (ESI) m/z: 244.0 (M+H)$^+$.

Example 87 was made in an Ugi reaction in a similar manner as Example 20 using 87A, Intermediate 2 and Intermediate 10. Purification by reverse phase HPLC afforded 17 mg (10%) of Example 87 as a tan solid. $^1$H NMR (400 MHz, MeOD) δ 9.53 (1 H, s), 8.20 (1 H, d, J=1.8 Hz), 7.93 (1 H, d, J=2.5 Hz), 7.74 (1 H, br. s), 7.69 (1 H, dd, J=8.5, 2.1 Hz), 7.60 (1 H, d, J=8.6 Hz), 7.45 (2 H, d, J=8.8 Hz), 7.33-7.42 (3 H, m), 7.20-7.28 (1 H, d, J=15.4 Hz), 6.11 (1 H, s), 4.36-4.46 (1 H, m), 4.12 (1 H, dd, J=13.9, 7.6 Hz), 3.74 (3 H, s), 3.37 (2 H, s) ppm. MS (ESI) m/z: 574.0 (M+H)$^+$. Analytical HPLC: RT=4.71 min.

Example 88

(E)-7-(3-(5-Chloro-4-fluoro-2-(1H-tetrazol-1-yl)phenyl)acryloyl)-N-(1H-indazol-6-yl)-3-p-tolyl-5,6,7,8-tetrahydro-[1,2,4]triazolo[4,3-a]pyrazine-8-carboxamide

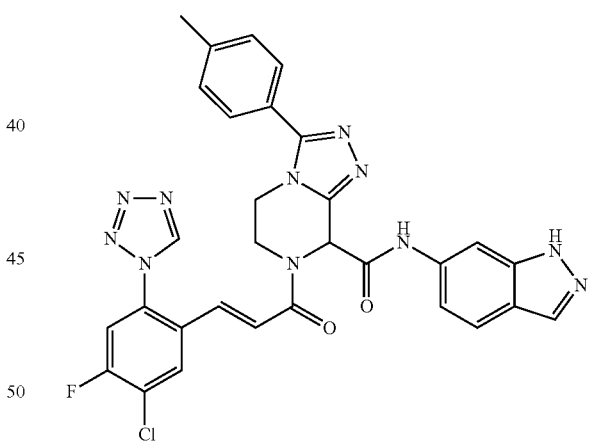

88A: 3-p-Tolyl-5,6,7,8-tetrahydro-[1,2,4]triazolo[4,3-a]pyrazine, TFA salt: 88A was synthesized following a procedure described by Kim et al. J. Med. Chem. 2008, 51, 3,589-602. A solution of 2-(chloromethyl)-5-p-tolyl-1,3,4-oxadiazole (400 mg, 1.917 mmol), ethylenediamine (0.129 mL, 1.917 mmol), DIEA (1.005 mL, 5.75 mmol) in ACN (2 mL) was microwaved 180° C. for 30 min, then stirred at rt overnight. The mixture was concentrated and the residue was purified by normal phase chromatography to afford 88A (286 mg, 45%). MS(ESI) m/z: 215.1 (M+H)$^+$.

88B: 3-p-Tolyl-5,6-dihydro-[1,2,4]triazolo[4,3-a]pyrazine: To a stirred solution of 88A (90 mg, 0.420 mmol) in DCM (1 mL) and MeOH (0.2 mL) was added NCS (63 mg, 0.472 mmol). The reaction was stirred at rt for 1 h and additional 10 mg of NCS was added until the starting material was consumed. The solution was concentrated and the residue was washed with H₂O (2 mL) and dried by co-evaporation with toluene. The resulting 7-chloro-3-p-tolyl-5,6,7,8-tetrahydro-[1,2,4]triazolo[4,3-a]pyrazine was suspended in DCM (4 ml) and DBU (0.063 mL, 0.420 mmol) was added. The solution was stirred at rt for 10 min and then concentrated. Water was added and the mixture was extracted with EtOAc (3×). The combined organic layer was dried with MgSO₄ and concentrated to give 88B (50 mg, 56%) as yellow solid. MS (ESI) m/z: 213.1 (M+H)⁺.

Example 88: Example 88 was prepared in a similar manner as Example 20 using Intermediate 5, 8 and 88B to afford (2.7 mg, 3%) Example 88 as an off white amorphous solid. ¹H NMR (400 MHz, MeOD) δ 9.56 (s, 1 H) 8.35 (s, 1 H) 8.09 (s, 1H) 7.99 (s, 1H) 7.61-7.79 (m, 4 H) 7.44 (d, J=8.03 Hz, 3 H) 7.17-7.31 (m, 2 H) 4.60 (br. s, 1 H) 4.28-4.49 (m, 2 H) 4.19 (br. s, 1 H) 2.45 (s, 3 H) ppm. Analytical HPLC: RT=8.13 min. LC-MS (ESI) m/z: 625.1 (M+H)⁺.

Example 89

(E)-7-(3-(5-Chloro-2-(1H-tetrazol-1-yl)phenyl)acryloyl)-N-(1H-indazol-6-yl)-3-phenyl-5,6,7,8-tetrahydroimidazo[1,2-a]pyrazine-8-carboxamide

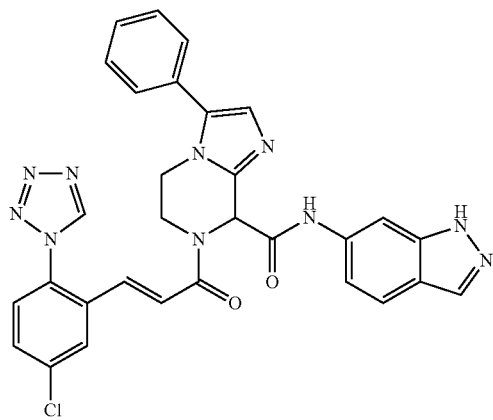 [SMILES: O=C(Nc1ccc2cn[nH]c2c1)C1c2ncc(-c3ccccc3)n2CCN1C(=O)/C=C/c1cc(Cl)ccc1-n1cnnn1]

89A: 3-Phenyl-5,6-dihydroimidazo[1,2-a]pyrazine: 89A was prepared in a similar manner as Example 88B using 3-phenyl-5,6,7,8-tetrahydroimidazo[1,2-a]pyrazine. MS (ESI) m/z: 198.6 (M+H)⁺.

Example 89B: tert-Butyl 6-(3-phenyl-7-(2,2,2-trifluoroacetyl)-5,6,7,8-tetrahydroimidazo[1,2-a]pyrazine-8-carboxamido)-1H-indazole-1-carboxylate: 89B was prepared in a similar manner as previously described using Intermediate 2, 89A and trifluoroacetic acid to afford 94 mg of desired product 89B as (35.1% yield) glass. MS (ESI) m/z: 555.0 (M+H)⁺.

Example 89C: tert-Butyl 6-(3-phenyl-5,6,7,8-tetrahydroimidazo[1,2-a]pyrazine-8-carboxamido)-1H-indazole-1-carboxylate: 89C was prepared following a procedure described by V. G. Nenajdenko et al. Tetrahedron 62(2006) 5922-5930. To a solution of 89B (94 mg, 0.141 mmol) in EtOH (5 mL) was added NaBH₄ (26.6 mg, 0.703 mmol). After 0.5 h the reaction was concentrated and saturated NaHCO₃ (1 mL) was added. The mixture was extracted with EtOAc (2×) to give 89C (67 mg, 104%) as yellow foam which was used without further purification. MS (ESI) m/z: 459.1 (M+H)⁺.

Example 89: Example 89 was prepared in a similar manner as Example 1C using 89C and Intermediate 1 and deprotected with 4N HCl in dioxane for 1 h at rt. Purification by reverse phase HPLC afforded Example 89 (2.11 mg, 5%) as a white amorphous solid. ¹H NMR (400 MHz, MeOD) δ 9.65 (s, 1 H) 7.93-8.16 (m, 2 H) 7.61-7.80 (m, 2 H) 7.31-7.57 (m, 7 H) 7.26 (s, 1 H) 6.79 (d, J=8.28 Hz, 1 H) 4.57 (dd, J=14.05, 4.27 Hz, 1 H) 4.06-4.25 (m, 2 H) 3.98 (dd, J=12.55, 3.76 Hz, 1 H) 3.08-3.26 (m, 2 H) 2.96 (dd, J=16.81, 8.78 Hz, 1 H) ppm. MS (ESI) m/z: 591.0 (M+H)⁺. Analytical HPLC: RT=7.57 min.

Example 90

(E)-4-(6-(3-(5-Chloro-2-(1H-tetrazol-1-yl)phenyl)acryloyl)-3-isobutyramido-5,6,7,8-tetrahydro-1,6-naphthyridine-5-carboxamido)benzoic acid, TFA salt

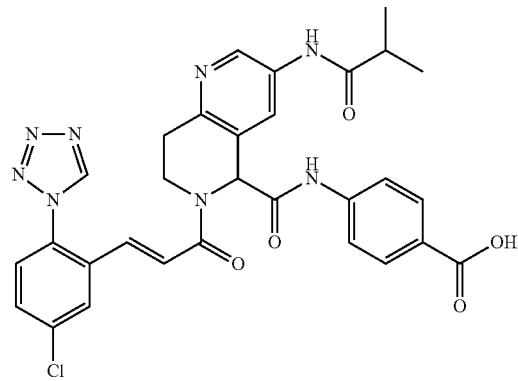 [SMILES: CC(C)C(=O)Nc1cnc2c(c1)C(C(=O)Nc1ccc(C(=O)O)cc1)N(C(=O)/C=C/c1cc(Cl)ccc1-n1cnnn1)CC2]

Example 90 was made in a similar manner as Example 79 substituting isobutyric anhydride for acetic anhydride. ¹H NMR (400 MHz, MeOD) δ 9.42 (1 H, s), 8.64 (1 H, d, J=2.3 Hz), 8.28 (1 H, br. s), 8.12 (1 H, d, J=1.8 Hz), 7.82-7.97 (2 H, d, J=8.59 Hz), 7.54-7.67 (2 H, m), 7.48 (1 H, d, J=8.6 Hz), 7.30 (1 H, d, J=15.2 Hz), 7.12 (1 H, d, J=15.4 Hz), 5.95 (1 H, s), 4.07-4.27 (2H, m), 2.43-2.94 (4 H, m), 1.04-1.15 (6 H, m) ppm. MS (ESI) m/z: 615.2 (M+H)+. Analytical HPLC: RT=5.52 min Example 91

(E)-4-(6-(3-(5-chloro-2-(1H-tetrazol-1-yl)phenyl)acryloyl)-3-(N-methylcyclopropanecarboxamido)-5,6,7,8-tetrahydro-1,6-naphthyridine-5-carboxamido)benzoic acid, TFA salt

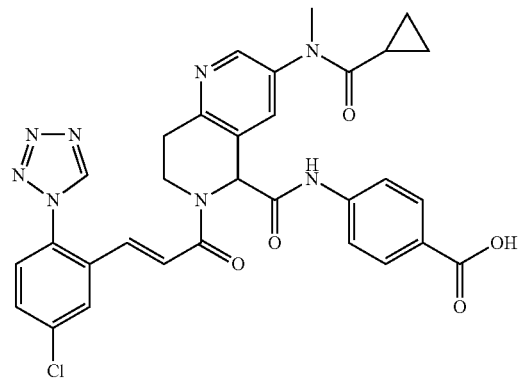 [SMILES: CN(C(=O)C1CC1)c1cnc2c(c1)C(C(=O)Nc1ccc(C(=O)O)cc1)N(C(=O)/C=C/c1cc(Cl)ccc1-n1cnnn1)CC2]

Example 91 was made in a similar manner as Example 79 substituting N-(7,8-dihydro-1,6-naphthyridin-3-yl)-N-methylcyclopropanecarboxamide in the Ugi reaction. $^1$H NMR (MeOD) δ 9.43 (s, 1 H), 8.46 (d, J=2.0 Hz, 1 H), 8.13 (d, J=2.0 Hz, 1 H), 7.93-7.85 (m, 3 H), 7.67-7.46 (m, 4H), 7.33 (d, J=15.0 Hz, 1 H), 7.16 (d, J=15.0 Hz, 1 H), 6.01 (s, 1 H), 4.17 (t, 2 H), 3.20-3.05 (m, 2H0, 2.77 (s, 3H), 1.40 (bm, 1H), 0.88-0.47 (bm, 4H) ppm. MS (ESI) m/z: 627.3 (M+H)$^+$. Analytical HPLC: RT=6.68 min (Method B).

The following examples in Table 3 were made from (E)-tert-butyl 4-(3-amino-6-(3-(5-chloro-2-(1H-tetrazol-1-yl)phenyl)acryloyl)-5,6,7,8-tetrahydro-1,6-naphthyridine-5-carboxamido)benzoate, which was made in a manner similar to Example 79.

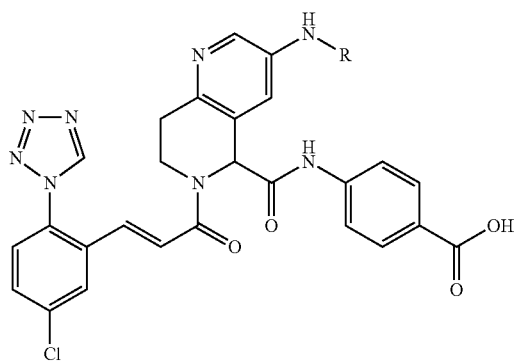

TABLE 3

| Example # | R | M + H | RT* |
|---|---|---|---|
| 92 | | 678.9 | 2.26 |
| 93 | | 644.9 | 2.19 |
| 94 | | 663.9 | 2.06 |
| 95 | | 629.9 | 1.82 |
| 96 | | 615.9 | 1.70 |

TABLE 3-continued

| Example # | R | M + H | RT* |
|---|---|---|---|
| 97 | | 600.8 | 1.73 |
| 98 | | 614.8 | 1.86 |
| 99 | | 691.9 | 2.12 |
| 100 | | 697.7 | 2.23 |
| 101 | | 693.9 | 2.02 |
| 102 | | 677.9 | 2.03 |

RT* Column: Supelco Ascentis Express 4.6 × 50 mm 2.7 uM C18.
Mobile Phase: A = 5:95 ACN:H$_2$O; B = 95:5 Acetrile:H$_2$O; Modifier = 0.05% TFA
Wavelength: 220 nm.
A = Method A.

What is claimed is:

1. A compound of Formula (I):

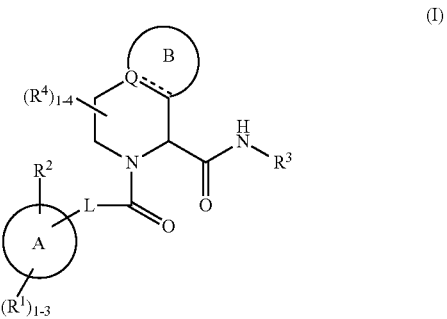

or a pharmaceutically acceptable salt thereof, wherein:
ring A is a $C_{3-10}$ carbocycle;
L is selected from the group consisting of: a bond, —CHR$^{10}$CHR$^{10}$—, —CR$^{10}$=CR$^{10}$—, and —C≡C—;

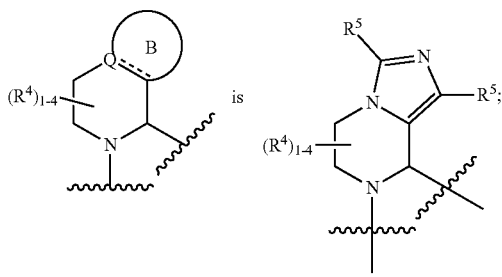

each $R^1$, is independently selected from the group consisting of: —H, halo, —$C_{1-2}$ alkyl, —$OC_{1-4}$ alkyl, —CN, —$CH_2NH_2$, and —C(=NH)$NH_2$;

$R^2$ is selected from the group consisting of: —H, halo, —CN, —OH, —$C_{1-6}$ alkyl, —$OC_{1-4}$ alkyl, $C_{1-6}$haloalkyl, —$OC_{1-6}$haloalkyl, —CO($C_{1-4}$ alkyl), —$CONH_2$, —$CO_2H$ and a 5- to 7-membered heterocyclic group, wherein the 5- to 7-membered heterocyclic group contains one or more carbon atoms and 1-4 heteroatoms or heteroatomic gorups selected from N, NH, N($C_{1-4}$ alkyl), O, and $S(O)_p$; and wherein said 5- to 7-membered heterocyclic group is substituted with 1-2 $R^{2a}$;

each $R^{2a}$ is independently selected from the group consisting of: —H, halo, —$C_{1-4}$ alkyl, —$CO_2H$, —$CO_2$ ($C_{1-4}$ alkyl), —$CONH_2$, —$CH_2OH$, —$CH_2OC_{1-4}$alkyl, and —$CH_2NH_2$;

$R^3$ is selected from the group consisting of: $C_{1-6}$ alkyl substituted with 1-3 $R^{3a}$, a $C_{3-10}$ carbocycle substituted with 1-3 $R^{3a}$, and a 5-10 membered heterocyclic group containing one or more carbon atoms and 1-4 heteroatoms or heteroatomic groups selected from the group consisting of N, $NR^7$, O, and $S(O)_p$; wherein said heterocyclic group is substituted with 1-3 $R^{3a}$;

each $R^{3a}$ is independently selected from the group consisting of —H, =O, halo, —$C_{1-4}$ alkyl, —OH, —$OC_{1-4}$ alkyl, —CN, —$NH_2$, —NH($C_{1-4}$ alkyl), —N($C_{1-4}$ alkyl)$_2$, —$CO_2H$, —$CH_2CO_2H$, —$CO_2$ ($C_{1-4}$ alkyl), —$CO_2$—$C_{1-4}$ alkylene—O($C_{1-4}$ alkyl), —$CO_2$—$C_{1-4}$ akylene—N($C_{1-4}$ alkyl)$_2$, —$CO_2$—$C_{1-4}$ alkylene—O—$C_{1-4}$ alkylene—N($C_{1-4}$ alkyl)$_2$, —$CO_2$—$C_{1-4}$ alkylene—O($C_{1-4}$ alkyl), —$CONH_2$, —CONH($C_{1-6}$ alkyl), —CON($C_{1-4}$ alkyl)$_2$, —CONH—$C_{1-4}$ alkylene—$CO_2$($C_{1-4}$ alkyl), —$CONHCO_2C_{1-4}$ alkyl, —CONH—$C_{1-4}$ alkylene—NHCO($C_{1-4}$ alkyl), —CONH-$C_{1-4}$ alkylene—$CONH_2$, —$NHCOC_{1-4}$ alkyl, —$NHCO_2$ ($C_{1-4}$ alkyl), —$CH_2NHCO_2(C_{1-4}$ alkyl), $R^c$, —CONH $R^c$, and —$CO_2R^c$;

each $R_4$ is independently selected from the group consisting of —H, halo, and —$C_{1-4}$ alkyl;

each $R_5$ is independently selected from the group consisting of —H, halo, —$C_{1-4}$ alkyl, —$C_{2-4}$ alkenyl, —$C_{2-4}$ alkynyl, —OH, —CN, $NO_2$, —$NH_2$, —N($C_{1-4}$alkyl)$_2$, —O($C_{1-4}$alkyl), —OCO($C_{1-4}$alkyl_, —O—$C_{1-4}$alkylene—O($C_{1-4}$ alkyl), —O—$C_{1-4}$ alkylene—N($C_{1-4}$ alkyl)$_2$, —$CO_2H$, —$CO_2(C_{1-4}$ alkyl), —$CONH_2$, —($CH_2)_2CONH_2$, —$CONR^9(C_{1-4}$ alkyl), —CON($C_{1-4}$ alkyl)$_2$, —$CONR^9$—$C_{1-4}$ alkylene—O($C_{1-4}$ alkyl), —$CONR^9$—$C_{1-4}$alkylene—N($C_{1-4}$ alkyl)$_2$, —$CONR^9$—$C_{1-4}$ alkylene—$CO_2$ ($C_{1-4}$ alkyl), —$NR^9COC_{1-4}$ alkyl, —$NR^9CO_2C_{1-4}$ alkyl, —$NR^9CONH(C_{1-4}$alkyl), —$NR^9CONR^9$—$C_{1-4}$ alkylene—$CO_2C_{1-4}$ alkyl, —$NR^9$—$C_{1-4}$ alkylene—N ($C_{1-4}$ alkyl)$_2$, —$NR^0SO_2$ ($C_{1-4}$ alkyl), —$SO_2NH_2$, —$R^8$, —$OR^8$, —$COR^8$, —$COR^8$, —$CONR^9R^8$, —$NR^9COR^8$, —$NR^9CO_2R^8$, and —$NR^9CONR^9R^8$, wherein the —$C_{1-4}$ alkyl, —$C_{2-4}$ alkenyl and —$c_{2-4}$ alkynyl are optionally substituted with 1-2 $R^b$;

each $R^7$ is independently selected from the group consisting of —H, —$C_{1-4}$ alkyl, —$COC_{1-4}$ alkyl, $CO_2(C_{1-4}$ alkyl), —CONH—$C_{1-4}$ alkylene—$CO_2C_{1-4}$ alkyl, phenyl, benzyl, and —$CO_2$—$C_{1-4}$ alkylene-aryl;

each $R^8$ is —($CH_2)_n$—$C_{3-10}$ carbocycle or a —($CH_2)_n$5- to 10-membered heterocyclic group, wherein the 5 to 10-membered heterocyclic group contains one or more carbon atoms and 1- 4 heteroatoms or heteroatomic groups selected from the group consisting of N, $NR^a$, O, and $S(O)_p$; and wherein the $C_{3-10}$ carbocycle and 5- to 10-membered hetercyclic group are optionally substituted with 1-3 $R^b$;

each $R^9$ is independently —H or —$C_{1-4}$ alkyl;

each $R^{10}$ is independently selected from the group consisting of —H, halo, —OH, and —$C_{1-4}$ alkyl;

each $R^a$ is independently selected from the group consisting of —H, —$C_{1-4}$ alkyl, —($CH_2)_n$OH, —CO($C_{1-4}$ alkyl), —$COCF_3$, —$CO_2(C_{1-4}$ alkyl), —$CONH_2$, —CONH— $C_{1-4}$ alkylene—$CO_2(C_{1-4}$ alkyl), —$C_{1-4}$ alkylene—$CO_2(C_{1-4}$ alkyl), $R^c$, $CO_2R^c$, and —$CONHR^c$;

each $R^b$ is independently selected from the group consisting of =O, halo, —$C_{1-4}$ alkyl, —$OC_{1-4}$alkyl, —$OCF_3$, —$NH_2$, —$NO_2$, N($C_{1-4}$ alkyl)$_2$, —CO($C_{1-4}$ alkyl), —CO($C_{1-4}$ haloalkyl), —$CO_2(C_{1-4}$ alkyl), —$CONH_2$, —CONH($C_{1-4}$ alkyl), —CON($C_{1-4}$alkyl)$_2$, —CONH— $C_{1-4}$ alkylene—O($C_{1-4}$ alkyl), —CONH—$C_{1-4}$ alkylene—N($C_{1-4}$ alkyl)$_2$, —$NHCO_2(C_{1-4}$ alkyl), —$R^c$, —$COR^c$, —$CO_2R^c$, and —$CONHR^2$;

each $R^c$ is independently selected from the group consisting of —($CH_2)_n$—$C_{3-6}$ cycloalkyl, —($CH_2)_n$—phenyl, and —($CH_2)_n$—5- to 6-membered heterocyclic group, wherein the 5- to 6-membered heterocyclic group contains one or mroe carbon atoms and 1-4 heteroatoms or heteroatomic groups selected from the group consisting of N, NH, N($C_{1-4}$alkyl), N($CO_2C_{1-4}$ alkyl), O, and S(O); and, wherein the $C_{3-6}$ cycloalkyl, phenyl and 5- to 6-membered heterocyclic group are optionally substituted with 1-2 $R^d$;

each $R^d$ is independently selected from the group consisting of =O, halo, —OH, —$C_{1-4}$ alkyl, —N($C_{1-4}$ alkyl)$_2$, $OC_{1-4}$ alkyl, —NHCO($C_{1-4}$ alkyl), and a heterocyclic group, wherein the heterocyclic group contains one or more carbon atoms and 1-4 heteroatoms or heteroatomic groups selected from the group consisting of N, NH, N($C_{1-4}$ alkyl), O, and S(O);p each n is independently selected from 0, 1, 2, 3, and 4; and each p is independently selected from 0, 1, and 2.

2. The compound of claim 1, wherein the compound has Formula (V):

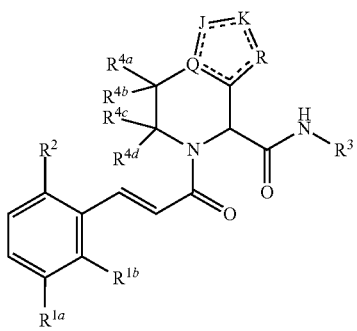

(V)

or a pharmaceutically acceptable salt thereof, wherein:

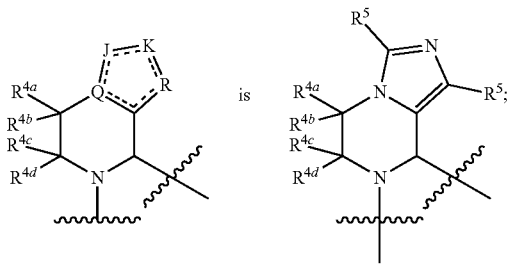

is $R^{1a}$ is selected from the group consisting of —H, halo, —$C_{1-2}$ alkyl, and —$OCH_3$;
$R^{1b}$ is —H or halo;
$R^2$ is selected from the group consisting of —H, —F, —CN, —OH, —$OC_{1-4}$alkyl, —$CHF_2$, —$CF_3$, —$OCHF_2$, —$CO(C_{1-4}$ alkyl), —$CONH_2$, —$CO_2H$, triazole substituted with $R^{2a}$, and a tetrazole substituted with $R^{2a}$;
$R^{2a}$ is selected from the group consisting of —H, halo, —$C_{1-4}$ alkyl, —$CO_2H$, —$CO_2(C_{1-4}$ alkyl), —$CONH_2$, —$CH_2OH$, —$CH_2OC_{1-4}$alkyl, and —$CH_2NH_2$;
$R^3$ is selected from the group consisting of $C_{1-6}$ alkyl substituted with 1-3 $R^{3a}$, a $C_{3-10}$ carbocycle substituted with 1-3 $R^{3a}$, and 5-10 membered heterocyclic group containing one or carbon atoms and 1-4 heteroatoms or heteroatomic groups selected from the group consisting of N, $NR^7$, O, and $S(O)_p$; wherein said heterocyclic group is substituted with 1-3 $R^{3a}$;
each $R^{3a}$ is independently, selected from the group consisting of =O, halo, —$C_{1-4}$ alkyl, —OH, —$O(C_{1-4}$ alkyl), —CN, —$NH_2$, —$CO_2H$, —$CO_2$ ($C_{1-4}$ alkyl), —$CONHCO_2$ ($C_{1-4}$ alkyl), —$NHCOC_{1-4}$ alkyl, —$(CH_2)NHCO_2(C_{1-4}$ alkyl) and $R^c$;
$R^{4a}$, $R^{4b}$, $R^{4c}$, and $R^{4d}$ are independently selected from the group consisting of —H, —F and —$C_{1-4}$ alkyl;
each $R^4$ is independently selected from the group consisting of —H, —$C_{1-4}$ alkyl, halo, —$NO_2$, —$NH_2$, —$NR^9COC_{1-4}$ alkyl, —$NR^9CO_2C_{1-4}$ alkyl, —$NR^9CONH(C_{1-4}$ alkyl), —$NR^9$—$C_{1-4}$ alkylene—N($C_{1-4}$ alkyl)$_2$, $R^8$, —$NR^9COR^8$, —$NR^9CO_2R^8$, and —$NR^9CONR^9R^8$;
each $R^7$ is independently selected from the group consisting of —H, —$C_{1-4}$ alkyl, —$COC_{1-4}$ alkyl, $CO_2(C_{1-4}$ alkyl), —CONH—$C_{1-4}$ alkylene—$CO_2C_{1-4}$ alkyl, phenyl, benzyl, and —$CO_2$—$C_{1-4}$ alkylene-aryl;
each $R^8$ is independently selected from the group consisting of —$(CH_2)_n$—$C_{3-6}$ cycloalkyl, —$(CH_2)_n$-phenyl and —$(CH_2)_n$—5- to 10-membered heterocyclic group containing one or more carbon atoms and 1-4 heteroatoms or heteroatomic groups independently selected from the group consisting of N, $HR^a$, O, and $S(O)_p$, wherein said cycloalkyl, phenyl or heterocyclic group is optionally substituted with 1-3 $R^b$;
$R^9$ is —H or —$C_{1-4}$ alkyl;
each $R^a$ is independently selected from the group consisting of —H, —$C_{1-4}$ alkyl, —$(CH_2)_nOH$, —$CO(C_{1-4}$ alkyl), —$COCF_3$, —$CO_2(C_{1-4}$ alkyl), —$CONH_2$, —CONH—$C_{1-4}$ alkylene—$CO_2$ ($C_{1-4}$alkyl), $C_{1-4}$alkylene—$CO_2(C_{1-4}$ alkyl), $R^c$, $CO_2R^c$, and $CONHR^c$;
each $R^b$ is independently selected from the group consisting of =O, halo, —$C_{1-4}$ alkyl, —$OC_{1-4}$ alkyl, —$OCF_3$, —$NH_2$, —$NO_2$, —N($C_{1-4}$ alkyl)$_2$, —$CO(C_{1-4}$ alkyl), —$CO(C_{1-4}$ haloalkyl), —$CO_2(C_{1-4}$ alkyl), —$CONH_2$, $CONH(C_{1-4}$ alkyl), —$CON(C_{1-4}$ alkyl)$_2$, —CONH—$C_{1-4}$ alkylene—$O(C_{1-4}$ alkyl), —CONH—$C_{1-4}$ alkylene—N($C_{1-4}$ alkyl)$_2$, —$NHCO_2(C_{1-4}$ alkyl), —$R^c$, —$COR^c$, —$CO_{2,1R}{}^c$ and —$CONHR^c$;
each $R^c$ is independently selected from the group consisting of —$(CH_2)_n$—$C_{3-6}$ cycloalkyl, —$(CH_2)_n$phenyl, and —$(CH_2)_n$—5- to 6-membered heterocyclic group, wherein the 5- to 6-membered heterocyclic group contains one or more carbon atoms and 1-4 heteroatoms or heteroatomic groups independently selected from the group consisting of N, NH, N($C_{1-4}$alkyl), N($CO_2C_{1-4}$ alkyl), O, and S(O)p; and, wherein the $C_{3-6}$ cycloalkyl, phenyl and 5- to 6-membered heterocyclic group are optionally substituted with 1-2 $R^2$;
each $R^d$ is independently selected from the group consisting of =O, halo, —OH, —$C_{1-4}$ alkyl, —N($C_{1-4}$ alkyl)$_2$, —$OC_{1-4}$alkyl, —NHCO($C_{1-4}$ alkyl), and a heterocyclic group, wherein the heterocyclic group contains one or more carbon atoms and 1-4 heteroatoms or heteroatomic groups selected from the group consisting of N, NH, N($C_{1-4}$ alkyl), O, and $S(O)_p$;
each n is independently selected from 0, 1, 2, 3, and 4; and
each p is independently selected from 0, 1, and 2.

3. The compound of claim 2, having Formula (VIII):

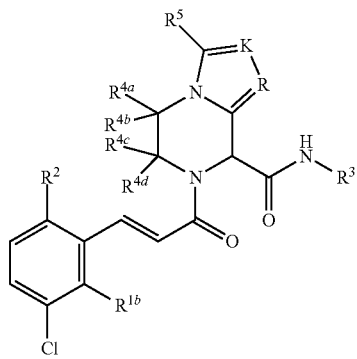

(VIII)

or a pharmaceutically acceptable salt thereof, wherein:

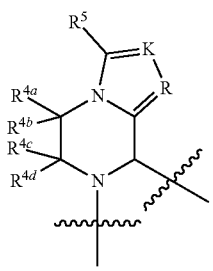 is 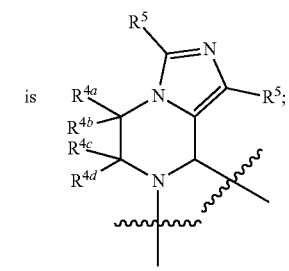

$R^{1b}$ is —H or —F;

$R^2$ is selected from the group consisting of —H, —F, —CF$_3$, —C(O)CH$_3$, and tetrazole;

$R^3$ is phenyl or indazole;

each $R^5$ is independently —H or —R$^8$;

each $R^8$ is independently selected from the group consisting of phenyl and 5- to 10- membered heterocyclic group, wherein the 5- to 10-membered heterocyclic group contains one or more carbon atoms and 1-4 heteroatoms or heteroatomic groups selected from the group consisting of N, HR$^a$, O, and S; and, wherein said phenyl or heterocyclic group is optionally substituted with 1-3 R$^b$;

each $R^{4a}$, $R^{4b}$, $R^{4c}$, and $R^{4d}$ are independently selected from the group consisting of —H, —F, and —C$_{1-4}$ alkyl;

each $R^a$ is —H or —C$_{1-4}$ alkyl; and each $R^b$ is selected from the group consisting of —C$_{1-4}$ alkyl, —OC$_{1-4}$alkyl, and —CONH$_2$.

4. A pharmaceutical composition comprising a pharmaceutically acceptable carrier and a therapeutically effective amount of a compound of claim 1 or a pharmaceutically acceptable salt thereof.

\* \* \* \* \*